(12) United States Patent
Sasaki et al.

(10) Patent No.: US 8,916,526 B2
(45) Date of Patent: Dec. 23, 2014

(54) FLAVANONE DERIVATIVE

(75) Inventors: Kenji Sasaki, Okayama (JP); Tomofusa Tsuchiya, Okayama (JP); Abugafar Md. Lokman Hossion, Okayama (JP); Nao Ohtsuka, Okayama (JP); Yoshito Zamami, Okayama (JP); Yuji Kurosaki, Okayama (JP)

(73) Assignee: National University Corporation Okayama University, Okayama-Shi, Okayama (JP)

( * ) Notice: Subject to any disclaimer, the term of this patent is extended or adjusted under 35 U.S.C. 154(b) by 148 days.

(21) Appl. No.: 13/388,073

(22) PCT Filed: Jul. 29, 2010

(86) PCT No.: PCT/JP2010/062759
§ 371 (c)(1),
(2), (4) Date: Apr. 24, 2012

(87) PCT Pub. No.: WO2011/013735
PCT Pub. Date: Feb. 3, 2011

(65) Prior Publication Data
US 2012/0202980 A1 Aug. 9, 2012

(30) Foreign Application Priority Data

Jul. 31, 2009 (JP) ................................. 2009-178718

(51) Int. Cl.
*A61K 31/70* (2006.01)
*C07H 17/00* (2006.01)
*C07H 17/07* (2006.01)

(52) U.S. Cl.
CPC ...................................... *C07H 17/07* (2013.01)
USPC .................................................. 514/27; 536/8

(58) Field of Classification Search
USPC ........................................................... 536/8
See application file for complete search history.

(56) References Cited

FOREIGN PATENT DOCUMENTS

WO WO 2006/092081 A1 * 9/2006

OTHER PUBLICATIONS

Hongmei Liu et al: "Acylated Flavonol Glycosides from Leaves of *Stenochlaena palustris*", Journal of Natural Products, American Chemical Society, US, vol. 62, No. 1, Jan. 1, 1999, pp. 70-75.
Clio Christopoulou et al: "Chemosystematic Value of Chemical Constituents from *Scabiosa hymettia* (Dipsacaceae)", Chemistry & Biodiversity, vol. 5, No. 2, Feb. 1, 2008, pp. 318-323.
Heyman H M et al: "Antibacterial activity of South African medicinal plants against methicillin resistant *Staphylococcus aureus*", Pharmaceutical Biology, Swets and Zeitlinger, Lisse, NL, vol. 47, No. 1, Jan. 1, 2009, pp. 67-71.
Vivyanne S. Falcao-Silva et al: "Modulation of drug resistance in *Staphylococcus aureus* by a kaempferol glycoside from *Herissantia tiubae* (malvaceae)", Phytotherapy Research, vol. 23, No. 10, Feb. 10, 2009, pp. 1367-1370.
Mei-Hua Liu et al: "Synergistic Effect of Kaempferol Glycosides Purified from *Laurus nobilis* and Fluoroquinolones on Methicillin-Resistant *Staphylococcus aureus*", Biological & Pharmaceutical Bulletin, vol. 32, No. 3, Jan. 1, 2009, pp. 489-492.
Nao Otsuka et al: "Anti-methicillin Resistant *Staphylococcus aureus* (MRSA) Compounds Isolated from *Laurus nobilis*", Biological & Pharmaceutical Bulletin, vol. 31, No. 9, Sep. 1, 2008, pp. 1794-1797.
Peter Nemes et al: "Laser Ablation Electrospray Ionization for Atmospheric Pressure, in Vivo, and Imaging Mass Spectrometry", Analytical Chemistry, vol. 79, No. 21, Nov. 1, 2007, pp. 8098-8106.
Barbara Vermes et al: "Structure Elucidation and Synthesis of Flavonol Acylglycosides. IIL. The synthesis of tiliroside", Helvetica Chimica Acta, vol. 64, No. 6, Sep. 23, 1981, pp. 1964-1967.
Tamotsu Nikaido et al: "Inhibition of adenosine 3',5'-cyclic monophosphate phosphodiesterase by flavonoids. II.", Chemical & Pharmaceutical Bulletin, vol. 36, No. 2, Jan. 1, 1988, pp. 654-661.
Zhiyun Meng et al: "Effect of five flavonoid compounds isolated from *Quercus dentata* Thunb on superoxide generation in human neutrophils and phosphorylation of neutrophil proteins", Clinica Chimica Acta, vol. 306, No. 1-2, Apr. 1, 2001, pp. 97-102.
Hunsa Prawat et al: "Cyanogenic and non-cyanogenic glycosides from *Manihot esculenta*", Phytochemistry, vol. 40, No. 4, Nov. 1, 1995, pp. 1167-1173.
Latifa Chebil et al: "Enzymatic Acylation of Flavonoids: Effect of the Nature of the Substrate, Origin of Lipase, and Operating Conditions on Conversion Yield and Regioselectivity", Journal of Agricultural and Food Chemistry, vol. 55, No. 23, Nov. 1, 2007, pp. 9496-9502.
Giovanni Romussi et al: "Constituents of Cupuliferae, XVII: Triterpene Saponins and Falvonoids from *Quercus laurifolia* Michx. ", Archiv Der Pharmazie, vol. 326, No. 9, Jan. 1, 1993, pp. 525-528.
D'Agostino M et al: "Flavonol glycosides from *Tagetes elliptica*", Phytochemistry, Pergamon Press, GB, vol. 31, No. 12, Dec. 1, 1992, pp. 4387-4388.

(Continued)

*Primary Examiner* — Elli Peselev
(74) *Attorney, Agent, or Firm* — Don D. Cha; Hamilton DeSanctis & Cha, LLP

(57) ABSTRACT

Provided is a novel antimicrobial agent. More specifically, provided is a novel antimicrobial agent capable of effectively acting on various resistant bacteria such as VSSA, MRSA, VISA, VRE, and VRSA. A novel flavanone derivative having a six-membered monosaccharide derivative, specifically, a glucose derivative or a galactose derivative is capable of effectively acting on the bacteria. More specifically, a compound represented by the general formula (I) is capable of effectively acting on the bacteria.

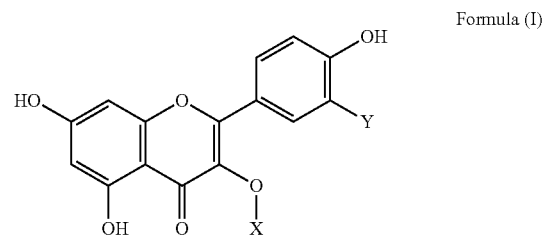

Formula (I)

(In the formula: X represents a six-membered monosaccharide derivative; and Y is substituted by a hydroxyl group.)

7 Claims, 3 Drawing Sheets

(56) References Cited

OTHER PUBLICATIONS

Benish Iftikhar et al: "Structural determination of quercusides A and B, new flavonoid glucosides from *Quercus incana*, by 1 D and 2D NMR spectroscopy", Magnetic Resonance in Chemistry, vol. 47, No. 7, Jul. 1, 2009, pp. 605-608.

Carla Aparecida Pedriali et al: "The synthesis of a water-soluble derivative of rutin as an antiradical agent", Quimica Nova, vol. 31, No. 8, Jan. 1, 2008, pp. 2147-2151.

Database CA [Online] Chemical Abstracts Service, Columbus, Ohio, US; Marzouk, Mohamed S. A.: "Acylated flavonol glycosides and hydrolysable tannins from *Euphorbia cotinifolia* L. leaves", retrieved from STN Database accession No. 2009:208633, XP055055961.

Romussi G et al: "Constituents of Cupuliferae 8. A Novel Highly Acylated Astragalin From *Quercus-ilex*", Liebigs Annalen Der Chemie, No. 11, 1984, pp. 1864-1866.

Zhou Yingjun et al: "Study on chemical constituents of *Querdcus engleriana*", Shenyang Yaoke Daxue Xuebao—Journal of Shenyang Pharmaceutical University, Chinese Electronic Periodical Services, Liaoning, CN, vol. 17, No. 4, Jan. 1, 2000, pp. 263-266.

Alluis B et al: "Water-soluble flavonol (= 3-hydroxy-2-phenyi-4H-1-benzopyran-4-one) derivatives: Chemical synthesis, colouring, and antioxidant properties", Helvetica Chimica Acta 2000 Ch, vol. 83, No. 2, 2000, pp. 428-443.

Nishimura T et al: "Fiavonoids That Mimic Human Ligands from the Whole Plants of *Euphorbia* lunulata", Chemical and Pharmaceutical Bulletin, Pharmaceutical Society of Japan, JP, vol. 53, No. 3, 1 Mar. 2005, pp. 305-308.

Chen L et al: "Binding interaction of quercetin-3-beta-galactoside and its synthetic derivatives with SARS-CoV 3CL pro: Structure-activity relationship studies reveal salient pharmacophore features", Bioorganic & Medicinal Chemistry, Pergamon, GB, vol. 14, No. 24, Dec. 15, 2006, pp. 8295-8306.

Yoshiaki Amakura et al: "Four new hydrolyzable tannins and an acylated flavonol glycoside from *Euphorbia maculata*", Canadian Journal of Chemistry, vol. 75, No. 6, Jun. 1, 1997, pp. 727-733.

Helena Correia et al: "Characterisation of polyphenols by HPLCPAD-ESE/MS and antioxidant activity in *Equisetum telmateia*.", Phytochemical Analysis, vol. 16, No. 5, Jan. 1, 2005, pp. 380-387.

H. Wagner et al: "Fiavonol-3-glycosides in eight *Hymenoxys* species", Phytochemistry, vol. 11, No. 10, Oct. 1, 1972, pp. 3087-3088.

Dilek Ercil et al: "0-Galloyl Flavonoids from *Geranium pyrenaicum* and Their in vitro Antileishmanial Activity", Turkish Journal of Chemistry, Jan. 1, 2005, pp. 437-443.

Hossion A M L et al: "Design, synthesis, and biological evaluation of a novel series of quercetin diacylglucosides as potent anti-MRSA and anti-VRE agents", Bioorganic & Medicinal Chemistry Letters, Pergamon, Elsevier Science, GB, vol. 20, No. 17, Sep. 1, 2010, pp. 5349-5352.

Abugafar M. L. Hossion et al: "Quercetin Diacylglycoside Analogues Showing Dual Inhibition of DNA Gyrase and Topoisomerase IV as Novel Antibacterial Agents", Journal of Medicinal Chemistry, vol. 54, No. 11, Jun. 9, 2011, pp. 3686-3703.

* cited by examiner

FLAVANONE DERIVATIVE

TECHNICAL FIELD

The present invention relates to a novel flavanone derivative, and more specifically, to a novel flavanone derivative useful as a synthetic antimicrobial agent.

This application claims priority from Japanese Patent Application No. 2009-178718, which is incorporated herein by reference.

BACKGROUND ART

In recent years, bacteria resistant to penicillin, cephalosporin, and the like have emerged, and infection with multiresistant and methicillin-resistant *Staphylococcus aureus* (MRSA) causes severe problems in clinical fields. As typical drugs for treating and preventing MRSA, there are used vancomycin, teicoplanin, arbekacin, linezolid, and the like. In particular, a glycopeptide antibiotic such as vancomycin is generally used as for treatment of MRSA an antibacterial agent because there are few bacteria resistant to the antibiotic. However, vancomycin intermediate-resistant *Staphylococcus aureus* (VISA) has been discovered in 1996, and emergence of vancomycin-resistant enterococci (VRE) and vancomycin-resistant *Staphylococcus aureus* (VRSA) has been reported heretofore. Therefore, the agent needs to be used with great care. Accordingly, development of a novel compound having sufficient effects on drug-resistant bacteria as well has been desired.

Many studies have been made on antibacterial agents for MRSA. A certain kind of flavanone derivative extracted from a bay tree has been reported to show an antibacterial activity against MRSA (Non Patent Literature 1). In addition, comparison of antibacterial activities of phytochemical flavanone derivatives against MRSA has been reported (Non Patent Literature 2). However, there is no report about an effect on a microorganism having stronger resistance such as VRSA, and development of a more effective novel compound has been desired.

CITATION LIST

Non Patent Literature

[NPL 1] Biol. Pharm. Bull., 31(9), 1794-1797 (2008) [NPL 2] J. Ethnopharmacology, 50, 27-34 (1996)

SUMMARY OF INVENTION

Technical Problem

An object of the present invention is to provide a novel compound having an antimicrobial effect. More specifically, an object of the present invention is to provide a novel synthetic antimicrobial agent capable of effectively acting on various resistant bacteria such as VSSA, MRSA, VISA, VRE, and VRSA.

Solution to Problem

The inventors of the present invention have made intensive studies to achieve the object by synthesizing a further novel compound from a flavanone derivative, and as a result, have found that a novel flavanone derivative having a six-membered monosaccharide derivative, specifically, a glucose derivative or a galactose derivative is capable of effectively acting on the bacteria. Thus, the inventors have completed the present invention.

That is, the present invention includes the following.

1. A flavanone derivative, which is represented by the following general formula (I), or a pharmaceutically acceptable salt thereof.

[Chem. 1]

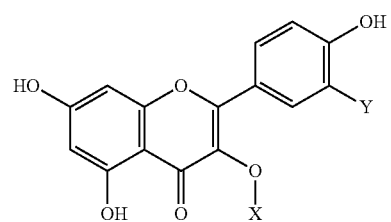

Formula (I)

(In the formula: X represents a six-membered monosaccharide derivative; and Y represents hydrogen or a hydroxyl group.)

2. A flavanone derivative or a pharmaceutically acceptable salt thereof according to item 1, in which the six-membered monosaccharide derivative is a glucose derivative or a galactose derivative.

3. A flavanone derivative or a pharmaceutically acceptable salt thereof according to claim 1 or 2, in which the flavanone derivative is represented by the following general formula (II).

[Chem. 2]

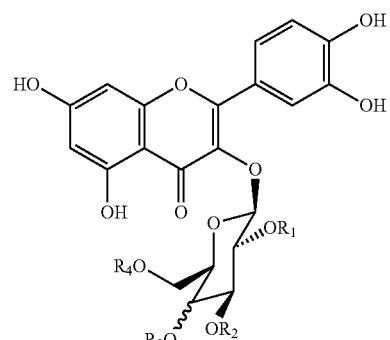

Formula (II)

(In the formula: $R_1$, $R_2$, $R_3$, and $R_4$ each independently represent a hydrogen atom or $R_5$—Z; $R_5$ is selected from the group consisting of an acyl group, an alkyl group, an alkenyl group, and an alkynyl group; and Z is selected from the group consisting of a hydrogen atom, a phenyl group which may have a substituent, a cycloalkyl group which may have a substituent, a heterocyclic group which may have a substituent, a hydroxyl group, an amino group, a cyano group, a halogen, a methyl group, a carboxyl group, a carboxyl group derivative in which a carbonyl oxygen atom may be substituted by a hydroxyimino group or the like, a carboxyl group derivative in which a hydroxy group may be substituted by a hydroxyamino group or the like, a formyl group, a thiol group, a hydrazino group, an ether, a sulfide, an ester, a lactone, and a lactam.)

4. A flavanone derivative or a pharmaceutically acceptable salt thereof according to claim 3, in which in the compound represented by the general formula (II): $R_1$, $R_2$, $R_3$, and $R_4$ each independently represent a hydrogen atom or $R_5$—Z; $R_5$ represents an acyl group; and Z represents a hydrogen atom or a phenyl group which may have a substituent.

5. A flavanone derivative or a pharmaceutically acceptable salt thereof according to claim 4, in which the flavanone derivative is represented by any one of the following formulae (III) to (V).

[Chem. 3]

Formula (III)

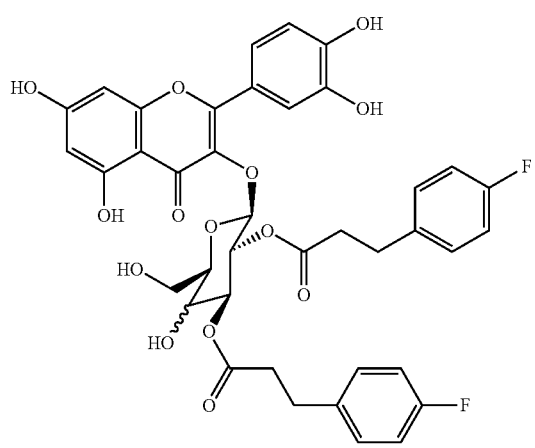

[Chem. 4]

Formula (IV)

[Chem. 5]

Formula (V)

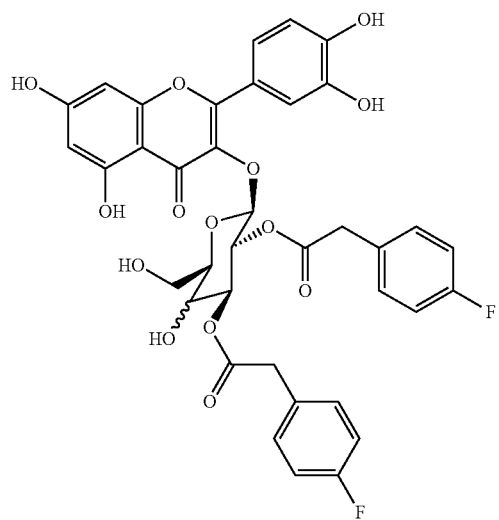

Glucose derivative; ⋯⋯OH
Galactose derivative; ━OH

6. A novel synthetic antimicrobial agent, including the flavanone derivative or the pharmaceutically acceptable salt thereof according to any one claims 1 to 5.

7. A novel synthetic antibacterial agent according to claim 6, in which the novel synthetic antimicrobial agent has an antibacterial effect on *Staphylococcus aureus*.

8. A novel synthetic antimicrobial agent according to claim 7, in which the *Staphylococcus aureus* includes methicillin-resistant *Staphylococcus aureus* and/or vancomycin-resistant *Staphylococcus aureus*.

9. A synthetic antimicrobial agent, including the novel synthetic antimicrobial agent according to any one of claims 6 to 8 as an active ingredient.

Advantageous Effects of Invention

The novel flavanone derivative of the present invention has been found to exhibit a strong antibacterial activity against not only MRSA but also VRSA. Therefore, the novel flavanone derivative of the present invention has a function as an excellent synthetic antimicrobial agent, and hence can be used as a synthetic antimicrobial agent for a medicine, a disinfectant, or the like containing the flavanone derivative as an active ingredient.

DESCRIPTION OF EMBODIMENTS

Figure 1:
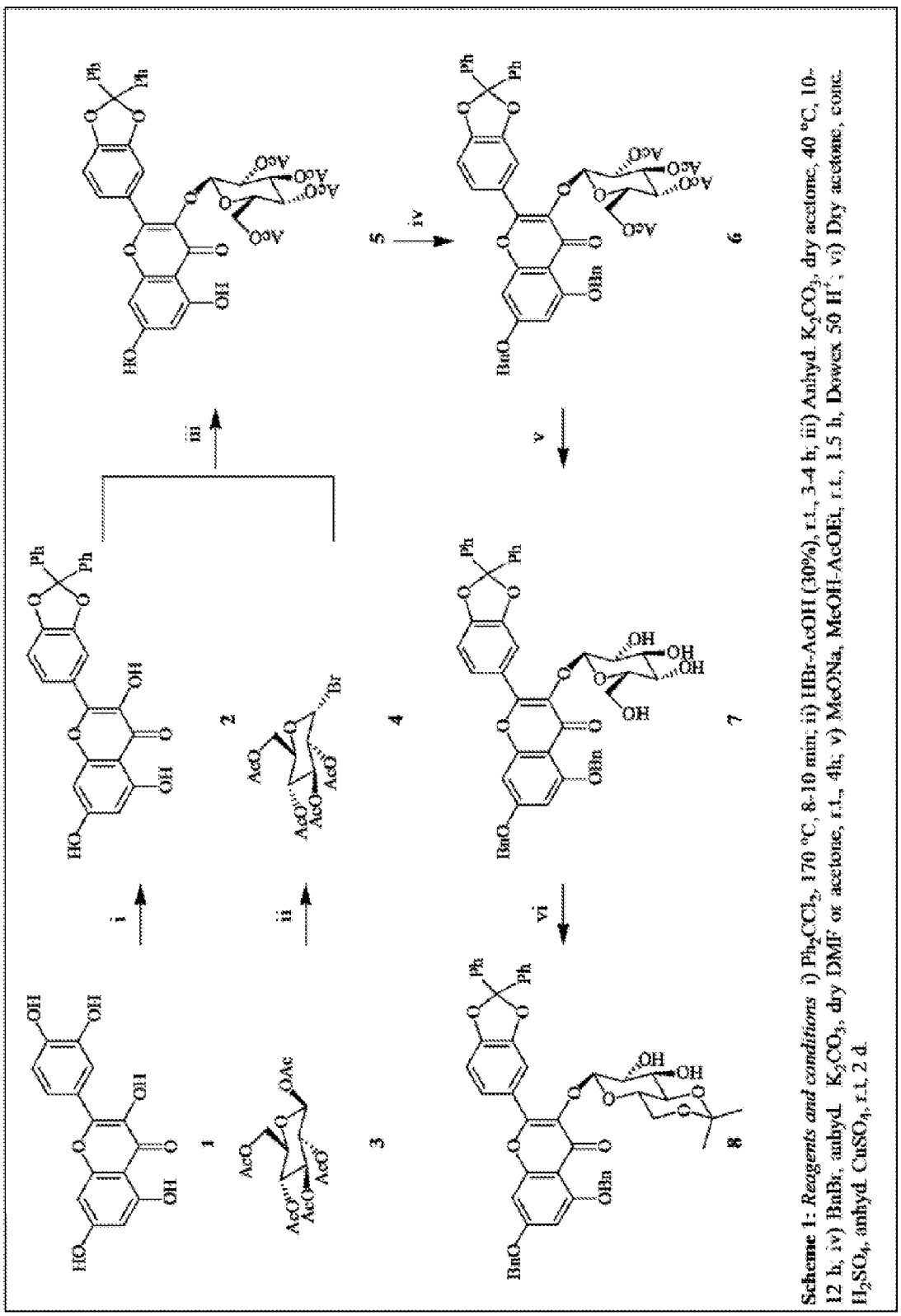
FIG. 1 is a diagram illustrating a synthesis scheme of intermediates 1 to 8 in synthesis of a novel flavanone derivative of the present invention (Examples 1-1 to 1-6).

A novel flavanone derivative of the present invention includes a flavanone derivative, which is represented by the following general formula (I), or a pharmaceutically acceptable salt thereof.

[Chem. 1]

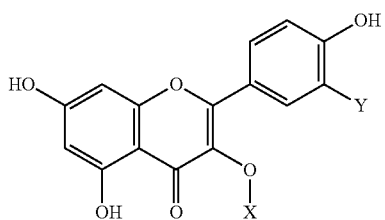

Formula (I)

(In the formula: X represents a six-membered monosaccharide derivative; and Y represents hydrogen or a hydroxyl group.)

The six-membered monosaccharide derivative is preferably a glucose derivative or a galactose derivative.

More specifically, the novel flavanone derivative includes a flavanone derivative or a pharmaceutically acceptable salt thereof, in which the flavanone derivative is represented by the following general formula (II).

[Chem. 2]

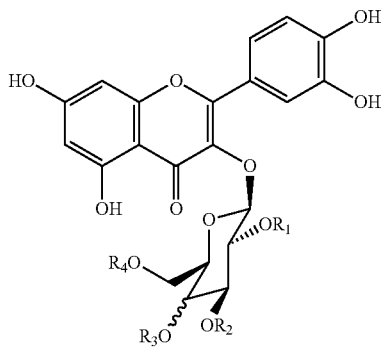

Formula (II)

Glucose derivative: ⋯⋯OR$_3$
Galactose derivative: ▬OR$_3$ (In the formula: $R_1$, $R_2$, $R_3$, and $R_4$ each independently represent a hydrogen atom or $R_5$—Z; $R_5$ is selected from the group consisting of an acyl group, an alkyl group, an alkenyl group, and an alkynyl group; and Z is selected from the group consisting of a hydrogen atom, a phenyl group which may have a substituent, a cycloalkyl group which may have a substituent, a heterocyclic group which may have a substituent, a hydroxyl group, an amino group, a cyano group, a halogen, a methyl group, a carboxyl group, a carboxyl group derivative in which a carbonyl oxygen atom may be substituted by a hydroxyimino group or the like, a carboxyl group derivative in which a hydroxy group may be substituted by a hydroxyamino group or the like, a formyl group, a thiol group, a hydrazino group, an ether, a sulfide, an ester, a lactone, and a lactam.)

Further, in the formula, the substituent in each of the phenyl group which may have a substituent, the cycloalkyl group which may have a substituent, and the heterocyclic group which may have a substituent is selected from the group consisting of an acyl group, an alkyl group, an alkenyl group, an alkynyl group, an alkyloxy group, and a benzyloxy group, a hydroxyl group, an amino group, a cyano group, a halogen, and a carboxyl group.

The alkyl is exemplified by a $C_1$ to $C_{20}$ linear or branched alkyl group, and is preferably a $C_1$ to $C_{10}$ alkyl group, particularly preferably a $C_1$ to $C_6$ alkyl group. The alkenyl is exemplified by a $C_2$ to $C_{20}$ linear or branched alkenyl group, and is preferably a $C_2$ to $C_{10}$ alkenyl group, particularly preferably a $C_2$ to $C_6$ alkenyl group. The alkynyl is exemplified by a $C_2$ to $C_{20}$ linear or branched alkynyl group, and is preferably a $C_2$ to $C_{10}$ alkynyl group, particularly preferably a $C_2$ to $C_6$ alkynyl group. The acyl group is exemplified by a $C_1$ to $C_9$ acyl group, and is preferably a $C_1$ to $C_6$ acyl group. The cycloalkyl group is exemplified by a $C_3$ to $C_{10}$ cycloalkyl group. The heterocycle is exemplified by a five- to ten-membered heterocyclic group containing a heteroatom selected from nitrogen, sulfur, and oxygen.

Examples of the halogen include fluorine, chlorine, bromine, and iodine.

More specifically, the novel flavanone derivative includes a flavanone derivative or a pharmaceutically acceptable salt thereof, in which the flavanone derivative is represented by any one of the following formulae (III) to (V).

[Chem. 3]

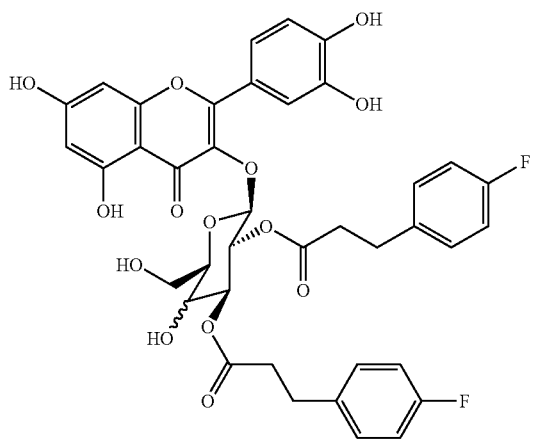

Formula (III)

[Chem. 4]

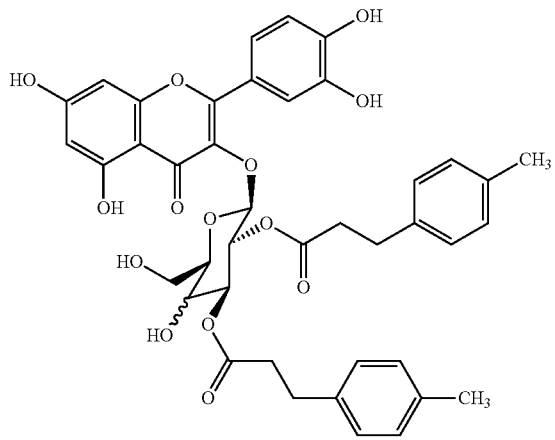

Formula (IV)

[Chem. 5]

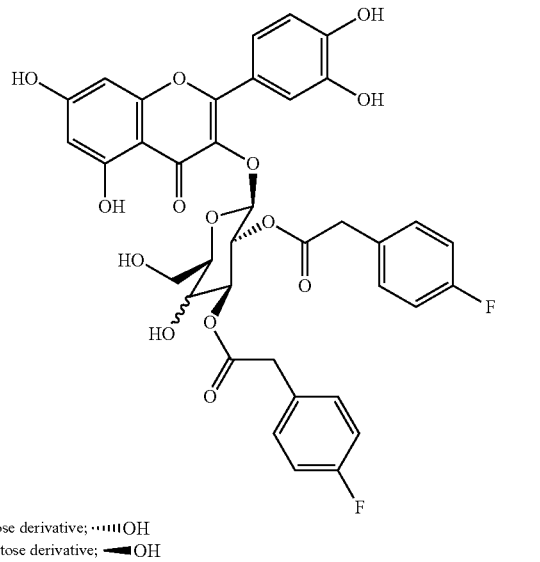

Formula (V)

Glucose derivative; ⋯⋯ＯＨ
Galactose derivative; ━ ＯＨ

In the present invention, in the case where the flavanone derivative or the pharmaceutically acceptable salt thereof, in which the flavanone derivative is represented by the general formula (I) or (II), has isomers (such as an optical isomer, a geometric isomer, and a tautomer) and the like, the flavanone derivative or the pharmaceutically acceptable salt thereof includes the isomers, and includes a solvate, a hydrate, and crystals having various shapes. Specific examples thereof include the flavanone derivative or the pharmaceutically acceptable salt thereof, in which the flavanone derivative is represented by any one of the formulae (III) to (V).

In the present invention, the pharmaceutically acceptable salt includes general pharmacologically and pharmaceutically acceptable salts. Specific examples thereof include the following salts.

There are given, as basic addition salts: alkali metal salts such as a sodium salt and a potassium salt; alkaline earth metal salts such as a calcium salt and a magnesium salt; for example, an ammonium salt; aliphatic amine salts such as a trimethylamine salt, a triethylamine salt, a dicyclohexylamine salt, an ethanolamine salt, a diethanolamine salt, a triethanolamine salt, and a procaine salt; aralkylamine salts such as an N,N-dibenzylethylenediamine salt; heterocyclic aromatic amine salts such as a pyridine salt, a picoline salt, a quinoline salt, and an isoquinoline salt; quaternary ammonium salts such as a tetramethylammonium, salt, a tetraethylammonium salt, a benzyltrimethylammonium salt, a benzyltriethylammonium salt, a benzyltributylammonium salt, a methyltrioctylammonium salt, and a tetrabutylammonium salt; basic amino acid salts such as an arginine salt and a lysine salt; and the like.

There may be given, as acid addition salts: inorganic acid salts such as a hydrochloride, a sulfate, a nitrate, a phosphate, a carbonate, a hydrogen carbonate, and a perchlorate; organic acid salts such as an acetate, a propionate, a lactate, a maleate, a fumarate, a tartarate, a malate, a citrate, and an ascorbate; sulfonates such as a methanesulfonate, an isethionate, a benzenesulfonate, and a p-toluenesulfonate; acidic amino acid salts such as an aspartate and a glutamate; and the like.

A preparation method for the novel flavanone derivative in the present invention may be carried out with reference to methods described in Examples. All the compounds included in the scope of the present invention can be produced by appropriately modifying or altering, for example, starting materials, reagents, and reaction conditions used in the preparation methods. In addition, the novel flavanone derivative of the present invention and synthesis methods are not limited to the methods specifically described above.

The novel synthetic antimicrobial agent of the present invention includes any one of the novel flavanone derivatives or the pharmaceutically acceptable salts thereof described above. The novel synthetic antimicrobial agent of the present invention includes a flavanone derivative derived from a natural product as a basic skeleton, and includes a flavanone derivative synthesized by chemical modification of the derivative or a pharmaceutically acceptable salt thereof. The synthetic antimicrobial agent includes an agent, having an antimicrobial activity against a bacterium or a fungus, and the effect of the novel synthetic antimicrobial agent of the present invention is preferably an antibacterial effect against a bacterium. For example, the agent has an antibacterial effect on a Gram-positive bacterium such as *Staphylococcus aureus*. Examples of the *Staphylococcus aureus* include methicillin-resistant *Staphylococcus aureus* (MRSA) and/or vancomycin-resistant *Staphylococcus aureus* (VRSA), but the novel synthetic antimicrobial agent of the present invention effectively acts on bacteria other than the methicillin- or vancomycin-resistant bacteria.

The novel synthetic antimicrobial agent of the present invention may be formulated together with a pharmaceutically acceptable carrier depending on its purpose such as a medicine or a disinfectant, and used as an antimicrobial agent. A medicine containing the novel flavanone derivative of the present invention as an active ingredient may be used as, for example, an antibiotic or an antimicrobial agent. As mentioned above, the novel flavanone derivative of the present invention has an excellent antibacterial effect on, for example, MRSA or VRSA. Therefore, in addition to medicinal use, the agent may be mixed in facilities or equipment and body cleaning agents or disinfectants in medical-related organizations, nursing homes, ordinary households, and other business places, or the equipment and the like may be directly impregnated or coated with the agent.

In the case where the synthetic antimicrobial agent of the present invention is used as a medicine for prevention or treatment of infection with the bacteria or fungi, the agent may be orally or parenterally administered at an effective dose. The dose may be appropriately determined depending on the administration route or administration method. For example, in the case of oral administration, the agent may be used so that the amount of the active ingredient falls within a range of 0.01 to 1,000 mg per day per adult human.

The dosage form suitable for oral administration is a solid formulation or a liquid formulation, and examples thereof include a tablet, a capsule, a powder, a fine granule, a granule, a solution, and a syrup. Meanwhile, examples of the dosage form suitable for parenteral administration include an injection, a drop, a suppository, an inhalant, an ointment, a cream, and a patch.

In the case where the tablet which is one of the solid formulations for oral administration is prepared, there may be used an additive such as: an excipient such as lactose, starch, calcium carbonate, crystalline cellulose, or silicic acid; a binder such as carboxymethyl cellulose, methyl cellulose, calcium phosphate, or polyvinylpyrrolidone; a disintegrant such as sodium alginate, sodium bicarbonate, sodium lauryl sulfate, or stearic acid monoglyceride; a lubricant such as glycerin; an absorbent such as kaolin or colloidal silica; or a lubricant such as talc or granular boric acid in accordance with a conventional method.

The pill, powder, or granule may also be formulated in accordance with a conventional method in the same way as above using an additive. The liquid formulations such as the solution and suspension may also be formulated in accordance with a conventional method. Examples of the carrier include: a glycerol ester such as tricaprylin, triacetin, or an iodinated poppy-seed oil fatty acid ester; water; an alcohol such as ethanol; and an oily base such as liquid paraffin, coconut oil, soybean oil, sesame oil, or corn oil. The powder, granule, and liquid formulations may be covered with capsules made of gelatin or the like.

The dosage form of a medicament for transdermal administration is exemplified by an ointment, a cream, a lotion, and a solution. As the base of the ointment, there are given: fatty oils such as castor oil, olive oil, sesame oil, and safflower oil; lanolin; white, yellow, or hydrophilic petrolatum; wax; higher alcohols such as oleyl alcohol, isostearyl alcohol, octyldodecanol, and hexadecanol; glycols such as glycerin, diglycerin, ethylene glycol, propylene glycol, sorbitol, and 1,3-butanediol; and the like. Further, ethanol, dimethyl sulfoxide, polyethylene glycol, or the like may be used as a solubilizer. Further, there may also be used as required: a preservative such as a p-oxybenzoic acid ester, sodium benzoate, salicylic acid, sorbic acid, or boric acid; an antioxidant such as butylhydroxyanisole or dibutylhydroxytoluene; or the like.

In addition, in order to promote transdermal absorption, an absorption promoter such as diisopropyl adipate, diethyl sebacate, ethyl caproate, or ethyl laurate may be added. Further, in order to stabilize the compound of the present invention, the compound may form a clathrate together with α-, β-, or γ-cyclodextrin or methylated cyclodextrin before use.

The ointment may be produced by a usual method. The cream preferably has a form of an oil-in-water cream to stabilize the compound of the present invention. Further, as a base thereof, a fatty oil, a higher alcohol, a glycol, or the like is used as mentioned above, and an emulsifier such as diethylene glycol, propylene glycol, a sorbitan mono-fatty acid ester, polysorbate 80, or sodium lauryl sulfate is used. Further, if necessary, a preservative, an antioxidant, or the like may be added as mentioned above. In addition, as is the case with the ointment, the cream may be used as a clathrate of cyclodextrin or methylated cyclodextrin before use. The cream can be produced by a usual method.

Examples of the lotion include a suspension-type lotion, an emulsion-type lotion, and a solution-type lotion. The suspension-type lotion can be obtained by using a suspending agent such as sodium alginate, tragacanth, or sodium carboxymethylcellulose and optionally adding an antioxidant, a preservative, or the like. The emulsion-type lotion can be obtained by using an emulsifier such as a sorbitan mono-fatty acid ester, polysorbate 80, or sodium lauryl sulfate by a usual method. The solution-type lotion is preferably an alcohol-type lotion and can be obtained by using an alcohol such as ethanol by a usual method. The solution can be obtained by dissolving the compound of the present invention in an alcohol solution such as ethanol and optionally adding an antioxidant, a preservative, or the like.

In addition to such dosage forms, dosage forms such as a paste, a cataplasm, and an aerosol may be employed. Such formulations can be produced by usual methods.

A formulation to be administered by injection is provided as a sterile aqueous or non-water-soluble solution, suspension, or emulsifier. The non-water-soluble solution or suspension includes propylene glycol, polyethylene glycol, or a vegetable oil such as olive oil, ethyl oleate, or an injectable organic ester such as an iodinated poppy-seed oil fatty acid ester as a pharmaceutically acceptable carrier. Such formulation may further contain an auxiliary agent such as a preservative, a wetting agent, an emulsifier, a dispersant, or a stabilizer, and may be a sustained-release formulation. The solution, suspension, and emulsifier can be sterilized by an appropriate treatment such as filtration through a bacteria-retaining filter, blending of a disinfectant, or irradiation. Further, a sterile solid formulation may be produced and used after dissolving the formulation in sterile water or a sterile solvent for injection immediately before use.

The pharmaceutically acceptable carrier in this description may include another additive which is appropriately selected, such as an auxiliary agent, a fragrance, a tonicity agent, a pH adjuster, a stabilizer, a spray, a pressure-sensitive adhesive, or a preservative, which is usually used if necessary.

EXAMPLES

Hereinafter, in order to gain further understanding of the present invention, the novel flavanone derivative of the present invention is described specifically by showing synthesis methods for and properties of intermediates and final compounds in Examples and by showing activities of the resultant final compounds in Experimental Examples, but the scope of the present invention is not limited to the following examples.

Figure 2:
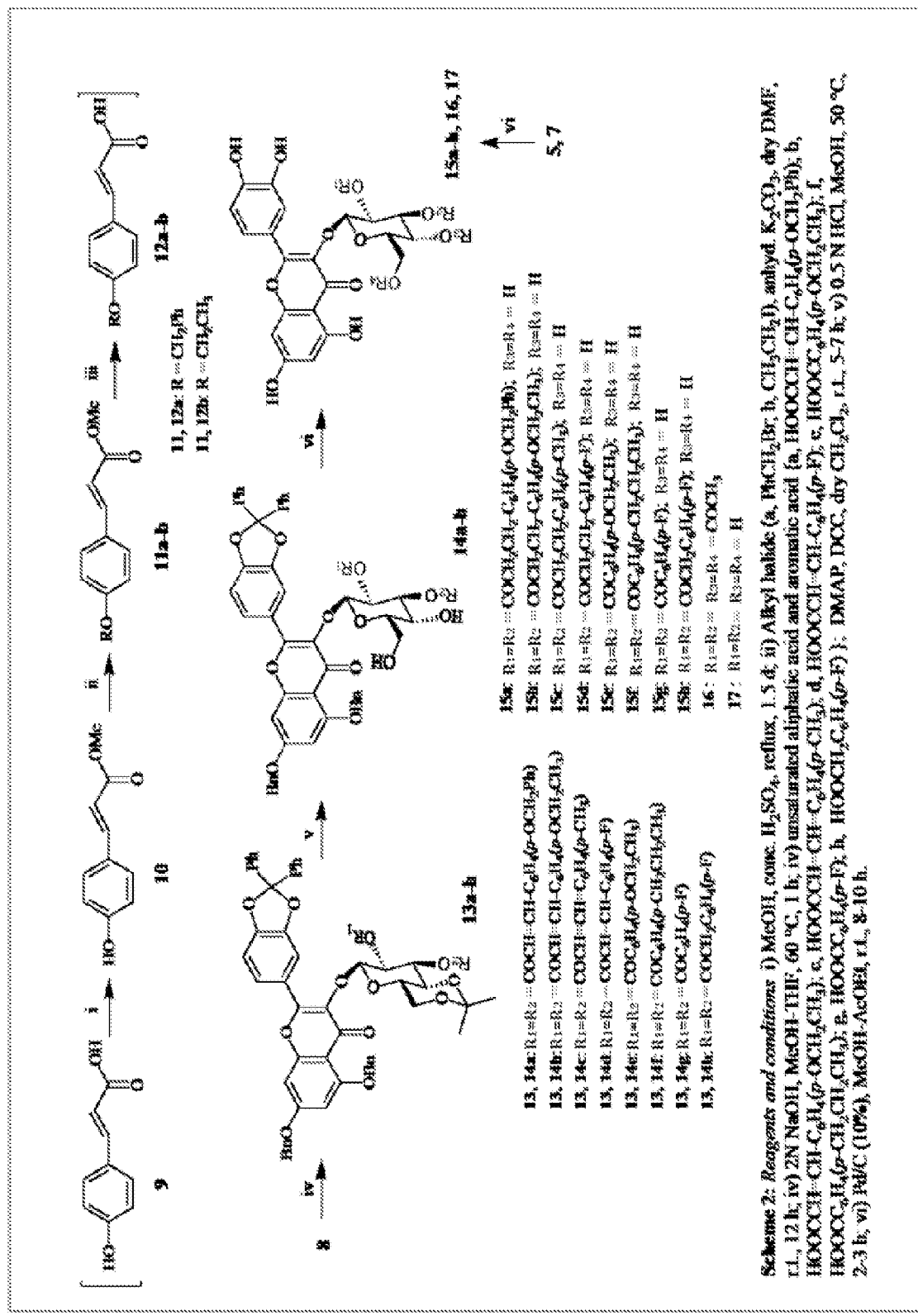
FIG. 2 is a diagram illustrating a synthesis scheme of an intermediate 9 to a final compound in synthesis of a novel flavanone derivative (glucose derivative) of the present invention (Examples 1-7 to 1-12).
Figure 3:
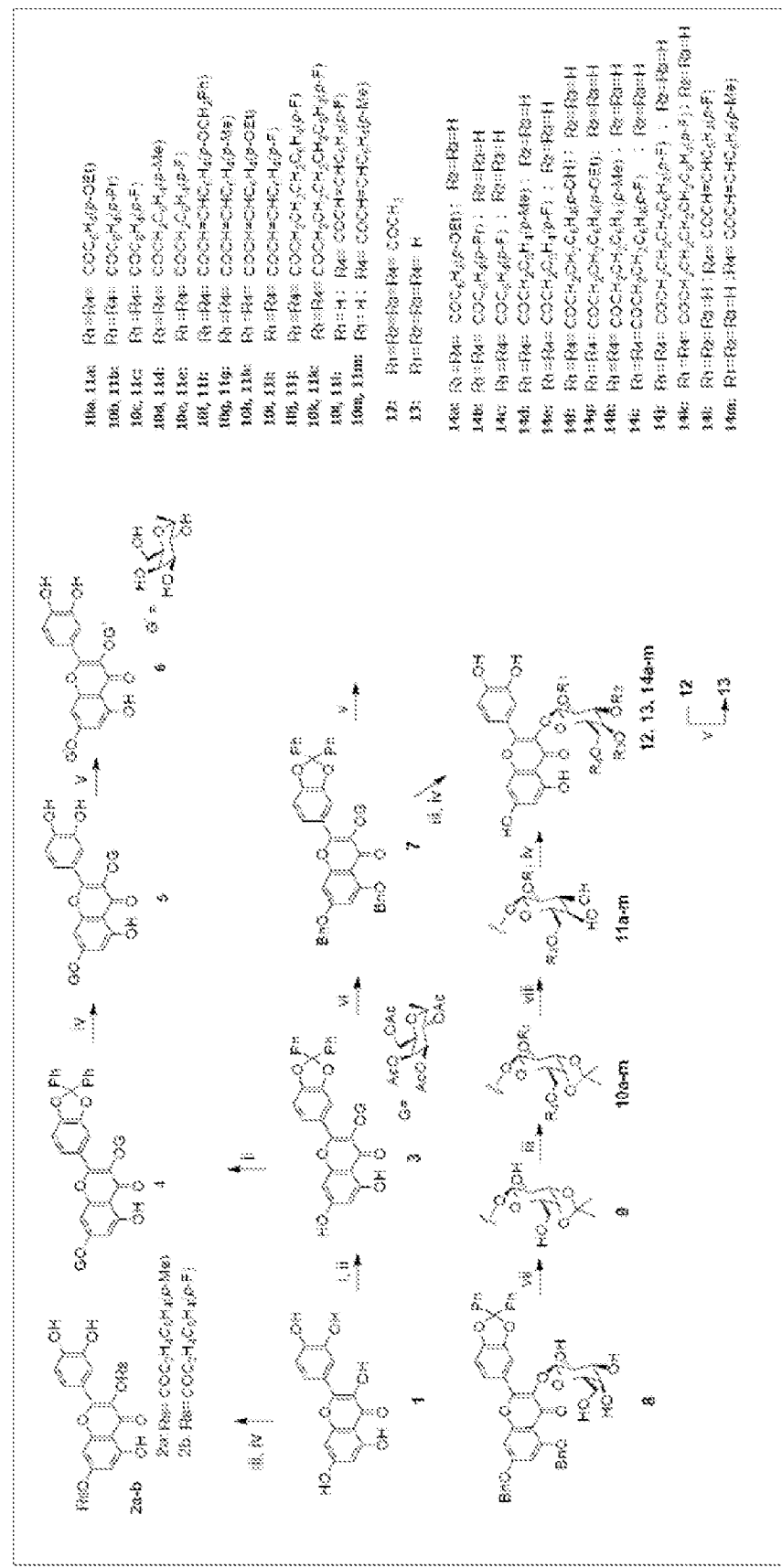
FIG. 3 is a diagram illustrating a synthesis scheme to a final compound in synthesis of a novel flavanone derivative (galactose derivative) of the present invention (Examples 2-1 to 2-7).

It should be noted that FIGS. 1 and 2 illustrate synthesis schemes of synthesis products of a glucose derivative (Example 1), and FIG. 3 illustrates a synthesis scheme of synthesis products of a galactose derivative (Example 2). It should be noted that the numbers of the compounds shown in FIGS. 1 to 3 overlap, but the compounds are specified in the respective figures.

The properties of the synthesis products were measured by the following methods. Melting points were measured using a Yanaco micro melting point apparatus, and correction was not carried out. IR spectra were measured by a KBr method using a JASCO FT/IR-350 spectrophotometer. Mass spectra were measured at 70 eV by a FAB method using VG-70SE. As a matrix, 3-nitrobenzyl alcohol was used. $^1$H NMR and $^{13}$C NMR spectra were measured using VXR 300, VXR 500, or VXR 600 ($^1$H: 300 MHz, 500 MHz, 600 MHz, $^{13}$C: 150 MHz). The chemical shift of $^1$H NMR is shown by ppm based on TMS in CDCl$_3$ or DMSO (0.00 ppm), while the chemical shift of $^{13}$C is shown by ppm based on a signal of DMSO used as a solution. The coupling constant (J value) is shown by Hz. The elemental analysis was performed using Yanaco CHN Corder MT-5. All reagents were commercially available products and used immediately after opening, and further purification of the reagents was not carried out. The progress of reactions was followed by TLC (silica gel 60 F$_{254}$ manufactured by Merck & Co., Inc. or 70 FM plate manufactured by Wako Pure Chemical Industries, Ltd.). Flash column chromatography was carried out using silica gel 60 (spherical shape, 0.063 to 0.200 mm, Kanto Chemical Co. Inc.). The reaction temperature was adjusted based on the temperature of an oil bath. Dry DMF was dried using 4 angstrom molecular sieves and distilled before use.

Example 1-1

Synthesis of Intermediate 2 for Glucose Derivative (FIG. 1)

2-(2,2-Diphenylbenzo[d][1,3]dioxol-5-yl)-3,5,7-trihydroxy-4H-chromen-4-one (2)

A mixture of a compound 1 (quercetin, 1 g, 3 mmol) and $Ph_2CCl_2$ (1.7 mL, 8.9 mmol) was stirred at 170° C. for 7 to 8 minutes, and an oily composition was dissolved in AcOEt (3 ml) in as small an amount as possible. Further, the solution was added to n-hexane (20 mL), and a gray solid precipitated was separated by filtration. The resultant gray solid was subjected to silica gel flash column chromatography, and a yellow solid 2 (0.62 g, 40%) was obtained from a fraction eluted with AcOEt:n-hexane (1:4, v/v).

Melting point (m.p.) 238-239° C. (lit. 239-240° C.). $R_f$=0.15 (AcOEt:n-hexane (1:4, v/v)). IR (KBr) cm$^{-1}$; 1600 (C=C), 1638 (C=O).

$^1$HNMR (DMSO-$d_6$, 300 MHz) δ 6.20 (d, $^4$J=1.8 Hz, 1H, 8-H), 6.46 (d, $^4$J=1.8 Hz, 1H, 6-H), 7.21 (d, J=8.1 Hz, 1H, 3'-H), 7.44-7.50 (m, 6H, Ar—H), 7.54-7.59 (m, 4H, Ar—H), 7.59-7.82 (m, 2H, 7.79-7.82 (m, 2H, 2'-H, 6'-H), 9.63 [s, 1H, 3-OH (exchangeable with $D_2O$)], 10.81 [s, 1H, 7-OH (exchangeable with $D_2O$)], 12.37 [s, 1H, 5-OH (exchangeable with $D_2O$)].

Example 1-2

Synthesis of Intermediate 4 for Glucose Derivative (FIG. 1)

Acetobromo-α-D-glucose (4)

β-D-Glucose pentaacetate (2.5 g, 6.41 mmol) was added to HBr-AcOH (30%) with shaking. The reaction mixture was stirred at room temperature for 2 hours. The resultant reaction mixture was diluted with $CHCl_3$ (50 mL), and the mixture was poured into ice water (15 mL). The chloroform layer was separated into an aqueous layer and a chloroform extraction layer (2×20 mL of $CHCl_3$). The chloroform extraction layer was combined with the chloroform layer, and the mixture was then washed with water and dried over $MgSO_4$, to thereby obtain acetobromo-α-D-glucose (4). The solvent was removed under reduced pressure, and the residue was recrystallized from a mixed solution of AcOEt and n-hexane, to thereby obtain a colorless needles 4 (2.23 g, 85%).

Melting point (m.p.) 89-90° C. (lit. 88-89° C.). $R_f$=0.25 (AcOEt:n-hexane, 1:2, v/v).

$^1$HNMR (CDCl$_3$, 300 MHz) δ 2.04, 2.06, 2.10, and 2.11 (each s, 12H, 4×COCH$_3$), 4.13 (br d, J$_{gem}$=10.5 Hz, 1H, 6'-H$_b$), 4.27-4.37 (m, 2H, 5',6'-H$_a$), 4.84 (dd, J$_{3',4'}$=9.6 Hz, J$_{2',3'}$=9.9 Hz, 1H, 3'-H), 5.16 (t, J$_{2',3'}$=9.9 Hz, 1H, 2'-H), 5.56 (t, J$_{3',4'}$=9.6 Hz, 1H, 4'-H), 6.61 (d, J$_{1'',2''}$=4.2 Hz, 1H, 1''-H).

Example 1-3

Synthesis of Intermediate 5 for Glucose Derivative (FIG. 1)

2-(2,2-Diphenylbenzo[d][1,3]dioxol-5-yl)-5,7-dihydroxy-3-β-D-tetraacetylglucosyl-4H-thromen-4-one (5)

A mixed solution of the intermediate 2 (0.3 g, 0.64 mmol) was allowed to react under argon together with acetobromo-α-D-glucose (0.4 g, 0.97 mmol), anhydrous $K_2CO_3$ (0.12 g, 0.9 mmol) in dry acetone (7 mL) at 40° C. for 12 hours. The resultant product was added to $H_2O$ (15 mL). A pale-yellow solid was obtained by filtration. The collected crude product was eluted by flash column chromatography using silica gel together with AcOEt and n-hexane (2:4), to thereby obtain a colorless powdery compound 5 (0.16 g, 40%).

Melting point (m.p.) 126-127° C. $R_f$=0.21 (AcOEt:n-hexane, 1:2, v/v). IR (KBr) cm$^{-1}$; 1610 (C=C), 1638 and 1750 (C=O).

$^1$H NMR (CDCl$_3$, 300 MHz) δ 1.68, 2.01, 2.04, and 2.11 (each s, 12H, 4×COCH$_3$), 3.67 (br d, J$_{4'',5''}$=9.6 Hz, 1H, 5''-H), 3.88-3.93 (dd, J$_{5'',6''Hb}$=3.6 Hz, J$_{gem}$=12.0 Hz, 1H, 6''-H$_b$), 4.13 (br d, J$_{gem}$=12.0 Hz, 1H, 6''-H.), 5.09 (t, J$_{4'',5''}$=9.6 Hz, 4''-H), 5.20-5.33 (m, 2H, 2''-H, 3''-H), 5.63 (d, J$_{1'',2''}$=7.5 Hz, 1H, 1''-H), 6.24 (br s, 1H, Ar—H, 8-H), 6.31 (br s, 1H, Ar—H, 6-H), 6.60 [br s, 1H, 7-OH (exchangeable with $D_2O$)], 6.96 (d, J=8.1 Hz, 1H, Ar—H, 3'-H), 7.26-7.58 (m, 6H, Ar—H), 7.58-7.67 (m, 6H, Ar—H), 12.46 [s, 1H, 5-OH (exchangeable with $D_2O$)]. MS (FAB, 3-nitrobenzyl alcohol was used as matrix) m/z; 797 ([MH]$^+$).

Example 1-4

Synthesis of Intermediate 6 for Glucose Derivative (FIG. 1)

5,7-Dibenzyloxy-2-(2,2-diphenylbenzo[d][1,3]dioxol-5-yl)-3-β-D-tetraacetylglucosyl-4H-chromen-4-one (6)

A mixed solution of the intermediate 5 (1 g, 1.26 mmol) and anhydrous $K_2CO_3$ (3 mmol) were added to dry DMF (10 mL), and benzyl bromide (3 mmol) was added at room temperature. The mixture was stirred at room temperature for 10 hours. After completion of the reaction, cold water was added thereto. The resultant solid was separated by filtration, washed with $H_2O$, and dried. The resultant crude product was crystallized from AcOEt and n-hexane, to thereby obtain a colorless crystalline powder 6 (1.12 g, 890).

Melting point (m.p.) 237-239° C. $R_f$=0.32 (AcOEt:n-hexane, 1:2, v/v). IR (KBr) cm$^{-1}$; 1610 (C=C), 1640 and 1748 (C=O).

$^1$HNMR (CDCl$_3$, 300 MHz) δ 1.73, 2.01, 2.03, and 2.13 (each s, each 3H, 4×COCH$_3$), 3.61-3.65 (m, 1H, 5''-H), 5.08 and 3.97 (each s, 4H, 2×CH$_2$—O), 5.11-5.28 (m, 5H, 2''-H, 3''-H, 4''-H, 6''-H), 5.77 (d, J$_{1'',2''}$=7.5 Hz, 1H, 1''-H), 6.45 (d, $^4$J=2.4 Hz, 1H, 8-H), 6.56 (d, $^4$J=2.4 Hz, 1H, 6-H), 6.96 (d, J=8.4 Hz, 1H, 3'-H), 7.29-7.43 (m, 14H, 7.56-7.68 (m, 8H, Ar—H).

Example 1-5

Synthesis of Intermediate 7 for Glucose Derivative (FIG. 1)

5,7-Dibenzyloxy-2-(3',4'-dihydroxyphenyl)-3-β-D-glucosyl-4H-chromen-4-one (7)

NaOMe (0.05 g, 0.90 mmol) was added to a solution of the compound 6 (0.50 g, 0.51 mmol) dissolved in AcOEt:MeOH (1:1, 20 mL), and the mixture was stirred at room temperature (r.t.) for 30 minutes. After completion of the reaction, the solution was passed through a Dowex™ 50 (H$^+$) ion-exchange resin column and neutralized. The resultant was concentrated and filtered, to thereby obtain a colorless powdery compound 7 (0.48 g, 80%).

Melting point (m.p.) 245-246° C. $R_f$=0.19 (AcOEt). IR (KBr) cm$^{-1}$; 1600 (C=C), 1620 (C=O), 3410 (OH).

$^1$H NMR (DMSO-d$_6$, 300 MHz) δ 3.09-3.25 (m, 5H, 3"-H, 4"-H, 6"-H, 5"-H), 3.53-3.58 (m, 1H, 2"-H), 4.23 [t, J=5.1 Hz, 1H, 6"-OH (exchangeable with D$_2$O)], 5.07 [d, J=4.5 Hz, 1H, 3"-OH (exchangeable with D$_2$O)], 4.93 [d, J=4.8 Hz, 1H, 4"-H (exchangeable with D$_2$O)], 5.22 and 5.24 (each s, each 2H, 2×-CH$_2$—O—), 5.38 (d, J$_{1''',2''}$=7.5 Hz, 1H, 1"-H), 5.52 [d, J=3.9 Hz, 1H, 2"-OH (exchangeable with D$_2$O)], 6.69 (d, $^4$J=2.1 Hz, 1H, 8-H), 6.95 (d, $^4$J=2.1 Hz, 1H, 6-H), 7.16 (d, J=8.1 Hz, 1H, 3'-H), 7.32-7.50 (m, 14H, Ar—H), 7.55-7.60 (m, 6H, Ar—H), 7.80-7.86 (m, 2H, Ar—H). Anal. Calcd for C$_{48}$H$_{40}$O$_{12}$: C, 71.28; H, 4.98. Found: C, 71.68; H, 4.86.

Example 1-6

Synthesis of Intermediate 8 for Glucose Derivative (FIG. 1)

5,7-Dibenzyloxy-4",6"-O-isopropylidene-2-(3',4'-dihydroxyphenyl)-3-β-D-glucosyl-4H-chromen-4-one (8)

A mixture of the compound 7, dry acetone (50 mL), and anhydrous copper sulfate (2 g) was added to a 300-mL flask, and concentrated (conc.) H$_2$SO$_4$ (1 drop) was further added. The flask was sealed and allowed to stand at room temperature for 2 days. During this procedure, the reaction mixture was shaken several times. After completion of the reaction, copper sulfate was removed by filtration, and the filtrate was concentrated to 3 mL under reduced pressure. n-Hexane was added to the solution to produce a solid, which was collected by filtration, to thereby obtain a colorless crystalline powder (0.63 g, 60%).

Melting point (m.p.) 206-207° C. $R_f$=0.23 (AcOEt:n-hexane, 1:3, v/v). IR (KBr) cm$^{-1}$; 1600 (C=C), 1620 (C=O), 3405 (OH).

$^1$H NMR (CDCl$_3$, 300 MHz): δ 1.40 and 1.48 (each s, each 3H, 6H, 2×Me), 3.06-3.08 (m, 1H, 5"-H), 3.39-3.72 (m, 5H, 6"-H, 4"-H, 3"-H, 2"-H,), 4.85 (d, J$_{1'',2''}$=7.5 Hz, 1H, 1"-H), 5.10 and 5.24 (each s, each 2H, 2×CH$_2$—O), 6.49 (d, $^4$J=2.4 Hz, 1H, 8-H), 6.59 (d, $^4$J=2.4 Hz, 1H, 6-H), 6.95 (d, J=8.1 Hz, 1H, 3'-H), 7.17-7.94 (m, 14H, Ar—H), 7.55-7.62 (m, 6H, Ar—H), 7.67-7.73 (m, 2H, 2'-H and 6'-H).

$^1$H NMR (DMSO-d$_6$, 600 MHz): δ1.26 and 1.39 (each s, each 3H, 6H, 2×CH$_3$), 3.08-3.13 (ddd, J$_{5',6''Ha}$=5.4 Hz, J$_{4'',5''}$=9.6, J$_{5'',6''Hb}$=4.8 Hz, 1H, 5"-H), 3.39-3.72 (m, 4H, 6"-H$_b$, 4"-H, 3"-H, 2"-H,), 3.53 (dd, J$_{5'',6''Ha}$=5 4 Hz, J$_{gem}$=10.2 Hz, 1H, 6"-H$_a$), 5.23 and 5.24 (each s, each 2H, 2×-CH$_2$—O—), 5.29 [d, J=4.2 Hz, 1H, 3"-OH (exchangeable with D$_2$O)], 5.32 (d, J$_{1'',2''}$=7.2 Hz, 1H, 1"-H), 5.80 [d, J=4.2 Hz, 1H, 2"-OH (exchangeable with D$_2$O)], 6.72 (d, $^4$J=2.4 Hz, 1H, 8-H), 7.00 (d,$^4$J=2.4 Hz, 1H, 6-H), 7.21 (d, J=7.8 Hz, 1H, 3'-H), 7.32-7.49 (m, 14H, Ar—H), 7.56-7.58 (m, 6H, Ar—H), 7.78 (dd, J=8.4 Hz, $^4$J=2.4 Hz, 1H, 6'-H), 7.80 (d, $^4$J=2.4 Hz, 1H, 2'-H). MS (FAB, 3-nitrobenzyl alcohol was used as matrix) m/z; 849 ([MH]$^+$). Anal. Calcd for C$_{51}$H$_{44}$O$_{12}$: C, 72.16; H, 5.22. Found: C, 71.90; H, 5.17.

Example 1-7

Synthesis of Intermediate 10 for Glucose Derivative (FIG. 2)

3-(4-Hydroxyphenyl)methylacrylate (10)

A mixed solution (amixture) of cinnamic acid (5 g, 30.48 mmol) was refluxed for 1.5 days in the presence of dry MeOH (300 mL) and concentrated (conc.) H$_2$SO$_4$ (1 drop). The solution was cooled to room temperature (r.t.) and then evaporated with 30% ammonia water under reduced pressure and neutralized. Finally, the solution was evaporated with EtOH, to thereby obtain a completely dried product. The dried residue was subjected to silica gel column chromatography, to thereby obtain a colorless needle-like product 10 (4.8 g, 88%) from a fraction eluted with AcOEt-n-hexane (1:4, v/v).

Melting point (m.p.) 122-123° C. $R_f$=0.23 (AcOEt:n-hexane, 1:8, v/v). IR (KBr) cm$^{-1}$; 1600 (C=C), 1695 (C=O), 3380 (OH).

$^1$H NMR (CDCl$_3$, 300 MHz): δ 3.81 (s, 3H, O-Me), 5.92 [s, 1H, Ar—OH (exchangeable with D$_2$O)], 6.32 (d, J=15.9 Hz, 1H, Ar—CH=CH—), 6.86 (d, 2H, J=8.4 Hz, Ar—H), 7.42 (d, 2H, J=8.4 Hz, Ar—H), 7.67 (d, J=15.9 Hz, 1H, Ar—CH=CH—).

Example 1-8

Synthesis of Intermediates 11a-b for Glucose Derivative (FIG. 2)

3-(4-Benzyloxy or 4-Ethoxyphenyl)methylacrylate (11a-b)

3-(4-Hydroxyphenyl)methylacrylate (9) (0.18 g, 1 mmol) was mixed with anhydrous K$_2$CO$_3$ (1.5 mmol) and dry DMF (5 mL). Then, an appropriate alkyl halide (1.5 mmol) was added, and the mixture was stirred well at room temperature (r.t.) for 4 hours. The reaction mixture was added to cold water (10 mL), and extraction was carried out with ethyl acetate (2×20 mL). The organic layer was dried over anhydrous MgSO$_4$ and evaporated to thereby obtain a white solid. The residue was crystallized from a mixed solution (amixture) of AcOEt and n-hexane, to thereby obtain compounds 11a-b as colorless crystalline powder.

a) 3-(4-Benzyloxyphenyl)methylacrylate (11a)

Yield 0.17 g (81%). Melting point (m.p.) 132-133° C. $R_f$=0.18 (AcOEt:n-hexane, 1:19, v/v). IR (KBr) cm$^{-1}$; 1605 (C=C), 1710 (C=O).

$^1$H NMR (CDCl$_3$, 300 MHz) δ 3.79 (s, 3H, O-Me), 5.10 (s, 2H, —CH$_2$—O—), 6.34 (d, J=15.9 Hz, 1H, Ar—CH=CH—), 6.96-6.98 (d, J=8.7 Hz, 2H, Ar—H), 7.33-7.49 (m, 8H, Ar—H), 7.67 (d, J=15.9 Hz, 1H, Ar—CH=C—).

b) 3-(4-Ethoxyphenyl)methylacrylate (11b)

Yield 0.21 g (78%). Melting point (m.p.) 75-76° C. $R_f$=0.15 (AcOEt:n-hexane, 1:14, v/v). IR (KBr) cm$^{-1}$; 1600 (C=C), 1695 (C=O).

$^1$H NMR (CDCl$_3$, 300 MHz) δ 1.43 (t, J=7.2 Hz, 3H, CH$_3$—CH$_2$—), 3.79 (s, 3H, —O—Me), 4.06 (q, J=7.2 Hz, 2H, CH$_3$—CH$_2$—), 6.30 (d, J=16.2 Hz, 1H, Ar—CH=CH—), 6.89 (d, J=9.0 Hz, 2H, Ar—H), 7.46 (d, J=9.0 Hz, 2H, Ar—H), 7.65 (d, J=16.2 Hz, 1H, Ar—CH=CH—).

Example 1-9

Synthesis of Intermediates 12a-b for Glucose Derivative (FIG. 2)

3-(4-Benzyloxy or 4-Ethoxyphenyl)cinnamic acid (12a-b)

A solution obtained by adding any one of the compounds 11a-b (1.0 mmol) to a MeOH-THF (10:1) mixture and 2 N NaOH (10 mL) was heated at 60° C. for 1 hour. Immediately, a colorless powdery crystallized precipitate was obtained, and recovered by filtration. A mixture of AcOEt and n-hexane was recovered, to thereby obtain colorless needles 12a-b.

a) 3-(4-Benzyloxyphenyl)cinnamic acid (12a)

Yield 0.15 g (79%). Melting point (m.p.) 208-209° C. $R_f$=0.14 (AcOEt:n-hexane, 1:5, v/v). IR (KBr) cm$^{-1}$; 1600 (C=C), 1670 (C=O), 2600-3020 (COOH).

$^1$H NMR (DMSO-$d_6$, 300 MHz) δ 5.15 (s, 2H, —CH$_2$—O—), 6.37 (d, J=16.2 Hz, 1H, Ar—CH=CH—), 7.05 (d, J=7.5 Hz, 2H, Ar—H), 7.34-7.56 (m, 6H, Ar—H, Ar—CH=CH—), 7.63 (d, J=7.8 Hz, 2H, Ar—H), 12.20 [br s, 1H, —COOH, (exchangeable with D$_2$O)].

b) 3-(4-Ethoxyphenyl)cinnamic acid (12b)

Yield 0.18 g (72%). Melting point (m.p.) 198-199° C. $R_f$=0.11 (AcOEt:n-hexane, 1:5, v/v). IR (KBr) cm$^{-1}$; 1600 (C=C), 1670 (C=O), 2600-3000 (COOH).

$^1$H NMR (DMSO-$_6$, 300 MHz) δ 1.33 (t, J=7.2 Hz, 3H, CH$_3$—CH$_2$—), 4.07 (q, J=7.2 Hz, 2H, CH$_3$—CH$_2$—), 6.38 (d, J=16.2 Hz, 1H, Ar—CH=CH—), 6.96 (d, J=8.7 Hz, 2H, Ar—H), 7.56 (d, J=16.2 Hz, 1H, Ar—CH=CH—), 7.62 (d, J=9.0 Hz, 2H, Ar—H), 12.19 [br s, 1H, —COOH (exchangeable with D$_2$O)].

Example 1-10

Synthesis of Intermediates 13a-h for Glucose Derivative (FIG. 2)

A mixture of the intermediate 8 in Example 6 (0.85 g, 1 mmol), an unsaturated fatty acid or an aromatic acid (3 mmol), DCC (0.62 g, 3 mmol), and DMAP (0.36 g, 3 mmol) were added to dry dichloromethane (10 mL), and the mixture was stirred under atmosphere of argon at 0° C. for 1 hour and allowed to stand at room temperature (r.t.) for 5 to 7 hours. After completion of the reaction, a white reaction precipitate (1,3-dicyclohexyl urea) was removed using a Buchner funnel (G3), and the filtrate was washed twice with 50 mL of 0.5 N citric acid and washed twice with 50 mL of a solution of 0.5 N sodium bicarbonate. In this step, dicyclohexyl urea was further precipitated and removed by filtration. The filtrate was dried over anhydrous sodium sulfate, and the solvent was evaporated under reduced pressure. The residue was subjected to silica gel flash column chromatography, to thereby obtain a colorless needle-like product from a fraction eluted with AcOEt-n-hexane (1:4, v/v).

a) 5,7-Dibenzyloxy-2-(2,2-diphenylbenzo[d][1,3] dioxol-5-yl)-4,6-O-isopropylidene-2-(3',4'-dihydroxyphenyl)-3-β-D-(2",3"-di-p-benzyloxycoumaroyl) glucosyl-4H-chromen-4-one (13a)

Yield 0.80 g (61%). Melting point (m.p.) 202-204° C. $R_f$=0.38 (AcOEt:n-hexane, 3:8, v/v). IR (KBr) cm$^{-1}$; 1605 and 1635 (C=C), 1720 (C=O).

$^1$H NMR (CDCl$_3$, 500 MHz) δ 1.33 (s, 6H, 2×Me), 3.45-3.48 (ddd, J$_{5'',6''Ha}$=5.4 Hz, J$_{5'',6''Hb}$=4.8 Hz, J$_{4'',5''}$=9.6 Hz, 1H, 5"-H), 3.57 (dd, J$_{5'',6''Hb}$=4.8 Hz, J$_{gem}$=10.8 Hz, 1H, 6"-H$_b$), 3.80 (dd, J$_{5'',6''Ha}$=5.4 Hz, J$_{gem}$=10.8 Hz, 1H, 6"-H$_a$), 3.89 (dd, J$_{4'',5''}$=9.6 Hz, J$_{3'',4''}$=9.0 Hz, 1H, 4"-H), 5.03, 5.04, and 5.08 (each s, each 2H, 6H, 3×CH$_2$—O—), 5.23/5.27 (AB system, dd, J$_{AB}$=15.6 Hz, 2H, —O—CH$_2$—), 5.34-5.41 (m, 2H, 2"-H, 3"-H), 6.01 (d, J$_{1'',2''}$=6.5 Hz, 1H, 1"-H), 6.28 and 6.31 (each d, each 1H, each J$_{trans}$=16.0 Hz, 2H, 2×Ar—CH=CH—), 6.41 (d, $^4$J=1.5 Hz, 1H, 8-H), 6.49 (d, $^4$J=1.5 Hz, 1H, 6-H), 6.87 and 6.94 (each d, each 2H, each J=9.0 Hz, 4H, 2×3''''-H, 2×5''''-H), 6.99 (d, J=8.5 Hz, 1H, 5'-H), 7.28-7.44 (m, 28H, Ar—H), 7.55-7.69 (m, 10H, 6'-H, 2'-H, 2×2''''-H, 2×6''''-H, and 2×Ar—CH=CH—). MS (FAB, 3-nitrobenzyl alcohol was used as matrix): m/z; 1321 ([MH]$^+$). Anal. Calcd for C$_{83}$H$_{68}$O$_{16}$: C, 75.44; H, 5.19. Found: C, 75.32; H, 5.20.

b) 5,7-Dibenzyloxy-2-(2,2-diphenylbenzo[d][1,3] dioxol-5-yl)-4,6-O-isopropylidene-2-(3',4'-dihydroxyphenyl)-3-β-D-(2",3"-di-p-ethoxycoumaroyl)glucosyl-4H-chromen-4-one (13b)

Yield 0.81 g (68%). Melting point (m.p.) 186-187° C. $R_f$=0.30 (AcOEt:n-hexane, 3:8, v/v). IR (KBr) cm$^{-1}$; 1605 and 1625 (C=C), 1720 (C=O).

$^1$H NMR (CDCl$_3$, 600 MHz) δ 1.32 and 1.33 (each s, each 3H, 6H, 2×Me), 1.39 and 1.42 (each t, each 3H, J=7.2 Hz, 2×CH$_2$Me), 3.44-3.49 (ddd, J$_{5'',6''Ha}$=5.4 Hz, J$_{5'',6''Hb}$=4.8 Hz, J$_{4'',5''}$=9.6 Hz, 1H, 5"-H), 3.57 (dd, J$_{5'',6''Hb}$=4.8 Hz, J$_{gem}$=10.8 Hz, 1H, 6"-H$_b$), 3.81 (dd, J$_{5'',6''Ha}$=5.4 Hz, J$_{gem}$=10.8 Hz, 1H, 6"-H$_a$), 3.90 (dd, J$_{4'',5''}$=9.6 Hz, J$_{3'',4''}$=9.0 Hz, 1H, 4"-H), 4.02 and 4.05 (each q, each 2H, J=7.2 Hz, 2×CH$_3$—CH$_2$—), 5.01/5.03 (AB system, dd, J$_{AB}$=12.0 Hz, 2H, —O—CH$_2$—), 5.24/5.28 (AB system, dd, J$_{AB}$=13.2 Hz, 2H, —O—CH$_2$—), 5.34-5.40 (m, 2H, 2"-H and 3"-H), 6.01 (d, J$_{1'',2''}$=7.2 Hz, 1H, 1"-H), 6.27 and 6.30 (each d, each 1H, each J$_{trans}$=16.2 Hz, 2H, 2×Ar—CH=CH—), 6.41 (d, $^4$J=2.4 Hz, 1H, 8-H), 6.49 (d, $^4$J=2.4 Hz, 1H, 6-H), 6.78 and 6.84 (each d, each 2H, each J=9.0 Hz, 4H, 2×3''''-H and 2×5''''-H), 6.99 (d, J=8.4 Hz, 1H, Ar—H, 5'-H), 7.34-7.43 (m, 18H, Ar—H), 7.56-7.69 (m, 10H, Ar—H, 6'-H). MS (FAB, 3-nitrobenzyl alcohol was used as matrix) m/z; 1197 ([MH]$^+$). Anal. Calcd for C$_{73}$H$_{64}$O$_{16}$: C, 73.23; H, 5.39. Found: C, 73.07; H, 5.58.

c) 5,7-Dibenzyloxy-2-(2,2-diphenylbenzo[d][1,3] dioxol-5-yl)-4,6-O-isopropylidene-2-(3',4'-dihydroxyphenyl)-3-β-D-(2",3"-di-p-methylcoumaroyl)glucosyl-4H-chromen-4-one (13c)

Yield 0.79 g (69%). Melting point (m.p.) 208-209° C. $R_f$=0.29 (AcOEt:n-hexane, 3:8, v/v). IR (KBr) cm$^{-1}$; 1610 and 1638 (C=C), 1720 (C=O).

$^1$H NMR (CDCl$_3$, 600 MHz) δ 1.33 and 1.34 (each s, each 3H, 6H, 2×Me), 2.32 and 2.36 (each s, each 3H, 2×Ar—CH$_3$), 3.44-3.49 (ddd, J$_{5'',6''Ha}$=5.4 Hz, J$_{5'',6''Hb}$=4.8 Hz, J$_{4'',5''}$=9.6 Hz, 1H, 5"-H), 3.57 (dd, J$_{5'',6''Hb}$=4.8 Hz, J$_{gem}$=10.8 Hz, 1H, 6"-H$_b$), 3.81 (dd, J$_{5'',6''Ha}$=5.4 Hz, J$_{gem}$=10.8 Hz, 1H, 6"-H$_a$), 3.90 (t, J=9.6 Hz, 1H, 4"-H), 5.03 (s, 2H, CH$_2$—O), 5.25/5.28 (AB system, dd, J$_{AB}$=13.2 Hz, 2H, O—CH$_2$), 5.34-5.41 (m, 2H, 2"-H, 3"-H), 6.02 (d, J$_{1'',2''}$=7.2 Hz, 1H, 1"-H), 6.37 and 6.40 (each d, each 1H, each J$_{trans}$=16.2 Hz, 2H, 2×Ar—CH=CH—), 6.41 (d, $^4$J=2.4 Hz, 1H, 8-H), 6.50 (d, $^4$J=2.4 Hz, 1H, 6-H), 6.99 (d, J=7.8 Hz, 1H, 5'-H), 7.10 and 7.15 (each d, each 2H, each J=7.8 Hz, 4H, 2×2''''-H and 2×6''''-H), 7.35-7.43 (m, 18H, Ar—H), 7.55-7.69 (m, 10H, Ar—H, 6'-H, 2'-H, 2×3''''-H, 2×5''''-H, and 2×Ar—CH=CH—). MS (FAB, 3-nitrobenzyl alcohol was used as matrix) m/z; 1137 ([MH]$^+$). Anal. Calcd for C$_{71}$H$_{60}$O$_{14}$: C, 74.99; H, 5.32. Found: C, 74.77; H, 5.38.

d) 5,7-Dibenzyloxy-2-(2,2-diphenylbenzo[d][1,3] dioxol-5-yl)-4,6-O-isopropylidene-2-(3',4'-dihydroxyphenyl)-3-β-D-(2",3"-di-p-flurocoumaroyl)glucosyl-4H-chromen-4-one (13d)

Yield 0.81 g (73%). Melting point (m.p.) 192-193° C. $R_f$=0.33 (AcOE:n-hexane, 3:8, v/v). IR (KBr) cm$^{-1}$; 1605 and 1640 (C=C), 1720 (C=O).

¹H NMR (CDCl₃, 600 MHz) δ 1.33 and 1.34 (each s, each 3H, 6H, 2×Me), 3.43-3.49 (ddd, $J_{5'',6''Ha}$=5.4 Hz, $J_{5'',6''Hb}$=4.8 Hz, $J_{4'',5''}$=9.6 Hz, 1H, 5''-H), 3.58 (dd, $J_{5'',6''Hb}$=4.8 Hz, $J_{gem}$=10.8 Hz, 1H, 6''-H$_b$), 3.81 (dd, $J_{5'',6''Ha}$=5.4 Hz, $J_{gem}$=10.8 Hz, 1H, 6''-H$_a$), 3.89 (dd, $J_{4'',5''}$=9.6 Hz, $J_{3'',4''}$=9.0 Hz, 1H, 4''-H), 5.23 (s, 2H, CH₂—O), 5.24/5.28 (AB system, dd, $J_{AB}$=13.2 Hz, 2H, O—CH₂), 5.35-5.42 (m, 2H, 2''-H and 3''-H), 5.99 (d, $J_{1'',2''}$=7.2 Hz, 1H, 1''-H), 6.34 and 6.37 (each d, each 1H, each $J_{trans}$=16.2 Hz, 2H, 2×Ar—CH=CH—), 6.42 (d, ⁴J=2.4 Hz, 1H, 8-H), 6.51 (d, ⁴J=2.4 Hz, 1H, 6-H), 6.96 (d, J=8.4 Hz, 1H, 5'-H), 6.98 and 7.04 (each t, each 2H, J=8.4 Hz, 4H, 2×3''''-H and 2×5''''-H), 7.34-7.49 (m, 20H, Ar—H), 7.60-7.63 (m, 4H, Ar—H, 2×2''''-H and 2×6''''-H), 7.65-7.70 (m, 4H, 6'-H, 2'-H, and 2×Ar—CH=CH—). MS (FAB, 3-nitrobenzyl alcohol was used as matrix) m/z; 1145 ([MH]⁺). Anal. Calcd for C₆₉H₅₄F₂O₁₄: C, 72.37; H, 4.75. Found: C, 72.65; H, 4.98.

e) 5,7-Dibenzyloxy-2-(2,2-diphenylbenzo[d][1,3]
dioxol-5-yl)-4,6-O-isopropylidene-2-(3',4'-dihydroxyphenyl)-3-β-D-(2'',3''-di-p-ethoxybenzoyloxy)glucosyl-4H-chromen-4-one (13e)

Yield 0.76 g (67%). Melting point (m.p.) 134-136° C. $R_f$=0.30 (AcOEt:n-hexane, 3:8, v/v). IR (KBr) cm⁻¹; 1605 and 1615 (C=C), 1725 (C=O).
¹H NMR (CDCl₃, 600 MHz) δ 1.32 and 1.35 (each s, each 3H, 6H, 2×Me), 1.37 and 1.42 (each t, each 3H, J=7.2 Hz, 6H, 2×CH₂Me), 3.46-3.53 (ddd, $J_{5'',6''Ha}$=5.4 Hz, $J_{5'',6''Hb}$=4.8 Hz, $J_{4'',5''}$=9.6 Hz, 1H, 5''-H), 3.61 (dd, $J_{5'',6''Hb}$=4.8 Hz, $J_{gem}$=10.8 Hz, 1H, 6''-H$_b$), 3.84 (dd, $J_{5'',6''Ha}$=5.4 Hz, $J_{gem}$=10.8 Hz, 1H, 6''-H$_a$), 3.95-3.99 (m, 3H, 4''-H and CH₃—CH₂—O), 4.05 (q, J=7.2 Hz, 2H, CH₃—CH₂—O—), 5.03 (s, 2H, CH₂—O), 5.24/5.27 (AB system, dd, $J_{AB}$=12.6 Hz, 2H, O—CH₂), 5.50-5.55 (m, 2H, 2''-H and 3''-H), 6.05 (d, $J_{1'',2''}$=7.2 Hz, 1H, 1''-H), 6.43 (d, ⁴J=1.8 Hz, 1H, 8-H), 6.50 (d, ⁴J=1.8 Hz, 1H, 6-H), 6.75 and 6.85 (each d, each 2H, each J=9.0 Hz, 4H, 2×3'''-H and 2×5'''-H), 6.96 (d, J=8.4 Hz, 1H, 5'-H), 7.30-7.43 (m, 14H, Ar—H), 7.58-7.69 (m, 8H, Ar—H), 7.94 and 7.96 (each d, each 2H, each J=9.0 Hz, 4H, 2×2'''-H and 2×6'''-H). MS (FAB, 3-nitrobenzyl alcohol was used as matrix) m/z; 1145 ([MH]⁺). Anal. Calcd for C₆₉H₆₀O₁₆: C, 72.37; H, 5.28. Found: C, 71.93; H, 5.13.

f) 5,7-Dibenzyloxy-2-(2,2-diphenylbenzo[d][1,3]
dioxol-5-yl)-4,6-O-isopropylidene-2-(3',4'-dihydroxyphenyl)-3-β-D-(2'',3''-di-p-propylbenzoyloxy)glucosyl-4H-chromen-4-one (13f)

Yield 0.80 g (70%). Melting point (m.p.) 130-131° C. $R_f$=0.33 (AcOEt:n-hexane, 3:8, v/v). IR (KBr) cm⁻¹; 1610 and 1640 (C=C), 1738 (C=O).
¹H NMR (CDCl₃, 600 MHz) δ 0.89-0.93 (each t, each 3H, J=7.2 Hz, 2×CH₂Me), 1.32 and 1.35 (each s, each 3H, 2×Me), 1.58-1.65 (m, 4H, 2×CH₂Me), 2.60-2.54 (each t, each 2H, J=7.2 Hz, 2×CH₂CH₂Me), 3.49-3.52 (ddd, $J_{5'',6''Ha}$=5.4 Hz, $J_{5'',6''Hb}$=4.8 Hz, $J_{4'',5''}$=9.6 Hz, 1H, 5''-H), 3.61 (dd, $J_{5'',6''Hb}$=4.8 Hz, $J_{gem}$=10.8 Hz, 1H, 6''-H$_b$), 3.83 (dd, $J_{5'',6''Ha}$=5.4 Hz, $J_{gem}$=10.8 Hz, 1H, 6''-H$_a$), 3.99 (dd, $J_{4'',5''}$=9.6 Hz, $J_{3'',4''}$=9.0 Hz, 1H, 4''-H), 5.06 (s, 2H, CH₂—O), 5.24/5.26 (AB system, dd, $J_{AB}$=12.6 Hz, 2H, O—CH₂), 5.53-5.58 (m, 2H, 2''-H and 3''-H), 6.10 (d, $J_{1'',2''}$=7.2 Hz, 1H, 1''-H), 6.44 (d, ⁴J=2.4 Hz, 1H, 8-H), 6.51 (d, ⁴J=2.4 Hz, 1H, 6-H), 6.97 (d, J=8.4 Hz, 1H, 5'-H), 7.10 and 7.20 (each d, each 2H, each J=8.4 Hz, 4H, 2×3''''-H and 2×5''''-H), 7.36-7.42 (m, 14H, Ar—H), 7.60-7.67 (m, 8H, Ar—H), 7.91 and 7.94 (each d, each 2H, each J=8.4 Hz, 4H, 2×2'''-H and 2×6'''-H). MS (FAB, 3-nitrobenzyl alcohol was used as matrix) m/z; 1141 ([MH]⁺). Anal. Calcd for C₇₁H₆₄O₁₄: C, 74.72; H, 5.65. Found: C, 74.72; H, 5.35.

g) 5,7-Dibenzyloxy-2-(2,2-diphenylbenzo[d][1,3]
dioxol-5-yl)-4,6-O-isopropylidene-2-(3',4'-dihydroxyphenyl)-3-β-D-(2'',3''-di-p-flurobenzoyloxy)glucosyl-4H-chromen-4-one (13g)

Yield 0.78 g (72%). Melting point (m.p.) 243-244° C. $R_f$=0.29 (AcOEt:n-hexane, 3:8, v/v). IR (KBr) cm⁻¹; 1605 and 1645 (C=C), 1725 (C=O).
¹H NMR (CDCl₃, 600 MHz) δ 1.33 and 1.38 (each s, each 3H, 2×Me), 3.46-3.51 (ddd, $J_{5'',6''Ha}$=5.4 Hz, $J_{5'',6''Hb}$=4.8 Hz, $J_{4'',5''}$=9.6 Hz, 1H, 5''-H), 3.61 ((dd, $J_{5'',6''Hb}$=4.8 Hz, $J_{gem}$=10.8 Hz, 1H, 6'-H$_b$), 3.84 (dd, $J_{5'',6''Ha}$=5.4 Hz, $J_{gem}$=10.8 Hz, 1H, 6''-H$_a$), 3.97 (dd, $J_{4'',5''}$=9.6 Hz, $J_{3'',4''}$=9.0 Hz, 1H, 4''-H), 5.07 (s, 2H, CH₂—O), 5.23/5.27 (AB system, dd, $J_{AB}$=13.2 Hz, 2H, O—CH₂), 5.50-5.56 (m, 2H, 2''-H and 3''-H), 6.01 (d, $J_{1'',2''}$=7.2 Hz, 1H, 1''-H), 6.45 (d, ⁴J=2.4 Hz, 1H, 8-H), 6.51 (d, ⁴J=2.4 Hz, 1H, A6-H), 6.94 and 7.06 (each t, each 2H, J=9.0 Hz, 4H, 2×3'''-H and 2×5'''-H), 6.96 (d, J=8.4 Hz, 1H, 5'-H), 7.34-7.43 (m, 14H, Ar—H), 7.58-7.66 (m, 8H, Ar—H), 8.00 and 8.05 (each dd, each 2H, J=8.4 Hz, J=9.0 Hz, 4H, 2×2'''-H and 2×6'''-H). MS (FAB, 3-nitrobenzyl alcohol was used as matrix) m/z; 1093 ([MH]⁺).

h) 5,7-Dibenzyloxy-2-(2,2-diphenylbenzo[d][1,3]
dioxol-5-yl)-4,6-O-isopropylidene-2-(3',4'-dihydroxyphenyl)-3-β-D-(2'',3''-di-p-flurobenzyloxy)glucosyl-4H-chromen-4-one (13h)

Yield 0.79 g (70%). Melting point (m.p.) 218-219° C. $R_f$=0.31 (AcOEt:n-hexane, 3:8, v/v). IR (KBr) cm⁻¹; 1610 and 1638 (C=C), 1750 (C=O).
¹H NMR (CDCl₃, 600 MHz) δ 1.24 and 1.26 (each s, each 3H, 2×Me), 3.21-3.25 (ddd, $J_{5'',6''Ha}$=5.4 Hz, $J_{5'',6''Hb}$=4.8 Hz, $J_{4'',5''}$=9.6 Hz, 1H, 5''-H), 3.61 (dd, $J_{5'',6''Hb}$=4.8 Hz, $J_{gem}$=10.8 Hz, 1H, 6''-H$_b$), 3.43 (s, 2H, Ar—CH₂—CO), 3.59/3.70 (AB system, dd, $J_{AB}$=15.6 Hz, 2H, Ar—CH₂—CO), 3.60 (t, J=9.6 Hz, 1H, 4''-H), 3.66 (dd, $J_{5'',6''Ha}$=5.4 Hz, $J_{gem}$=10.8 Hz, 1H, 6''-H$_a$), 5.08 (s, 2H, —CH₂—O—), 5.13-5.21 (m, 2H, 2''-H, 3''-H), 5.26 (s, 2H, —CH₂—O—), 5.66 (d, $J_{1'',2''}$=7.2 Hz, 1H, 1''-H), 6.46 (d, ⁴J=2.4 Hz, 1H, 8-H), 6.55 (d, ⁴J=2.4 Hz, 1H, 6-H), 6.91 and 6.96 (each t, each 2H, J=9.0 Hz, 4H, 2×3''''-H and 2×5''''-H), 6.94 (d, J=8.4 Hz, 1H, 5'-H), 7.15 and 7.20 (each dd, each 2H, each J=8.4 Hz, each J=9.0 Hz, 4H, 2×2''''-H and 2×6''''-H), 7.33-7.41 (m, 14H, Ar—H), 7.55-7.62 (m, 8H, Ar—H). MS (FAB, 3-nitrobenzyl alcohol was used as matrix) m/z; 1121 ([MH]⁺).

Example 1-11

Synthesis of Intermediates 14a-h for Glucose Derivative (FIG. 2)

Each of the compounds 13a-h (1.0 mmol) obtained in Example 10 was added to a mixture of MeOH (25 mL) and 0.5 N HCl (10 mL), and the mixture was heated at 50° C. for 2 to 3 hours. Then, the mixture was cooled to room temperature (r.t.), and the solution was concentrated under reduced pressure. Then, the residue was neutralized with triethylamine, and the solution was further evaporated, and the residue was dried completely. The dried residue was treated with dry ethanol, and insoluble matter was removed by filtration. The filtrate was evaporated under reduced pressure, and the residue was subjected to silica gel column chromatography, to thereby obtain compounds 14a-h as colorless powdery products from fractions eluted with AcOEt-n-hexane (1:1, v/v).

a) 5,7-Dibenzyloxy-2-(2,2-diphenylbenzo[d][1,3] dioxol-5-yl)-2-(3',4'-dihydroxyphenyl)-3-β-D-(2",3"-di-p-benzyloxycoumaroyl)glucosyl-4H-chromen-4-one (14a)

Yield 0.90 g (70%). Melting point (m.p.) 122-123° C. $R_f$=0.28 (AcOEt:n-hexane, 1:1, v/v). IR (KBr) cm$^{-1}$; 1605 and 1640 (C=C), 1720 (C=O), 3420 (OH).

$^1$H NMR (CDCl$_3$, 600 MHz) δ 3.47-3.50 (m, 1H, 5"-H), 3.58 (dd, $J_{5'',6''Hb}$=3.0 Hz, $J_{gem}$=12.0 Hz, 1H, 6"-H$_b$), 3.73 (dd, $J_{5'',6''Ha}$=3.0 Hz, $J_{gem}$=12.0 Hz, 1H, 6"-H$_a$), 3.82 (t, J=9.6 Hz, 1H, 4"-H), 5.02, 5.03, 5.08 (each s, each 2H, 6H, 3×CH$_2$—O), 5.18 (t, J=9.6 Hz, 1H, 3"-H), 5.22/5.26 (AB system, dd, $J_{AB}$=13.2 Hz, 2H, CH$_2$—O), 5.38 (dd, $J_{2'',3''}$=9.6 Hz, $J_{1'',2''}$=7.5 Hz, 1H, 2"-H), 5.73 (d, $J_{1'',2''}$=7.5 Hz, 1H, 1"-H), 6.27 and 6.29 (each d, each 1H, each $J_{trans}$=16.2 Hz, 2H, 2×Ar—CH=CH—), 6.41 (d, $^4J$=2.4 Hz, 1H, 8-H), 6.50 (d, $^4J$=2.4 Hz, 1H, 6-H), 6.87 and 6.93 (each d, each 2H, each J=9.0 Hz, 4H, 2×3""-H and 2×5""-H), 6.97 (d, J=8.0 Hz, 1H, 5'-H), 7.29-7.43 (m, 28H, Ar—H), 7.53-7.69 (m, 10H, 6'-H, 2'-H, 2×2""-H, 2×6""-H, and 2×Ar—CH=CH—). MS (FAB, 3-nitrobenzyl alcohol was used as matrix) m/z; 1281 ([MH]$^+$). Anal. Calcd for C$_{80}$H$_{64}$O$_{16}$: C, 74.99; H, 5.03. Found: C, 75.10; H, 5.10.

b) 5,7-Dibenzyloxy-2-(2,2-diphenylbenzo[d][1,3] dioxol-5-yl)-2-(3',4'-dihydroxyphenyl)-3-β-D-(2",3"-di-p-ethoxycoumaroyl)glucosyl-4H-chromen-4-one (14b)

Yield 0.88 g (76%). Melting point (m.p.) 128-129° C. $R_f$=0.23 (AcOEt:n-hexane, 1:1, v/v). IR (KBr) cm$^{-1}$; 1610 and 1640 (C=C), 1720 (C=O), 3420 (OH).

$^1$H NMR (CDCl$_3$, 600 MHz) δ 1.42 and 1.39 (each t, each 3H, J=7.2 Hz, 6H, 2×CH$_2$Me), 3.37 [br s, 1H, 6"-OH (exchangeable with D$_2$O)], 3.47-3.50 (m, 1H, 5"-H), 3.57 (dd, $J_{5'',6''Hb}$=4.8 Hz, $J_{gem}$=12.0 Hz, 1H, 6"-H$_b$), 3.72 (dd, $J_{5'',6''Ha}$=3.0 Hz, $J_{gem}$=12.0 Hz, 1H, 6"-H$_a$), 3.83 (dd, $J_{4'',5''}$=9.6 Hz, $J_{3'',4''}$=9.0 Hz, 1H, 4"-H), 5.04 (s, 2H, OCH$_2$), 5.17 (t, J=9.0 Hz, 1H, 3"-H), 5.21/5.27 (AB system, dd, $J_{AB}$=13.2 Hz, 2H, OCH$_2$), 5.38 (dd, $J_{2'',3''}$=9.0 Hz, $J_{1'',2''}$=7.8 Hz, 1H, 2"-H), 5.75 (d, $J_{1'',2''}$=7.8 Hz, 1H, 1"-H), 6.27 and 6.28 (each d, each 1H, each $J_{trans}$=16.2 Hz, 2H, 2×Ar—CH=CH), 6.41 (d, $^4J$=2.4 Hz, 1H, 8-H), 6.50 (d, $^4J$=2.4 Hz, 1H, 6-H), 6.77 and 6.85 (each d, each 2H, each J=8.4 Hz, 4H, 2×3""-H and 2×5""-H), 6.97 (d, J=8.4 Hz, 1H, 5'-H), 7.34-7.43 (m, 18H, Ar—H), 7.54-7.62 (m, 4H, 2×2""-H and 2×6""-H), 7.66 and 7.68 (each d, each 1H, each $J_{trans}$=16.2 Hz, 2H, 2×Ar—CH=CH), 7.67 (dd, J=8.4 Hz, J=1.8 Hz, 1H, 6'-H), 7.69 (d, $^4J$=1.8 Hz, 1H, 2'-H). MS (FAB, 3-nitrobenzyl alcohol was used as matrix) m/z; 1157 ([MH]$^+$). Anal. Calcd for C$_{70}$H$_{60}$O$_{16}$: C, 72.65; H, 5.23. Found: C, 72.48; H, 5.57.

c) 5,7-Dibenzyloxy-2-(2,2-diphenylbenzo[d][1,3] dioxol-5-yl)-2-(3',4'-dihydroxyphenyl)-3-β-D-(2",3"-di-p-methylcoumaroyl)glucosyl-4H-chromen-4-one (14c)

Yield 0.85 g (77%). Melting point (m.p.) 132-133° C. $R_f$=0.25 (AcOEt:n-hexane, 1:1, v/v). IR (KBr) cm$^{-1}$; 1605 and 1635 (C=C), 1720 (C=O), 3420 (OH).

$^1$H NMR (CDCl$_3$, 500 MHz) δ 1.64 [br s, 1H, 6"-OH (exchangeable with D$_2$O)], 2.32 and 2.36 (each s, each 3H, 2×Ar-Me), 3.47-3.50 (m, 1H, 5"-H), 3.57 (dd, $J_{5'',6''Hb}$=4.8 Hz, $J_{gem}$=12.0 Hz, 1H, 6"-H$_b$), 3.72 (dd, $J_{5'',6''Ha}$=3.6 Hz, $J_{gem}$=12.0 Hz, 1H, 6"-H$_a$), 3.82 (dd, $J_{4'',5''}$=9.6 Hz, $J_{3'',4''}$=9.0 Hz, 1H, 4"-H), 5.04 (s, 2H, OCH$_2$), 5.18 (dd, $J_{3'',2''}$=9.0 Hz, $J_{2'',3''}$=9.6 Hz, 1H, 3"-H), 5.24/5.27 (AB system, dd, $J_{AB}$=13.2 Hz, 2H, OCH$_2$), 5.39 (dd, $J_{2'',3''}$=9.6 Hz, $J_{1'',2''}$=7.2 Hz, 1H, 2"-H), 5.74 (d, $J_{1'',2''}$=7.2 Hz, 1H, 1"-H), 6.37 and 6.38 (each d, each 1H, each $J_{trans}$=16.2 Hz, 2H, 2×Ar—CH=CH), 6.42 (d, $^4J$=2.4 Hz, 1H, 8-H), 6.52 (d, $^4J$=2.4 Hz, 1H, 6-H), 6.97 (d, J=8.4 Hz, 1H, 5'-H), 7.09 and 7.16 (each d, each 2H, each J=8.4 Hz, 4H, 2×3""-H and 2×6""-H), 7.32-7.42 (m, 18H, Ar—H), 7.60-7.62 (m, 4H, 2×3""-H and 2×5""-H), 7.66 (dd, J=8.4 Hz, $^4J$=2.4 Hz, 1H, 6'-H), 7.67 (d, $^2J$=2.4 Hz, 1H, 2'-H), 7.69 and 7.70 (each d, each 1H, each $J_{trans}$=16.2 Hz, 2H, 2×Ar—CH=CH). MS (FAB, 3-nitrobenzyl alcohol was used as matrix) m/z; 1097 ([MH]$^+$). Anal. Calcd for C$_{68}$H$_{56}$O$_{14}$: C, 74.44; H, 5.14. Found: C, 74.30; H, 5.27.

d) 5,7-Dibenzyloxy-2-(2,2-diphenylbenzo[d][1,3] dioxol-5-yl)-2-(3',4'-dihydroxyphenyl)-3-β-D-(2",3"-di-p-flurocoumaroyl)glucosyl-4H-chromen-4-one (14d)

Yield 0.87 g (0.79%). Melting point (m.p.) 122-123° C. $R_f$=0.26 (AcOEt:n-hexane, 1:1, v/v). IR (KBr) cm$^{-1}$; 1610 and 1638 (C=C), 1720 (C=O), 3420 (OH).

$^1$H NMR (CDCl$_3$, 600 MHz) δ 3.25 [br s, 1H, 6"-OH (exchangeable with D$_2$O)], 3.47-3.50 (m, 1H, "-H), 3.58 (dd, $J_{5'',6''Hb}$=4.8 Hz, $J_{gem}$=12.0 Hz, 1H, 6"-H$_b$), 3.72 (dd, $J_{5'',6''Ha}$=3.6 Hz, $J_{gem}$=12.0 Hz, 1H, 6"-H$_a$), 3.85 (t, J=9.6 Hz, 1H, 4"-H), 5.04 (s, 2H, OCH$_2$), 5.22-5.29 (m, 3H, OCH$_2$ and 3"-H), 5.38 (dd, $J_{2'',3''}$=9.0 Hz, $J_{1'',2''}$=7.8 Hz, 1H, 2"-H), 5.74 (d, $J_{1'',2''}$=7.2 Hz, 1H, 1"-H), 6.33 and 6.35 (each d, each 1H, each $J_{AB}$=16.2 Hz, 2H, 2×Ar—CH=CH), 6.50 (d, $^4J$=2.4 Hz, 1H, 8-H), 6.50 (d, $^4J$=2.4 Hz, 1H, 6-H), 6.95 and 7.05 (each t, each 2H, J=9.0 Hz, 4H, 2×3""-H and 2×5""-H), 6.97 (d, J=8.4 Hz, 1H, 5'-H), 7.34-7.47 (m, 20H, Ar—H), 7.60-7.62 (m, 4H, 2×2""-H and 2×6""-H), 7.66 (d, J=8.4 Hz, 1H, 6'-H), 7.67 (d, $^4J$=2.4 Hz, 1H, 2'-H), 7.65 and 7.71 (each d, each 1H, each $J_{trans}$=16.2 Hz, 2H, 2×Ar—CH=CH). MS (FAB, 3-nitrobenzyl alcohol was used as matrix) m/z; 1105 ([MH]$^+$). Anal. Calcd for C$_{66}$H$_{50}$F$_2$O$_{14}$: C, 71.73; H, 4.56. Found: C, 71.91; H, 4.59.

e) 5,7-Dibenzyloxy-2-(2,2-diphenylbenzo[d][1,3] dioxol-5-yl)-2-(3',4'-dihydroxyphenyl)-3-β-D-(2",3"-di-p-ethoxybenzoyloxy)glucosyl-4H-chromen-4-one (14e)

Yield 0.82 g (75%). Melting point (m.p.) 128-129° C. $R_f$=0.20 (AcOEt:n-hexane, 1:1, v/v). IR (KBr) cm$^{-1}$; 1605 and 1630 (C=C), 1720 (C=O), 3420 (OH).

$^1$H NMR (CDCl$_3$, 600 MHz): δ1.37 and 1.42 (each t, each 3H, each J=7.2 Hz, 2×CH$_2$Me), 3.51-3.54 (m, 1H, 5"-H), 3.57 (dd, $J_{5'',6''Hb}$=4.8 Hz, $J_{gem}$=12.0 Hz, 1H, 6"-H$_b$), 3.74 (dd, $J_{5'',6''Ha}$=3.6 Hz, $J_{gem}$=12.0 Hz, 1H, 6"-H$_a$), 3.85 (dd, $J_{4'',5''}$=9.6 Hz, $J_{3'',4''}$=9.0 Hz, 1H, 4"-H), 3.97 and 4.06 (each q, each 2H, each J=7.2 Hz, 4H, 2×OCH$_2$Me), 5.07 (s, 2H, OCH$_2$), 5.22-5.27 (m, 3H, OCH$_2$ and 3"-H), 5.56 (dd, $J_{2'',3''}$=9.6 Hz, $J_{1'',2''}$=7.8 Hz, 1H, 2"-H), 5.83 (d, $J_{1'',2''}$=7.8 Hz, 1H, 1"-H), 6.45 (d, $^4J$=2.4 Hz, Ar—H, 8-H), 6.53 (d, $^4J$=2.4 Hz, 1H, 6-H), 6.75 and 6.84 (each d, each 2H, each J=9.0 Hz, 4H, 2×3'''-H and 2×5'''-H), 6.94 (d, J=8.4 Hz, 1H, 5'-H), 7.35-7.43 (m, 14H, Ar—H), 7.59-7.65 (m, 8H, Ar—H), 7.94 and 8.01 (each d, each 2H, each J=9.0 Hz, 4H, 2×2'''-H and 2×6"'-H). MS (FAB, 3-nitrobenzyl alcohol was used as matrix): m/z; 1105 ([MH]$^+$). Anal. Calcd for $C_{66}H_{56}O_{16}$: C, 71.73; H, 5.11. Found: C, 71.76; H, 4.97.

f) 5,7-Dibenzyloxy-2-(2,2-diphenylbenzo[d][1,3]dioxol-5-yl)-2-(3',4'-dihydroxyphenyl)-3-β-D-(2'',3''-di-p-propylbenzoyloxy)glucosyl-4H-chromen-4-one (14f)

Yield 0.86 g (78%). Melting point (m.p.) 118-119° C. $R_f$=0.24 (AcOEt:n-hexane, 1:1, v/v). IR (KBr) cm$^{-1}$; 1610 and 1630 (C=C) 1730 (C=O), 3420 (OH).

$^1$H NMR (CDCl$_3$, 600 MHz) δ 0.89 and 0.92 (each t, each 3H, J=7.2 Hz, 6H, 2×Me), 1.55-1.66 (m, 4H, 2×CH$_2$Me), 2.54-2.60 (each t, each 2H, J=7.2 Hz, 4H, 2×Ar—CH$_2$—CH$_2$Me), 3.36 [brs, 1H, 6''-OH (exchangeable with D$_2$O)], 3.51-3.54 (m, 1H, 5''-H), 3.58 (dd, $J_{5'',6''Hb}$=4.8 Hz, $J_{gem}$=12.0 Hz, 1H, 6''-H$_b$), 3.74 (dd, $J_{5'',6''Ha}$=3.6 Hz, $J_{gem}$=12.0 Hz, 1H, 6'-H$_a$), 3.87 (dd, $J_{4'',5''}$=9.6 Hz, $J_{3'',4''}$=9.0 Hz, 1H, 4''-H), 5.07 (s, 2H, OCH$_2$), 5.25 (AB system, dd, $J_{AB}$=13.2 Hz, 2H, OCH$_2$), 5.30 (dd, $J_{3'',4''}$=9.0 Hz, $J_{2'',3''}$=9.6 Hz, 1H, 3''-H), 5.58 (dd, $J_{2'',3''}$=9.6 Hz, $J_{1'',2''}$=7.8 Hz, 1H, 2''-H), 5.85 (d, $J_{1'',2''}$=7.8 Hz, 1H, 1''-H), 6.45 (d, $^4$J=2.4 Hz, 1H, 8-H), 6.53 (d, $^4$J=2.4 Hz, 1H, 6-H), 6.93 (d, J=8.9 Hz, 1H, 5'-H), 7.10 and 7.20 (each d, each 2H, each J=9.0 Hz, 4H, 2×3'''-H and 2×5'''-H), 7.35-7.93 (m, 14H, Ar—H), 7.59-7.64 (m, 8H, Ar—H), 7.91 and 7.99 (each d, each 2H, each J=9.0 Hz, 4H, 2×2'''-H and 2×6'''-H). MS (FAB, 3-nitrobenzyl alcohol was used as matrix) m/z; 1101 ([MH]$^+$). Anal. Calcd for $C_{68}H_{60}O_{14}$: C, 74.17; H, 5.49. Found: C, 74.57; H, 5.44.

g) 5,7-Dibenzyloxy-2-(2,2-diphenylbenzo[d][1,3]dioxol-5-yl)-2-(3',4'-dihydroxyphenyl)-3-β-D-(2'',3''-di-p-flurobenzoyloxy)glucosyl-4H-chromen-4-one (14g)

Yield 0.83 g (79%). Melting point (m.p.) 134-135° C. $R_f$=0.18 (AcOEt:n-hexane, 1:1, v/v). IR (KBr) cm$^{-1}$; 1600 and 1630 (C=C), 1738 (C=O), 3415 (OH).

$^1$HNMR (CDCl$_3$, 600 MHz) δ 3.45 [br s, 1H, 4''-OH (exchangeable with D$_2$O)], 3.49-3.52 (m, 1H, 5''-H), 3.58 (dd, $J_{5'',6''Hb}$=4.8 Hz, $J_{gem}$=12.0 Hz, 1H, 6''-H$_b$), 3.73 (dd, $J_{5'',6''Ha}$=3.0 Hz $J_{gem}$=12.0 Hz, 1H, 6''-H$_a$), 3.90 (dd, $J_{4'',5''}$=9.6 Hz, $J_{3'',4''}$=9.0 Hz, 1H, 4''-H), 5.08 (s, 2H, OCH$_2$), 5.24/5.27 (AB system, dd, $J_{AB}$=12.6 Hz, 2H, OCH$_2$), 5.32 (dd, $J_{3'',4''}$=9.0 Hz, $J_{2'',3''}$=9.6 Hz, 1H, 3''-H), 5.54 (dd, $J_{2'',3''}$=9.6 Hz, $J_{1'',2''}$=7.8 Hz, 1H, 2''-H), 5.77 (d, $J_{1'',2''}$=7.8 Hz, 1H, 1''-H), 6.47 (d, $^4$J=2.4 Hz, 1H, 8-H), 6.54 (d, $^4$J=2.4 Hz, 1H, 6-H), 6.93 and 7.07 (each t, each 2H, J=9.0 Hz, 4H, 2×3'''-H and 2×5'''-H), 6.94 (d, J=8.4 Hz, 1H, 5'-H), 7.33-7.43 (m, 14H, Ar—H), 7.58-7.63 (m, 8H, Ar—H), 8.02 and 8.08 (each dd, each 2H, J=9.0 Hz, J=5.4 Hz, 4H, 2×2'''-H and 2×6'''-H), 8.08 (dd, J=9.0 Hz, J=5.4 Hz, 2H, Ar—H). MS (FAB, 3-nitrobenzyl alcohol was used as matrix) m/z; 1053 ([MH]$^+$).

h) 5,7-Dibenzyloxy-2-(2,2-diphenylbenzo[d][1,3]dioxol-5-yl)-2-(3',4'-dihydroxyphenyl)-3-β-D-(2'',3''-di-p-flurobenzyloxy)glucosyl-4H-chromen-4-one (14h)

Yield 0.82 g (76%). Melting point (m.p.) 162-163° C. $R_f$=0.26 (AcOEt:n-hexane, 1:1, v/v). IR (KBr) cm$^{-1}$; 1600 and 1630 (C=C), 1730 (C=O), 3410 (OH).

$^1$H NMR (CDCl$_3$, 600 MHz) δ 3.24-3.27 (m, 1H, 5''-H), 3.37 (dd, $J_{5'',6''Hb}$=4.8 Hz, $J_{gem}$=12.0 Hz, 1H, 6''-H$_b$), 3.43/3.45 (AB system, dd, $J_{AB}$=15.6 Hz, 2H, Ar—CH$_2$—CO), 3.52 (dd, $J_{5'',6''Ha}$=3.6 Hz, $J_{gem}$=12.0 Hz, 1H, 6''-H$_a$), 3.58/3.72 (AB system, dd, $J_{AB}$=15.6 Hz, 2H, Ar—CH$_2$—CO) 3.59 (dd, $J_{4'',5''}$=9.6 Hz, $J_{3'',4''}$=9.0 Hz, 1H, 4''-H), 5.06 (dd, $J_{3'',4''}$=9.0 Hz, $J_{2'',3''}$=9.6 Hz, 1H, 3''-H), 5.09 (s, 2H, OCH$_2$), 5.15 (dd, $J_{2'',3''}$=9.6 Hz, $J_{1'',2''}$=7.8 Hz, 1H, 2''-H), 5.23 (s, 2H, OCH$_2$), 5.37 (d, $J_{1'',2''}$=7.8 Hz, 1H, 1''-H), 6.48 (d, $^4$J=2.4 Hz, 1H, 8-H), 6.56 (d, $^4$J=2.4 Hz, 1H, 6-H), 6.92 and 6.98 (each t, each 2H, J=9.0 Hz, 4H, 2×3''''-H and 2×5''''-H), 6.96 (d, J=8.4 Hz, 1H, 5'-H), 7.13 and 7.22 (each dd, each 2H, each J=8.4 Hz, each J=9.0 Hz, 4H, 2×2''''-H and 2×6''''-H), 7.36-7.42 (m, 14H, Ar—H), 7.56-7.61 (m, 8H, Ar—H). MS (FAB, 3-nitrobenzyl alcohol was used as matrix) m/z; 1081 ([MH]$^+$).

Example 1-12

Synthesis of Final Compounds 15a-h, 16, and 17 for Glucose Derivative (FIG. 2)

Any one of the intermediates 14a-h, 5, and 7 (1.00 mmol) was added to a mixture of EtOAc-EtOH (1:1, 30 mL) and 10% Pd—C (1 equiv.), and the mixture was stirred well and allowed to stand under a hydrogen atmosphere at room temperature for 8 to 10 hours. Pd—C was removed by filtration, and the filtrate was evaporated under reduced pressure at 30° C. The residue was subjected to silica gel flash column chromatography, to thereby obtain compounds 15a-h, 16, and 17 as pale-yellow powdery products from fractions eluted with AcOEt-n-hexane (2:1 to 4:1, v/v).

a) 2-(3',4'-Dihydroxy)-5,7-dihydroxy-3-β-D-(2'',3''-di-p-hydroxyphenylethylcarboxy)glucosyl-4H-chromen-4-one (15a)

Yield 0.60 g (79%). Melting point (m.p.) 173-174° C. $R_f$=0.09 (AcOEt). IR (KBr) cm$^{-1}$; 1610 and 1638 (C=C), 1738 (C=O), 3405 (OH).

$^1$H NMR (DMSO-d$_6$, 600 MHz) δ 2.33 and 2.44 (each t, each 2H, J=7.8 Hz, 4H, 2×ArCH$_2$CH$_2$CO), 2.64 and 2.69 (each t, each 2H, J=7.8 Hz, 4H, 2×ArCH$_2$CH$_2$CO), 3.29-3.37 (m, 2H, 5''-H and 6''-H$_b$), 3.49 [ddd (triplet after addition of D$_2$O, J=9.6 Hz). $J_{3'',4''}$=9.6 Hz, $J_{4'',5''}$=9.0 Hz, $J_{4'',4''OH}$=6.0 Hz, 1H, 4''-H], 3.61 (dd, $J_{6'',6''OH}$=5.4 Hz, $J_{gem}$=10.2 Hz, 1H, 6''-H$_a$), 3.38 [t, J=5.4 Hz, 6''-OH (exchangeable with D$_2$O)], 4.95 (dd, $J_{2'',3''}$=9.0 Hz, $J_{1'',2''}$=7.8 Hz, 1H, 2''-H), 5.07 (dd, $J_{3'',4''}$=9.6 Hz, $J_{2'',3''}$=9.0 Hz, 1H, 3''-H), 5.44 [d, J=6.6 Hz, 1H, 4''-OH (exchangeable with D$_2$O)], 5.72 (d, $J_{1'',2''}$=7.8 Hz, 1H, 1''-H), 6.20 (d, $^4$J=2.4 Hz, 1H, 8-H), 6.41 (d, $^4$J=2.4 Hz, 1H, 6-H), 6.56 and 6.65 (each d, each 2H, J=9.0 Hz, 4H, 2×3''''-H and 2×5''''-H), 6.84 (d, J=8.4 Hz, 1H, 5'-H), 6.92 and 6.98 (each d, each 2H, J=9.0 Hz, 4H, 2×2''''-H and 2×6''''-H), 7.51 (dd, J=8.4 Hz, $^4$J=2.4 Hz, 1H, 6'-H), 7.56 (d, $^4$J=2.4 Hz, 1H, 2'-H), 9.10 [s, 1H, Ar—OH (exchangeable with D$_2$O)], 9.17 [s, 1H, Ar—OH (exchangeable with D$_2$O)], 9.27 [s, 1H, 3'-OH (exchangeable with D$_2$O)], 9.75 [s, 1H, 4'-OH (exchangeable with D$_2$O)], 10.87 [s, 1H, 7-OH (exchangeable with D$_2$O)], 12.60 [s, 1H, 5-OH (exchangeable with D$_2$O)].

$^{13}$C NMR (DMSO-d$_6$, 600 MHz) δ 31.15 and 31.28 (each C, 2C, 2×2''''-C), 37.33 and 37.41 (each C, 2C, 2×3''''-C), 62.39 (5''-C), 69.53 (6''-C), 74.08 (4''-C), 77.01 (2''-C), 79.14 (3''-C), 95.55 (1''-C), 97.36 (8-C), 100.22 (6-C), 105.93 (4a-C), 116.98 and 117.09 (each C, 4C, 2×3''''-C and 2×5''''-C), 117.26 (2'-C), 118.09 (5'-C), 122.69 (6'-C), 123.59 (3-C), 130.90 and 130.97 (each C, 4C, 2×2''''-C and 2×6''''-C), 132.26 (1'-C), 132.42 (2C, 2×1''''-C), 134.87 (a-C), 146.85 (3'-C), 150.67 (4'-C), 157.52 and 157.58 (each C, 2C, 4''''-C), 158.25 (5-C), 163.21 (1a-C), 166.19 (7-C), 173.16 and 173.67 (each C, 2C, 2×C=O), 178.89 (4-C). MS (FAB, 3-nitrobenzyl alcohol was used as matrix) m/z; 761 ([MH]$^+$). Anal. Calcd for $C_{39}H_{36}O_{16}$: C, 61.58.94; H, 4.77. Found: C, 61.44; H, 4.85.

b) 2-(3',4'-Dihydroxy)-5,7-dihydroxy-3-β-D-(2",3"-di-p-ethoxyphenylethylcarboxy)glucosyl-4H-chromen-4-one (15b)

Yield 0.67 g (81%). Melting point (m.p.) 116-117° C. $R_f$=0.14 (AcOEt). IR (KBr) cm$^{-1}$; 1610 and 1638 (C=C), 1740 (C=O), 3400 (OH).

$^1$H NMR (DMSO-$d_6$, 600 MHz) δ 2.38 and 2.53 (each t, each 2H, J=7.8 Hz, 4H, 2×ArCH$_2$CH$_2$CO), 2.67 and 2.72 (each t, each 2H, J=7.8 Hz, 9H, 2×ArCH$_2$CH$_2$CO), 3.35-3.39 (m, 2H, 5"-H and 6"-H$_b$), 3.48 [ddd (triplet after addition of D$_2$O, J=9.6 Hz), J$_{3",4"}$=9.6 Hz, J$_{4",5"}$=9.0 Hz, J$_{4",4"OH}$=6.0 Hz, 1H, 4"-H], 3.60 (br d, J$_{gem}$=10.8 Hz, 1H, 6"-H$_a$), 3.78 and 3.93 (each q, each 2H, J=7.8 Hz, 4H, 2×OCH$_2$Me), 4.40 [br s, 1H, 6"-OH (exchangeable with D$_2$O)], 4.94 (dd, J$_{1",2"}$=7.8 Hz, J$_{2",3"}$=9.0 Hz, 1H, 2"-H), 5.06 (dd, J$_{2",3"}$=9.0 Hz, J$_{3",4"}$=9.6 Hz, 1H, 3"-H), 5.44 [d, J=6.0 Hz, 1H, 4"-OH (exchangeable with D$_2$O)], 5.72 (d, J$_{1",2"}$=7.8 Hz, 1H, 1"-H), 6.20 (d, $^4$J=1.8 Hz, 1H, 8-H), 6.40 (d, $^4$J=1.8 Hz, 1H, 6-H), 6.64 and 6.80 (each d, each 2H, J=9.0 Hz, 4H, 2×3""-H and 2×5""-H), 6.84 (d, J=8.4 Hz, 1H, 5'-H), 7.01 and 7.10 (each d, each 2H, J=9.0 Hz, 4H, 2×2""-H and 2×6""-H), 7.50 (dd, J=8.4 Hz, $^4$J=2.4 Hz, 1H, 6'-H), 7.55 (d, $^4$J=2.4 Hz, 2'-H), 9.27 [s, 1H, 3'-OH (exchangeable with D$_2$O)], 9.76 [s, 1H, 4'-OH (exchangeable with D$_2$O)], 10.88 [s, 1H, 7-OH (exchangeable with D$_2$O)], 12.59 [s, 1H, 5-OH (exchangeable with D$_2$O)].

$^{13}$C NMR (DMSO-$d_6$, 600 MHz) δ 16.58 and 16.67 (each C, 2C, 2×Me), 31.00 and 31.17 (each C, 2C, 2×2'''-C), 36.99 and 37.16 (each C, 2C, 2×3'''-C), 62.37 (5"-C), 64.64 and 64.80 (each C, 2C, 2×OCH$_2$), 69.55 (6"-C), 74.01 (4"-C), 76.94 (2"-C), 79.15 (3"-C), 95.52 (1"-C), 97.39 (8-C), 100.16 (6-C), 105.92 (4a-C), 115.94 and 116.18 (each C, 4C, 2×3""-C and 2×5""-C), 117.25 (2'-C), 118.05 (5'-C), 122.69 (6'-C), 123.63 (3-C), 130.98 and 131.07 (each C, 4C, 2×2""-C and 2×6""-C), 133.89 and 134.11 (2C, 2×1""-C), 34.84 (2-C), 134.99 (1'-C), 146.86 (3'-C), 150.67 (4'-C), 158.18 (5-C), 158.73 and 158.86 (each C, 2C, 4""-C), 163.22 (1a-C), 166.20 (7-C), 173.14 and 173.59 (each C, 2C, 2×C=O), 178.86 (4-C). MS (FAB, 3-nitrobenzyl alcohol was used as matrix) m/z; 817 ([MH]$^+$). Anal. Calcd for $C_{43}H_{44}O_{16}$: C, 63.23; H, 5.43. Found: C, 63.34; H, 5.50.

c) 2-(3',4'-Dihydroxy)-5,7-dihydroxy-3-β-D-(2",3"-di-p-methylphenylethylcarboxy)glucosyl-4H-chromen-4-one (15c)

Yield 0.62 g (82%). Melting point (m.p.) 126-127° C. $R_f$=0.11 (AcOEt). IR (KBr) cm$^{-1}$; 1610 and 1638 (C=C), 1738 (C=O), 3400 (OH).

$^1$H NMR (DMSO-$d_6$, 600 MHz) 52.10 and 2.22 (each s, each 3H, 6H, 2×ArMe), 1.63 and 1.81 (each t, each 2H, 4H, 2×ArCH$_2$CH$_2$CO), 2.68 and 2.74 (each t, each 2H, J=7.8 Hz, 4H, 2×ArCH$_2$CH$_2$CO), 3.34-3.44 (m, 1H, 5"-H), 3.38 (dd, J$_{6"H,6"OH}$=5.4 Hz, J$_{gem}$=10.2 Hz, 1H, 6"-H$_b$), 3.47 (ddd (triplet after addition of D$_2$O, J=9.6 Hz), J$_{3",4"}$=9.6 Hz, J$_{4",5"}$=9.0 Hz, J$_{4"H,4"OH}$=6.6 Hz, 1H, 4"-H), 3.60 (dd, J$_{6"Ha,6"OH}$=5.4 Hz, J$_{gem}$=10.2 Hz, 1H, 6"-H$_a$), 4.36 [t, J=5.4 Hz, 6"-OH (exchangeable with D$_2$O)], 4.93 (dd, J$_{1",2"}$=7.8 Hz, J$_{2",3"}$=9.0 Hz, 1H, 2"-H), 5.02 (dd, J$_{2",3"}$=9.0 Hz, J$_{3",4"}$=9.6 Hz, 1H, 3"-H), 5.44 [d, J$_{4"H,4"OH}$=6.6 Hz, 1H, 4"-OH (exchangeable with D$_2$O)], 5.69 (d, J$_{1",2"}$=7.8 Hz, 1H, 1"-H), 6.20 (d, $^4$J=2.4 Hz, 1H, 8-H), 6.40 (d, $^4$J=2.4 Hz, 1H, 6-H), 6.83 (d, J=8.4 Hz, 1H, 5'-H), 6.92 and 6.99 (each d, each 2H, J=8.4 Hz, 4H, Ar—H, 2×2""-H, 2×6""-H), 7.04 and 7.08 (each d, each 2H, J=8.4 Hz, 4H, 2×3""-H and 2×5""-H), 7.50 (dd, J=8.4 Hz, $^4$J=2.4 Hz, 1H, 6'-H), 7.56 (d, $^4$J=2.4 Hz, 1H, 2'-H), 9.27 [s, 1H, 3'-OH (exchangeable with D$_2$O)], 9.75 [s, 1H, 4'-OH (exchangeable with D$_2$O)], 10.87 [s, 1H, 7-OH (exchangeable with D$_2$O)], 12.58 [s, 1H, 5-OH (exchangeable with D$_2$O)].

$^{13}$C NMR (DMSO-$d_6$, 600 MHz) δ 22.45 and 22.57 (each C, 2C, 2×ArMe), 31.45 and 31.58 (each C, 2C, 2×2'''-C), 36.82 and 36.91 (each C, 2C, 2×3'''-C), 62.37 (5"-C), 69.54 (6"-C), 74.06 (4"-C), 76.97 (2"-C), 79.13 (3"-C), 95.52 (1"-C), 97.36 (8-C), 100.22 (6-C), 105.93 (4a-C), 117.26 (2'-C), 118.06 (5'-C), 122.69 (6'-C), 123.61 (3-C), 129.90 and 129.96 (each C, 4C, 2×2""-C and 2×6""-C), 130.71 and 130.90 (each C, 4C, 2×3""-C and 2×5""-C), 134.87 (2-C), 134.98 (1'-C), 136.81 and 136.95 (2C, 2×4""-C), 139.09 and 139.27 (2C, 2×1""-C), 146.85 (3'-C), 150.66 (4'-C), 158.23 (5-C), 163.22 (1a-C), 166.18 (7-C), 173.06 and 173.58 (each C, 2C, 2×C=O), 178.85 (4-C). MS (FAB, 3-nitrobenzyl alcohol was used as matrix) m/z; 757 ([MH]$^+$). Anal. Calcd for $C_{41}H_{40}O_{14}$: C, 65.07; H, 5.33. Found: C, 65.02; H, 5.15.

d) 2-(3',4'-Dihydroxy)-5,7-dihydroxy-3-β-D-(2",3"-di-p-flurophenylethylcarboxy)glucosyl-4H-chromen-4-one (15d)

Yield 0.60 g (80%). Melting point (m.p.) 124-125° C. $R_f$=0.13 (AcOEt). IR (KBr) cm$^{-1}$; 1605 and 1638 (C=C), 1738 (C=O), 3410 (OH).

$^1$H NMR (DMSO-$d_6$, 600 MHz) δ 2.42 and 2.56 (each t, each 2H, 4H, 2×ArCH$_2$CH$_2$CO), 2.73 and 2.78 (each t, each 2H, J=7.8 Hz, 4H, 2×ArCH$_2$CH$_2$CO), 3.35-3.37 (m, 1H, 5"-H), 3.39 (dd, J$_{6"Hb,6"OH}$=6.0 Hz, J$_{gem}$=10.8 Hz, 1H, 6"-H$_b$), 3.48 (ddd (triplet after addition of D$_2$O, J=9.6 Hz), J$_{3",4"}$=9.6 Hz, J$_{4",5"}$=9.0 Hz, J$_{4"H,4"OH}$=6.0 Hz, 1H, 4"-H), 3.61 (dd, J$_{6"Ha,6"OH}$=5.4 Hz, J$_{gem}$=10.8 Hz, 1H, 6"-H$_a$), 5.15 [dd, J=5.4 Hz, J=6.0 Hz, 6"-OH (exchangeable with D$_2$O)], 4.94 (dd, J$_{1",2"}$=7.8 Hz, J$_{2",3"}$=9.0 Hz, 1H, 2"-H), 5.08 (t, J=9.6 Hz, 1H, 3"-H), 5.45 [d, J$_{4"H,4"OH}$=6.0 Hz, 1H, 4"-OH (exchangeable with D$_2$O)], 5.70 (d, J$_{1",2"}$=7.8 Hz, 1H, 1"-H), 6.20 (d, $^4$J=2.4 Hz, 1H, 8-H), 6.41 (d, $^4$J=2.4 Hz, 1H, 6-H), 6.84 (d, J=8.4 Hz, 1H, 5'-H), 6.93 and 7.07 (each t, each 2H, each J=9.0 Hz, 4H, Ar—H, 2×3""-H and 2×5""-H), 7.16 and 7.25 (each dd, J=9.0 Hz, J=6.0 Hz, each 2H, 4H, 2×2""-H and 2×6""-H), 7.50 (dd, J=8.4 Hz, $^4$J=2.4 Hz, 1H, 6'-H), 7.55 (d, $^4$J=2.4 Hz, 1H, 2'-H), 9.28 [s, 1H, 3'-OH (exchangeable with D$_2$O)], 9.76 [s, 1H, 4'-OH (exchangeable with D$_2$O)], 10.88 [s, 1H, 7-OH (exchangeable with D$_2$O)], 12.58 [s, 1H, 5-OH (exchangeable with D$_2$O)].

$^{13}$C NMR (DMSO-$d_6$, 600 MHz) δ 31.03 and 31.15 (each C, 2C, 2×2'''-C), 36.79 and 36.87 (each C, 2C, 2×3'''-C), 62.35 (5"-C), 69.52 (6"-C), 74.12 (4"-C), 77.04 (2"-C), 79.11 (3"-C), 95.53 (1"-C), 97.39 (8-C), 100.20 (6-C), 105.92 (4a-C), 116.69-117.02 (4C, 2×3""-C and 2×5""-C), 117.26 (2'-C), 118.07 (5'-C), 122.68 (6'-C), 123.59 (3-C), 131.93 (4C, 2×2""-C and 2×6""-C), 134.84 (2-C), 134.99 (1'-C), 138.29 and 138.47 (2C, 2×1""-C), 146.85 (3'-C), 150.66 (4'-C), 158.58 (5-C), 161.87 and 163.48 (each d, each C, 2C, 2×4""-C), 163.20 (1a-C), 166.19 (7-C), 172.97 and 173.46 (each C, 2C, 2×C=O), 178.85 (4-C). MS (FAB, 3-nitrobenzyl alcohol was used as matrix) m/z; 765 ([MH]$^+$). Anal. Calcd for $C_{39}H_{34}F_2O_{14}$: C, 61.26; H, 4.48. Found: C, 61.39; H, 4.60.

e) 2-(3',4'-Dihydroxy)-5,7-dihydroxy-3-β-D-(2",3"-di-p-ethoxybenzoyloxy)glucosyl-4H-chromen-4-one (15e)

Yield 0.62 g (82%). Melting point (m.p.) 122-123° C. $R_f$=0.10 (AcOEt). IR (KBr) cm$^{-1}$; 1610 and 1638 (C=C), 1720 (C=O), 3410 (OH).

$^1$H NMR (DMSO-d$_6$, 600 MHz) δ 1.30-1.34 (m, 6H, 2×CH$_2$Me), 3.46-3.52 (m, 1H, 5"-H), 3.68 (br d, J$_{gem}$=10.2 Hz, 1H, 6"-H$_b$), 3.67-3.71 (m, 2H, 4"-H and 6"-H$_a$), 4.03-4.10 (m, 4H, 2×OCH$_2$Me), 4.49 [br s, 6"-OH (exchangeable with D$_2$O)], 4.94 (dd, J$_{1'',2''}$=7.8 Hz, J$_{2'',3''}$=9.0 Hz, 1H, 2"-H), 5.08 (dd, J$_{2'',3''}$=9.0 Hz, J$_{3'',4''}$=9.6 Hz, 1H, 3"-H), 5.55 [br s, 1H, 4"-OH (exchangeable with D$_2$O)], 5.96 (d, J$_{1'',2''}$=7.8 Hz, 1H, 1"-H), 6.18 (d, $^4$J=2.4 Hz, 1H, 8-H), 6.35 (d, $^4$J=2.4 Hz, 1H, 6-H), 6.85 (d, J=8.4 Hz, 1H, 5'-H), 6.92 and 6.97 (each d, each 2H, J=9.0 Hz, 4H, 2×3'''-H and 2×5'''-H), 7.53 (dd, J=8.4 Hz, $^4$J=1.8 Hz, 1H, 6'-H), 7.54 (d, $^4$J=2.4 Hz, 1H, 2'-H), 7.76 and 7.82 (each d, each 2H, J=9.0 Hz, 4H, 2×2'''-H and 2×6'''-H), 9.29 [s, 1H, 3'-OH (exchangeable with D$_2$O)], 9.77 [s, 1H, 4'-OH (exchangeable with D$_2$O)], 10.86 [s, 1H, 7-OH (exchangeable with D$_2$O)], 12.56 [s, 1H, 5-OH (exchangeable with D$_2$O)].

$^{13}$C NMR (DMSO-d$_6$, 600 MHz) δ 16.44 (2C, 2×Me), 62.44 (5"-C), 65.49 (2C, 2×OCH$_2$), 69.70 (6"-C), 74.50 (4"-C), 77.41 (2"-C), 79.47 (3"-C), 95.49 (1"-C), 97.39 (8-C), 100.11 (6-C), 105.96 (4a-C), 116.22 (4C, 2×3'''-C and 2×5'''-C), 117.28 (2'-C), 118.06 (5'-C), 122.70 (6'-C), 122.98 (3-C), 123.48 and 123.64 (4C, 2'''-C and 2×6'''-C), 133.34 and 138.38 (2C, 2×1'''-C), 134.80 (2-C), 135.01 (1'-C), 146.87 (3'-C), 150.68 (4'-C), 158.32 (1a-C), 163.17 (5-C), 164.42 and 164.53 (each C, 2C, 2×4'''-C), 166.17 and 166.30 (each C, 2C, 2×C=O), 166.85 (7-C), 178.87 (4-C). MS (FAB, 3-nitrobenzyl alcohol was used as matrix) m/z; 761 ([MH]$^+$). Anal. Calcd for C$_{41}$H$_{44}$O$_{14}$·⅓H$_2$O: C, 61.10; H, 4.82. Found: C, 60.85; H, 4.78.

f) 2-(3',4'-Dihydroxy)-5,7-dihydroxy-3-β-D-(2",3"-di-p-propylbenzoyloxy)glucosyl-4H-chromen-4-one (15f)

Yield 0.59 g (78%). Melting point (m.p.) 152-153° C. R$_f$=0.12 (AcOEt). IR (KBr) cm$^{-1}$; 1610 and 1640 (C=C), 1738 (C=O), 3425 (OH).

$^1$H NMR (DMSO-d$_6$, 600 MHz) δ 0.85 and 0.87 (each t, each 3H, J=7.2 Hz, 6H, 2×CH$_2$Me), 1.53-1.61 (m, 4H, 2×CH$_2$CH$_2$Me), 2.55 and 2.59 (each t, each 2H, J=7.2 Hz, 4H, 2×CH$_2$CH$_2$Me), 3.46-3.53 (m, 2H, 5"-H and 6"-H$_b$), 3.67-3.74 (m, 2H, 4"-H, 6"-H$_a$), 4.50 [t, J=5.4 Hz, 6"-OH (exchangeable with D$_2$O)], 4.94 (dd, J$_{1'',2''}$=7.8 Hz, J$_{2'',3''}$=9.6 Hz, 1H, 2"-H), 5.08 (t, J=9.6 Hz, 1H, 3"-H), 5.55 [d, J=6.6 Hz, 1H, 4"-OH (exchangeable with D$_2$O)], 5.98 (d, J$_{1'',2''}$=7.8 Hz, 1H, 1"-H), 6.18 (d, $^4$J=2.4 Hz, 1H, 8-H), 6.35 (d, $^4$J=2.4 Hz, 1H, 6-H), 6.85 (d, J=8.4 Hz, 1H, 5'-H), 7.24 and 7.28 (each d, each 2H, J=9.0 Hz, 4H, 2×3'''-H and 2×5'''-H), 7.53 (dd, J=8.4 Hz, $^4$J=2.4 Hz, 1H, Ar—H, 6'-H), 7.55 (d, $^4$J=2.4 Hz, 1H, 2'-H), 7.76 and 7.80 (each d, each 2H, J=9.0 Hz, 4H, 2×2'''-H and 2×6'''-H), 9.30 [s, 1H, 3'-OH (exchangeable with D$_2$O)], 9.77 [s, 1H, 4'-OH (exchangeable with D$_2$O)], 10.86 [s, 1H, 7-OH (exchangeable with D$_2$O)], 12.55 [s, 1H, 5-OH (exchangeable with D$_2$O)].

$^{13}$C NMR (DMSO-d$_6$, 600 MHz) δ 15.55 (2C, 2×Me), 25.63 and 25.70 (each C, 2C, 2×CH$_2$), 39.09 (2C, 2×CH$_2$), 62.42 (5"-C), 69.68 (6"-C), 74.69 (4"-C), 77.64 (2"-C), 79.41 (3"-C), 95.49 (1"-C), 97.39 (8-C), 100.09 (6-C), 105.95 (4a-C), 117.28 (2'-C), 118.06 (5'-C), 122.68 (6'-C), 123.62 (3-C), 128.51 and 129.01 (each C, 2C, 2×1'''-C), 130.52 and 130.55 (each C, 4C, 2×3'''-C and 2×5'''-C), 131.27 and 131.32 (each 2C, 4C, 2×2'''-C and 2×6'''-C), 134.78 (2-C), 134.84 (1'-C), 146.86 (3'-C), 150.11 and 150.31 (2C, 2×4'''-C), 150.69 (4'-C), 158.20 (1a-C), 163.16 (5-C), 166.18 and 164.68 (each C, 2C, 2×C=O), 178.85 (4-C). MS (FAB, 3-nitrobenzyl alcohol was used as matrix) m/z; 757 ([MH]$^+$). Anal. Calcd for C$_{41}$H$_{40}$O$_{14}$: C, 65.07; H, 5.33. Found: C, 64.90; H, 5.12.

g) 2-(3',4'-Dihydroxy)-5,7-dihydroxy-3-β-D-(2",3"-di-p-flurobenzoyloxy)glucosyl-4H-chromen-4-one (15g)

Yield 0.54 g (76%). Melting point (m.p.) 152-153° C. R$_f$=0.08 (AcOEt). IR (KBr) cm$^{-1}$; 1610 and 1648 (C=C), 1738 (C=O), 3400 (OH).

$^1$H NMR (DMSO-d$_6$, 600 MHz) δ 3.49 (dd, J$_{6''Hb,6''OH}$=5.4 Hz, J$_{gem}$=10.2 Hz, 1H, 6"-H$_b$), 3.52-3.55 (m, 1H, 5"-H), 3.69 (dd, J$_{6''Ha,6''OH}$=4.8 Hz, J$_{gem}$=10.2 Hz, 1H, 6"-H$_a$), 3.72 (ddd (triplet after addition of D$_2$O, J=9.6 Hz), J$_{3'',4''}$=9.6 Hz, J$_{4'',5''}$=9.0 Hz, J$_{4''H,4''OH}$=6.6 Hz, 1H, 4"-H), 4.51 [t, J=5.4 Hz, 6"-OH (exchangeable with D$_2$O)], 5.29 (dd, J$_{1'',2''}$=7.8 Hz, J$_{2'',3''}$=9.6 Hz, 1H, 2"-H), 5.44 (t, J=9.6 Hz, 1H, 3"-H), 5.64 [d, J=6.6 Hz, 1H, 4"-OH (exchangeable with D$_2$O)], 5.98 (d, J$_{1'',2''}$=7.8 Hz, 1H, 1"-H), 6.18 (d, $^4$J=2.4 Hz, 1H, 8-H), 6.35 (d, $^4$J=2.4 Hz, 1H, 6-H), 6.83 (d, J=8.4 Hz, 1H, 5'-H), 7.27 and 7.32 (each t, each 2H, J=9.0 Hz, 4H, 2×3'''-H and 2×5'''-H), 7.51 (dd, J=8.4 Hz, $^4$J=2.4 Hz, 1H, Ar—H, 6'-H), 7.53 (d, J=2.4 Hz, 1H, 2'-H), 7.89 (each dd, each 2H, J=9.0 Hz, J=5.4 Hz, 4H, 2×2'''-H and 2×6'''-H), 9.28 [s, 1H, 3'-OH (exchangeable with D$_2$O)], 9.76 [s, 1H, 4'-OH (exchangeable with D$_2$O)], 10.87 [s, 1H, 7-OH (exchangeable with D$_2$O)], 12.55 [s, 1H, 5-OH (exchangeable with D$_2$O)].

$^{13}$C NMR (DMSO-d$_6$, 600 MHz) δ 55.46 (5"-C), 61.12 (6"-C), 73.82 (4"-C), 76.86 (2"-C), 78.03 (3"-C), 94.26 (1"-C), 96.14 (8-C), 99.00 (6-C), 104.70 (4a-C), 116.04-116.82 (4C, 2×3'''-C and 2×5'''-C), 121.37 (2'-C), 122.33 (5'-C), 126.24 (6'-C), 126.73 (3-C), 132.80-132.94 (4C, 2×2'''-C and 2×6'''-C), 133.67 (2-C), 133.94 (1'-C), 145.61 (3'-C), 149.46 (4'-C), 156.96 and 156.97 (2C, 2×1'''-C), 158.34 (5-C), 164.52 and 164.95 (each d, each C, 2C, 2×4'''-C), 165.11 (7-C), 166.78 and 166.82 (each C, 2C, 2×C=O), 177.57 (4-C). MS (FAB, 3-nitrobenzyl alcohol was used as matrix) m/z; 709 ([MH]$^+$).

h) 2-(3',4'-Dihydroxy)-5,7-dihydroxy-3-β-D-(2",3"-di-p-flurobenzyloxy)glucosyl-4H-chromen-4-one (15h)

Yield 0.57 g (77%). Melting point (m.p.) 128-129° C. R$_f$=0.10 (AcOEt). IR (KBr) cm$^{-1}$; 1610 and 1648 (C=C), 1740 (C=O), 3400 (OH).

$^1$H NMR (CDCl$_3$, 600 MHz) δ 3.34-3.60 (m, 4H, 5"-H, 6"-H and 4"-H), 3.45/3.55 and 3.55/3.62 (each AB system, each dd, each 2H, each J$_{AB}$=15.6 Hz, 4H, 2×ArCH$_2$CO), 4.38 [dd, J=5.4 Hz, J=4.8 Hz, 6"-OH (exchangeable with D$_2$O)], 4.96 (dd, J$_{2'',3''}$=9.6 Hz, J$_{1'',2''}$=7.8 Hz, 1H, 2"-H), 5.08 (dd, J$_{3'',4''}$=9.0 Hz, J$_{2'',3''}$=9.6 Hz, 1H, 3"-H), 5.48 [d, J=6.6 Hz, 1H, 4"-OH (exchangeable with D$_2$O)], 5.71 (d, J$_{1'',2''}$=7.8 Hz, 1H, 1"-H), 6.21 (d, $^4$J=2.4 Hz, 1H, 8-H), 6.41 (d, $^4$J=2.4 Hz, 1H, 6-H), 6.84 (d, J=8.4 Hz, 1H, 5'-H), 7.04 and 7.12 (each t, each 2H, each J=9.0 Hz, 4H, 2×3''''-H and 2×5''''-H), 7.18 and 7.23 (each dd, each 2H, each J=8.4 Hz, each J=9.0 Hz, 4H, 2×2''''-H and 2×6''''-H), 7.51 (dd, J=8.4 Hz, $^4$J=2.4 Hz, 1H, 6'-H), 7.56 (d, $^4$J=2.4 Hz, 1H, 2'-H), 9.27 [s, 1H, 3'-OH (exchangeable with D$_2$O)], 9.75 [s, 1H, 4'-OH (exchangeable with D$_2$O)], 10.88 [s, 1H, 7-OH (exchangeable with D$_2$O)], 12.59 [s, 1H, 5-OH (exchangeable with D$_2$O)].

$^{13}$C NMR (DMSO-d$_6$, 600 MHz) δ 33.72 (1'''-C), 61.09 (5"-C), 68.29 (6"-C), 73.14 (4"-C), 76.10 (2"-C), 77.79 (3"-C), 94.32 (1"-C), 96.14 (8-C), 99.07 (6-C), 104.68 (4a-C), 115.62-115.87 (4C, 2×3''''-C and 2×5''''-C), 121.37 (2'-C), 126.86 (5'-C), 121.42 (6'-C), 122.33 (3-C), 130.65 and 130.97

(2C, 2×1''''-C), 131.91-131.98 (4C, 2×2''''-C and 2×6''''-C), 133.63 (2-C), 134.23 (1'-C), 145.60 (3'-C), 149.44 (4'-C), 157.34 (5-C), 161.14 (1a-C), 161.98 and 162.75 (each d, each C, 2C, 2×4''''-C), 164.97 (7-C), 170.67 and 171.13 (each C, 2C, 2×C=O), 177.62 (4-C). MS (FAB, 3-nitrobenzyl alcohol was used as matrix) m/z; 737 ([MH]$^+$).

16) 2-(3'4'-Dihydroxy)-5,7-dihydroxy-3-β-D-tetraacetylglucosyl-4H-chromen-4-one (16)

Yield 0.45 g (71%). Melting point (m.p.) 109-110° C. (lit. 108-110° C.). $R_f$=0.36 (AcOEt:n-hexane, 1:4, v/v). IR (KBr) cm$^{-1}$; 1600 and 1640 (C=C), 1745 (C=O).

$^1$H NMR (DMSO-d$_6$, 300 MHz) δ 1.95, 2.01, 2.11 and 2.40 (each s, 12H, 4×Me), 3.63-3.68 (m, 1H, 5-H), 3.94-4.13 (m, 2H, 6-H), 5.14-5.34 (m, 3H, 2-H, 3-H, and 4-H), 5.61 (d, J=7.8 Hz, 1H, 1-H), 6.29 (d, J=2.4 Hz, 1H, 8-H), 6.39 (d, J=2.1 Hz, 1H, 6-H), 6.94 (d, J=8.4 Hz, 1H, 5'-H), 7.45 (d, 1H, J=8.4 Hz, Ar—H), 7.72 (d, $^4$J=2.1 Hz, 1H, Ar—H), 7.99 [s, 1H, 3'-OH (exchangeable with D$_2$O)], 8.22 [s, 1H, 4'-OH (exchangeable with D$_2$O)], 9.98 [s, 1H, 7-OH (exchangeable with D$_2$O)], 12.54 [s, 1H, 5-OH (exchangeable with D$_2$O)].

17) 2-(3'4'-Dihydroxy)-5,7-dihydroxy-3-β-D-glucosyl-4H-chromen-4-one (17)

Yield 0.30 g (65%). Melting point (m.p.) 173-174° C. (lit. 172-174° C.). $R_f$=0.17 (AcOEt). IR (KBr) cm$^{-1}$; 1600 and 1640 (C=C), 1750 (C=O), 3425 (OH).

$^1$H NMR (DMSO-d$_6$, 300 MHz) δ 3.08 (br s, 2H, 5-H and 6''-H$_b$), 3.22 (br s, 2H, 6-H$_a$ and 4''-H), 3.31-3.59 (m, 2H, 2-H and 3-H), 4.23 [br s, 1H, 6''-OH (exchangeable with D$_2$O)], 4.93 [br s, 1H, 2''-OH (exchangeable with D$_2$O)], 5.05 [br s, 1H, 3''-OH (exchangeable with D$_2$O)], 5.26 [br s, 1H, 4''-OH (exchangeable with D$_2$O)], 5.44 (d, J=7.5 Hz, 1H, 1-H), 6.18 (d, $^4$J=1.8 Hz, 1H, 8-H), 6.39 (d, $^4$J=1.8 Hz, 1H, 6-H), 6.83 (d, J=9.0 Hz, 1H, 5'-H), 7.55-7.59 (m, 2H, Ar—H), 9.19 [s, 1H, 3'-OH (exchangeable with D$_2$O)], 9.68 [s, 1H, 4'-OH (exchangeable with D$_2$O)], 10.82 [s, 1H, 7-OH (exchangeable with D$_2$O)], 12.63 [s, 1H, 5-OH (exchangeable with D$_2$O)].

Experimental Example 1-1

In Vitro Infectivity Assay (MIC)

The antibacterial activities of the final compounds shown in Example 1-12 were examined. Conventional antibacterial drugs, quercetin, vancomycin, and norfloxacin, were used as controls.

The antibacterial activities were measured based on broth dilution techniques of international standards (Clinical Laboratory Standards Institute: CLSI). The activities were shown by minimum inhibitory concentrations (MICs) determined by inoculating the above-mentioned strains at a concentration of about 10$^5$ CUF/100 mL into Mueller-Hinton broth (manufactured by Difco) containing 0.85% NaCl in 96-well microplates and incubating the plates at 35° C. for 24 hours. Measurement was carried out three times.

The antibacterial activities of the compounds of the present invention against various strains such as methicillin-resistant *Staphylococcus aureus* (MRSA), vancomycin intermediate-resistant *Staphylococcus aureus* (VISA), methicillin-sensitive *Staphylococcus aureus* (MSSA), and vancomycin-resistant enterococci (VRE) were examined. Of the bacteria used in MIC measurement in this test example, clinical bacteria of MRSA (OM481 strain and OM584 strain) were supplied from Okayama University Hospital (Japan). An MRSA strain N315, a vancomycin intermediate-resistant *Staphylococcus aureus* (VISA) strain Mu50, and a methicillin-sensitive *Staphylococcus aureus* (MSSA) strain FDA 209P were used as controls. Vancomycin-resistant *enterococcus* (VRE) strains NCTC 12201 and FN-1 were supplied from the National Institute of Infectious Disease (Japan).

Table 1 below shows the results. The results reveal that the novel flavanone derivatives of the present invention, in particular, the compounds 15a to 15h, have excellent antibacterial activities against the strains. In particular, the compounds 15d, 15c, and 15h were found to have strong antibacterial activities against the vancomycin resistant bacteria such as VRE and VISA.

TABLE 1

Antibacterial activity of compounds against various bacterial strains

| Compound number (FIG. 2) | MIC (μg/mL) | | | | | | |
|---|---|---|---|---|---|---|---|
| | MRSA | | | MSS | VRE | | VISA |
| | OM58 | OM481 | N315 | 209P | FN-1 | NCTC12201 | Mu50 |
| 15a | 4 | 4 | 4 | 4 | 8 | 8 | 4 |
| 15b | 8 | 4 | 2 | 2 | 8 | 8 | 4 |
| 15c | 2 | 2 | 1 | 1 | 2 | 4 | 1 |
| 15d | 2 | 2 | 0.25 | 0.25 | 1 | 1 | 1 |
| 15e | 32 | 32 | 8 | 8 | 16 | 16 | 16 |
| 15f | 32 | 32 | 8 | 8 | 8 | 8 | 16 |
| 15g | 16 | 16 | 2 | 2 | 8 | 8 | 2 |
| 15h | 8 | 8 | 2 | 2 | 8 | 8 | 2 |
| 16 | 128 | 128 | 128 | 128 | >128 | >128 | >128 |
| 17 | >128 | >128 | >128 | >128 | >128 | >128 | >128 |
| Quercetin | >128 | >128 | >128 | >128 | >128 | >128 | >128 |
| Vancomycin | 0.25 | 0.25 | 0.25 | 0.25 | >128 | >128 | 8 |
| Norfloxacin | 64 | 128 | 2 | 0.5 | — | — | — |

Experimental Example 1-2

Determination of DNA Gyrase Inhibition ($IC_{50}$)

As a kit for measurement of DNA gyrase of *Escherichia coli*, a product purchased from John Innes Enterprises (Gyrase Supercoiling assay kit #K0001) was used. Relaxed DNA was modified with gyrase into supercoiled DNA, and reaction products were separated by electrophoresis depending on the sizes of the molecular weights to examine anti-gyrase effects ($IC_{50}$). One unit (1 U) of DNA gyrase and 0.5 mg of relaxed pBR322 DNA were added to 30 mL of the reaction solution, and the mixture was allowed to react at 37° C. for 30 minutes in the presence of 35 mM Tris-HCl (pH 7.5), 24 mM KCl, 4 mM $MgCl_2$, 2 mM DTT, 1.8 mM spermidine, 1 mM ATP, 6.5% (w/v) glycerol, and 0.1 mg/ml BSA. The reactions were stopped using 8 mL of a reaction stop solution (40% sucrose, 100 mM Tris-HCl (pH 7.5), 1 mM EDTA, 0.5 mg/ml bromophenol blue). The $IC_{50}$ value means a concentration required for 50% inhibition of the supercoiling activity.

Table 2 below shows the results. The results reveal that, of the novel flavanone derivatives of the present invention, the compound 15d has an inhibitory effect equal to or greater than that of an existing gyrase inhibitor such as norfloxacin. One example of action mechanisms of the antibacterial agent includes a gyrase inhibitory effect, and other examples thereof include inhibition of synthesis of a protein or a nucleic acid by destroying only cell walls or only cell membranes, and inhibition of actions of various enzymes in a metabolism system. This test example shows that, of the novel flavanone derivatives of the present invention, the compound 15d inhibits gyrase.

TABLE 2

Gyrase inhibitory activity of compounds

| Compound number (FIG. 2) | $IC_{50}$ (μg/ml) |
| --- | --- |
| 15a | 2.54 |
| 15b | 9.23 |
| 15c | 3.50 |
| 15d | 0.22 |
| 15e | 8.24 |
| 15f | 10.02 |
| 15g | 4.25 |
| 15h | 2.04 |
| 16 | >12 |
| 17 | >12 |
| Quercetin | 0.79 |
| Norfloxacin | 0.29 |

Example 2

Synthesis of Galactose Derivative

The properties of the synthesis products were measured by the following methods. Melting points were measured using a Yanaco micro melting point apparatus, and correction was not carried out. IR spectra were measured by a KBr method using a JASCO FT/IR-350 spectrophotometer. Mass spectra were measured at 70 eV by a FAB method using VG-70SE. As a matrix, 3-nitrobenzyl alcohol was used. $^1$H NMR and $^{13}$C NMR spectra were measured using VXR 300, VXR 500, or VXR 600 ($^1$H: 300 MHz, 500 MHz, 600 MHz, $^{13}$C: 150 MHz). The chemical shift of $^1$H NMR is shown by ppm based on TMS in $CDCl_3$ or DMSO (0.00 ppm), while the chemical shift of $^{13}$C is shown by ppm based on a signal of DMSO used as a solution. The coupling constant (J value) is shown by Hz. The elemental analysis was performed using Yanaco CHN Corder MT-5. All reagents were commercially available products and used immediately after opening, and further purification of the reagents was not carried out. The progress of reactions was followed by TLC (silica gel 60 $F_{254}$ manufactured by Merck & Co., Inc. or 70 FM plate manufactured by Wako Pure Chemical Industries, Ltd.). Flash column chromatography was carried out using silica gel 60 (spherical shape, 0.063 to 0.200 mm, Kanto Chemical Co. Inc.). The reaction temperature was adjusted based on the temperature of an oil bath. Dry DMF was dried using 4 Angstrom molecular sieves and distilled before use.

Example 2-1

Synthesis and Identification of Intermediates 3-6 for Galactose Derivative (FIG. 3)

a) 2-(2,2-Diphenylbenzo[d][1,3]dioxol-5-yl)-5,7-dihydroxy-3-β-D-tetraacetylgalactosyl-4H-chromen-4-one (3)

2-(2,2-Dephenylbenzo[d][1,3]dioxol-5-yl)-3,5,7-trihydroxy-4H-chromen-4-one (0.3 g, 0.64 mmol), 2,3,4,6-tetra-O-acetyl-D-glucopyranosyl bromide (0.4 g, 0.97 mmol), and anhydrous $K_2CO_3$ (0.12 g, 0.87 mmol) were stirred in dry DMF (10 mL) at 0° C. for 5 hours under atmosphere of argon. After the reaction, cold water (20 mL) was poured into the mixture, and a pale-yellow precipitate was separated by filtration. The resultant crude product was purified by flash column chromatography using silica gel, to thereby obtain a colorless fine powder of 2 (64%) from a fraction eluted with EtOAc and n-hexane (1.25:2): Melting point (m.p.) 129-130° C.; IR (KBr) υ 1612 $cm^{-1}$ (C=C), 1640 and 1750 $cm^{-1}$ (C=O); $^1$H NMR ($CDCl_3$, 300 MHz) δ 1.90, 2.00, 2.01 and 2.14 (each s, each 3H, 4×$CH_3$CO), 3.84-3.91 (m, 3H, 3"-H, 4"-H, 5"-H), 5.09 (dd, $J_{5'',6''Hb}$=3.0 Hz, $J_{gem}$=10.8 Hz, 1H, 6"-Hb), 5.35 (d, $J_{5'',6''Ha}$=3.6 Hz, 1H, 6"-Ha), 5.41 (dd, $J_{1'',2''}$=7.8 Hz, $J_{2'',3''}$=7.2 Hz, 1H, 2"-H), 5.53 (d, $J_{1'',2''}$=7.8 Hz, 1H, 1"-H), 6.25 (d, $^4$J=1.8 Hz, 1H, 8-H), 6.35 (d, $^4$J=2.4 Hz, 1H, 6-H), 6.96 (d, J=8.1 Hz, 1H, 5'-H), 7.37-7.42 (m, 6H, PhH), 7.58-7.61 (m, 5H, PhH), 7.67 (dd, J=8.4 Hz, $^4$J=2.4 Hz, 1H, 6'H), 7.70 (d, $^4$J=2.4 Hz, 1H, 2'-H), 12.52 (s, 1H, 5-OH, D2O exch.); FAB-MS m/z $MH^+$ ion=797.

b) 2-(2,2-Diphenylbenzo[d][1,3]dioxol-5-yl)-5-hydroxy-3,7-di-β-D-octaacetylgalactosyl-4H-chromen-4-one (4)

IR (KBr) υ 1609 $cm^{-1}$ (C=C), 1638 and 1748 $cm^{-1}$ (C=O); $^1$H NMR ($CDCl_3$, 600 MHz) δ 1.91, 2.00, 2.01, 2.02, 2.07, 2.08, 2.12 and 2.19 (each s, each 3H, 8×$CH_3$CO), 3.83-3.84 (m, 1H, 5"-H), 3.88-3.89 (m, 2H, 3"-H, 4"-H), 4.10-4.14 (m, 1H, 5'"-H), 4.20-4.23 (m, 2H, 3'"-H, 4'"-H), 5.091 (dd, $J_{5'',6''Hb}$=3.6 Hz, $J_{gem}$=10.8 Hz, 1H, 6"-Hb), 5.13 (dd, $J_{5''',6'''Hb}$=3.6 Hz, $J_{gem}$=12.0 Hz, 1H, 6'"-Hb), 5.35 (d, $J_{5'',6''Ha}$=3.6 Hz, 1H, 6"-Ha), 5.41 (dd, $J_{1'',2''}$=7.8 Hz, $J_{2'',3''}$=7.2 Hz, 1H, 2"-H), 5.48 (d, $J_{5''',6'''Ha}$=3.6 Hz, 1H, 6'"-Ha), 5.52 (dd, $J_{1''',2'''}$=8.4 Hz, $J_{2''',3'''}$=7.8 Hz, 1H, 2'"-H), 5.54 (d, $J_{1'',2''}$=7.8 Hz, 1H, 1"-H), 5.56 (d, $J_{1''',2'''}$=7.8 Hz, 1H, 1'"-H), 6.43 (d, $^4$J=1.8 Hz, 1H, 8-H), 6.56 (d, $^4$J=2.4 Hz, 1H, 6-H), 6.98 (d, J=8.1 Hz, 1H, 5'H), 7.26-7.42 (m, 6H, PhH), 7.57-7.61 (m, 5H, PhH), 7.69 (dd, J=8.4 Hz, $^4$J=2.4 Hz, 1H, 6'-H), 7.71 (d, $^4J$=2.4 Hz, 1H, 2'-H), 12.49 (s, 1H, 5-OH, D2O exch.); FAB-MS m/z MH$^+$ ion=1127.

c) 2-(3',4'Dihydroxyphenyl)-5-hydroxy-3,7-di-β-D-octaacetylgalactosyl-4H-chromen-4-one (5)

Yield 69%; Melting point (m.p.) 160-162° C.; IR (KBr) υ 1602 cm$^{-1}$ (C═C), 1651 and 1749 cm$^{-1}$ (C═O), 3462 cm$^{-1}$ (OH); $^1$H NMR (CDCl$_3$, 600 MHz) δ 1.78, 1.93, 1.95, 1.98, 2.03, 2.04, 2.13, and 2.14 (each s, each 3H, 8×CH$_3$CO), 3.82-3.88 (m, 2H, 3''-H, 5''-H), 4.07-4.13 (m, 2H, 3'''-H, 5'''-H), 4.18 (dd, $J_{1'',2''}$=7.2 Hz, $J_{2'',3''}$=6.0 Hz, 1H, 2''-H), 4.51 (dd, $J_{1''',2'''}$=7.2 Hz, $J_{2''',3'''}$=6.0 Hz, 1H, 2'''-H), 5.18-5.22 (m, 3H, 4''-H, 6''-H), 5.23-5.27 (m, 2H, 4'''-H, 6'''-Ha), 5.36 (br s, d, 1H, 6'''-Hb), 5.63 (d, $J_{1'',2''}$=7.2 Hz, 1H, 1''-H), 5.68 (d, $J_{1''',2'''}$=7.2 Hz, 1H, 1'''-H), 6.42 (d, $^4J$=1.8 Hz, 1H, 8-H), 6.73 (d, $^4J$=2.4 Hz, 1H, 6-H), 6.86 (d, J=8.1 Hz, 1H, 5'-H), 7.50 (d, $^4J$=1.8 Hz, 1H, 2'-H), 7.51 (dd, J=8.4 Hz, $^4J$=2.4 Hz, 1H, 6'-H), 9.15 (s, 1H, 3'-OH, D2O exch.), 9.92 (s, 1H, 4'-OH, D2O exch.), 12.62 (s, 1H, 5-OH, D2O exch.); FAB-MS m/z MH$^+$ ion=963.

d) 2-(3',4'-Dihydroxyphenyl)-5-hydroxy-3,7-di-β-D-galactosyl-4H-chromen-4-one (6)

Yield 72%; Melting point (m.p.) 215-217° C.; IR (KBr) υ 1599 cm$^{-1}$ (C═C), 1654 (C═O), 3396 cm$^{-1}$ (C═C); $^1$H NMR (CDCl$_3$, 600 MHz) δ 3.25-3.31 (m, 1H, 5''-H), 3.34-3.37 (m, 2H, 3'''-H, 4''-H), 3.40-3.44 (m, 1H, 5'''-H), 3.45-3.50 (m, 2H, 3'''-H, 4'''-H), 3.52-3.61 (m, 3H, 2''-H, 6''-H), 3.63-3.700 (m, 3H, 2'''-H, 6'''-H), 4.42 (d, J=4.2 Hz, 1H, 2''-OH, D2O exch.), 4.45 (dd, J=4.8 Hz, J=6.0 Hz, 1H, 6''-OH, D2O exch.), 4.55 (d, J=4.8 Hz, 1H, 2'''-H), 4.68 (dd, J=5.4 Hz, J=6.0 Hz, 1H, 6'''-OH, D2O exch.), 4.86 and 4.91 (each d, each 1H, J=6.0 Hz, 2H, 2''-H, 3''-H), 5.02 (d, $J_{1'',2''}$=7.8 Hz, 1H, 1''-H), 5.12 and 5.25 (each d, each 1H, each J=5.4 Hz, 2H, 3'''-H, 4'''-H), 5.40 (d, $J_{1''',2'''}$=7.8 Hz, 1H, 1'''-H), 6.43 (d, $^4J$=1.8 Hz, 1H, 8-H), 6.73 (d, $^4J$=2.4 Hz, 1H, 6-H), 6.82 (d, J=8.1 Hz, 1H, 5'-H), 7.53 (d, $^4J$=1.8 Hz, 1H, 2'-H), 7.67 (dd, J=8.4 Hz, $^4J$=2.4 Hz, 1H, 6'-H), 9.14 (s, 1H, 3'-OH, D$_2$O exch.), 9.75 (s, 1H, 4'-OH, D$_2$O exch.), 12.49 (s, 1H, 5-OH, D$_2$O exch.); FAB-MS m/z MH$^+$ ion=627; Anal. Calcd for C$_{27}$H$_{30}$O$_{17}$: C, 51.76; H, 4.83. Found: C, 52.07; H, 4.94.

Example 2-2

Synthesis and Identification of Intermediate 7 for Galactose Derivative (FIG. 3)

5,7-Dibenzyloxy-2-(2,2-diphenylbenzo[d][1,3]dioxol-5-yl)-3-β-D-tetraacetylgalactosyl-4H-chromen-4-one (7)

Benzene bromide (3.0 mmol) was added to a mixture of 3 (1.0 g, 1.26 mmol) and anhydrous K$_2$CO$_3$ (3 mmol) in dry DMF (10 mL). Then, the mixture was stirred at room temperature for 10 hours. After completion of the reaction, cold water was added to the reaction mixture, and the resultant solid was collected by filtration, washed with water, and then dried. The resultant crude product was recrystallized from a mixed solvent of EtOAc and n-hexane, to thereby obtain a colorless powder 7 (1.08 g, 88%): IR (KBr) υ 1603 cm$^{-1}$ (C═C), 1612 and 1728 cm$^{-1}$ (C═O); $^1$H NMR (CDCl$_3$, 300 MHz) δ 1.90, 2.00, 2.15 and 2.19 (each s, each 3H, 4×CH$_3$CO), 3.84-3.90 (m, 1H, 5''-H), 4.09-4.18 (m, 1H, 5'''-H), 5.09 (dd, 3H, $J_{2'',3''}$=8.4 Hz, $J_{3'',4''}$=6.6 Hz, 1H, 3''-H), 5.10 and 5.27 (each s, each 2H, 2×CH$_2$Ph), 5.33-5.51 (m, 2H, 2''-H, 4''-H), 5.72 (d, $J_{1'',2''}$=7.8 Hz, 1H, 1''-H), 6.41 (d, $^4J$=2.4 Hz, 1H, 8-H), 6.62 (d, $^4J$=2.4 Hz, 1H, 6-H), 6.97 (d, J=8.4 Hz, 1H, 5'-H), 7.37-7.43 (m, 14H, PhH), 7.56-7.61 (m, 6H, PhH), 7.68 (d, $^4J$=2.4 Hz, 1H, 2'-H), 7.70 (dd, J=8.4 Hz, $^4J$=2.4 Hz, 1H, 6'-H).

Example 2-3

Synthesis and Identification of Intermediate 8 for Galactose Derivative (FIG. 3)

5,7-Dibenzyloxy-2-(2,2-diphenylbenzo[d][1,3]dioxol-5-yl)-3-β-D-galactosyl-4H-chromen-4-one (8)

MeONa (0.10 g, 1.80 mmol) was added to a solution obtained by dissolving 7 (1.0 g, 1.20 mmol) in a mixed solvent of EtOAc-MeOH (1:1, 20 mL), and the solution was stirred at room temperature for 30 minutes. After completion of the reaction, the solution was neutralized using an ion-exchange resin Dowex 50 (H$^+$), to thereby obtain a colorless powder 8 (80%): IR (KBr) υ 1600 cm$^{-1}$ (C═C), 1620 cm$^{-1}$ (C═O), 3410 cm$^{-1}$ (OH); $^1$H NMR (DMSO, 300 MHz) δ 3.31-3.66 (m, 5H, 3''-H, 4''-H, 5''-H, 6''-H), 3.66, 4.45, 6.71 and 6.98 (each br s, 4H, 2''-OH, 3''-OH, 4''-OH, 6''-OH, each D$_2$O exch.), 5.24 and 5.27 (each s, each 2H, 2×CH$_2$Ph), 5.26-5.30 (m, 2H, 2''-H, 1''-H), 7.13 (d, $^4J$=2.1 Hz, 1H, 8-H), 7.16 (d, $^4J$=2.1 Hz, 1H, 6-H), 7.30 (d, J=8.1 Hz, 1H, 5'-H), 7.32-7.48 (m, 14H, PhH), 7.55-7.61 (m, 6H, PhH), 7.85 (dd, J=8.4 Hz, $^4J$=2.4 Hz, 1H, 6'-H), 7.92 (d, $^4J$=2.4 Hz, 1H, 2'-H); Anal. Calcd for C$_{48}$H$_{40}$O$_{12}$: C, 71.28; H, 4.98. Found: C, 71.56; H, 4.84.

Example 2-4

Synthesis and Identification of Intermediate 9 for Galactose Derivative (FIG. 3)

5,7-Dibenzyloxy-2-(2,2-diphenylbenzo[d][1,3]dioxol-5-yl)-3-β-D-(3'',4''-O-isopropylidene)glucosyl-4H-chromen-4-one (9)

Concentrated sulfuric acid (1 drop) was added to a mixture of 5,7-dibenzyloxy-2-(2,2-diphenylbenzo[d][1,3]dioxol-3-β-D-glucosyl-4H-chromen-4-one 8 (1.0 g, 1.24 mmol), dry acetone (50 mL), and anhydrous copper sulfate (2.0 g) in a 300-mL flask. Then, the flask was sealed and allowed to stand at room temperature for 24 hours. During this procedure, the reaction mixture was shaken several times. After completion of the reaction, copper sulfate was removed by filtration, and the filtrate was concentrated to about 3 mL. n-Hexane was added to the concentrate, and the resultant solid was collected by filtration, to thereby obtain 9 (60%) as a colorless crystalline powder: IR (KBr) υ 1598 cm$^{-1}$ (C═C), 1615 cm$^{-1}$ (C═O), 3402 cm$^{-1}$ (OH); $^1$H NMR (DMSO-d6, 600 MHz): δ 1.27 and 1.44 (each s, each 3H, 2×CH$_3$), 3.36-3.41 (m, 1H, 5''-H), 3.39-3.72 (m, 2H, 2''-H, 3''-H), 3.53 (ddd, $J_{5'',6''Hb}$=5.4 Hz, $J_{6''Hb,6''OH}$=4.8 Hz, $J_{gem}$=9.6 Hz, 1H, 6''-Hb), 4.08 (dd, $J_{3'',4''}$=6.6 Hz, $J_{3'',4''}$=5.4 Hz, 1H, 4''-H), 4.65 (t, J=4.8 Hz, 1H, 6''-OH, D$_2$O exch.), 5.23 and 5.24 (each s, each 2H, 2×CH$_2$Ph), 5.46 (d, $J_{1'',2''}$=7.8 Hz, 1H, 1''-H), 5.72 (d, J=4.8 Hz, 1H, 2''-OH, D$_2$O exch.), 5.80 (d, J=4.2 Hz, 1H, 2''-OH, D$_2$O exch.), 6.71 (d, 4J=2.4 Hz, 1H, 8-H), 6.96 (d, $^4J$=2.4 Hz, 1H, 6-H), 7.17 (d, J=7.8 Hz, 1H, 5'-H), 7.42-7.49 (m, 14H, PhH), 7.53-7.56 (m, 6H, PhH), 7.73 (dd, J=8.4 Hz, $^4J$=2.4 Hz, 1H, 6'-H), 7.96 (d, $^4J$=2.4 Hz, 1H, 2'-H); FAB-MS m/z MH$^+$ ion=849; Anal. Calcd for C$_{51}$H$_{44}$O$_{12}$: C, 72.16; H, 5.22. Found: C, 71.89; H, 5.06.

Example 2-5

Synthesis and Identification of Intermediates 10a-m for Galactose Derivative (FIG. 3)

A mixture of 9 (0.85 g, 1 mmol), an aliphatic or aromatic carboxylic acid (3 mmol), DCC (0.62 g, 3 mmol), and DMAP (0.36 g, 3 mmol) in dry dichloromethane (10 mL) was stirred under an argon stream at −10° C. for 1 hour, and further stirred at °C. to room temperature for 5 to 7 hours. It should be noted that, in the cases of 10l-m, 1.0 mmol of DCC and 0.8 mmol of DMAP were used. After completion of the reaction, a white precipitate was removed by filtration, and the filtrate was washed twice with 50 mL of 0.5 M citric acid and twice with a 0.5 M sodium hydrogen carbonate solution. The precipitate further generated in this process was removed by filtration. The resultant organic layer was dried over anhydrous sodium sulfate and evaporated at 30° C. under reduced pressure. The residue was purified by flash column chromatography using EtOAc-n-hexane (1:4), to thereby obtain 10a-m as colorless needles.

a) 5,7-Dibenzyloxy-2-(2,2-diphenylbenzo[d][1,3]dioxol-5-yl)-3-β-D-[2",6"-di-O-(4-ethoxybenzoyl)-3",4"-O-isopropylidene]galactosyl-4H-chromen-4-one (10a)

Yield 66%; IR (KBr) υ 1608 cm$^{-1}$ (C=C), 1668 and 1716 cm$^{-1}$ (C=O); $^1$H NMR (CDCl$_3$, 600 MHz) δ 1.32 and 1.60 (each s, each 3H, 2×CH$_3$), 1.36 and 1.41 (each t, each 3H, J=7.2 Hz, 2×CH$_3$CH$_2$), 3.90 and 4.03 (each q, J=7.2 Hz, each 2H, 2×CH$_3$CH$_2$), 4.16-4.19 (m, 1H, 5"-H), 4.24 (dd, $J_{3'',4''}$=5.4 Hz, $J_{4'',5''}$=2.4 Hz, 1H, 4"-H), 4.38 (dd, $J_{5'',6''Hb}$=5.4 Hz, $J_{gem}$=11.4 Hz, 1H, 6"-Hb), 4.38 (dd, $J_{2'',3''}$=7.2 Hz, $J_{3'',4''}$=5.4 Hz, 3"-H), 4.38 (dd, $J_{5'',6''Ha}$=5.4 Hz, $J_{gem}$=11.4 Hz, 1H, 6"-Ha), 5.05 (s, 2H, CH$_2$Ph), 5.20/5.24 (AB system, each d, $J_{AB}$=12.6 Hz, 2H, CH$_2$Ph), 5.45 (dd, $J_{1'',2''}$=7.2 Hz, $J_{2'',3''}$=7.8 Hz, 1H, 2"-H), 5.98 (d, $J_{1'',2''}$=7.2 Hz, 1H, 1"-H), 6.38 (d, $^4$J=2.4 Hz, 1H, 8-H), 6.62 (d, $^4$J=2.4 Hz, 1H, 6-H), 6.62 and 6.84 (each d, each 2H, each J=8.4 Hz, 2×3'"-H, 2×5'"-H), 6.95 (d, J=8.4 Hz, 1H, 5'-H), 7.32-7.41 (m, 14H, PhH), 7.59-7.62 (m, 7H, PhH), 7.71 (dd, J=8.4 Hz, $^4$J=2.4 Hz, 1H, 6'-H), 7.74 and 8.10 (each d, each 2H, each J=9.0 Hz, 2×2'"-H, 2×6'"-H); FAB-MS m/z MH$^+$ ion=1145; Anal. Calcd for C$_{69}$H$_{60}$O$_{16}$: C, 72.37; H, 5.28. Found: C, 72.06; H, 5.19.

b) 5,7-Dibenzyloxy-2-(2,2-diphenylbenzo[d][1,3]dioxol-5-yl)-3-β-D-[2",6"-di-O-(4-propylbenzoyl)-3",4"-O-isopropylidene]galactosyl-4H-chromen-4-one (10b)

Yield 70%; IR (KBr) υ 1608 cm$^{-1}$ (C=C), 1633 and 1742 cm$^{-1}$ (C=O); $^1$H NMR (CDCl$_3$, 600 MHz) δ 0.89-0.92 (each t, each 3H, J=7.2 Hz, 2×CH$_3$CH$_2$), 1.34 and 1.60 (each s, 3H, 2×CH$_3$), 1.55-1.58 (m, 4H, 2×CH$_3$CH$_2$CH$_2$), 2.54 and 2.60 (each t, each 2H, J=7.2 Hz, 2×CH$_3$CH$_2$CH$_2$), 4.17 (ddd, $J_{4'',5''}$=2.4 Hz, $J_{5'',6''Ha}$=4.8 Hz, $J_{5'',6''Hb}$=5.4 Hz, 1H, 5"-H), 4.26 (dd, $J_{3'',4''}$=5.4 Hz, $J_{4'',5''}$=1.8 Hz, 1H, 4"-H), 4.39 (dd, $J_{5'',6''Hb}$=5.4 Hz, $J_{gem}$=11.4 Hz, 1H, 6"-Hb), 4.43 (dd, $J_{2'',3''}$=7.2 Hz, $J_{3'',4''}$=5.4 Hz, 3"-H), 4.39 (dd, $J_{5'',6''Ha}$=4.8 Hz, $J_{gem}$=11.4 Hz, 1H, 6"-Ha), 5.05 (s, 2H, CH$_2$Ph), 5.20/5.22 (AB system, each d, $J_{AB}$=12.6 Hz, 2H, CH$_2$Ph), 5.47 (dd, $J_{1'',2''}$=7.8 Hz, $J_{2'',3''}$=7.2 Hz, 1H, 2"-H), 6.10 (d, $J_{1'',2''}$=7.8 Hz, 1H, 1"-H), 6.39 (d, $^4$J=2.4 Hz, 1H, 8-H), 6.52 (d, $^4$J=2.4 Hz, 1H, 6-H), 6.94 (d, J=8.4 Hz, 1H, 5'-H), 7.00 and 7.19 (each d, each 2H, each J=8.4 Hz, 2×3'"-H, 2×5'"-H), 7.33-7.41 (m, 14H, PhH), 7.59-7.62 (m, 7H, PhH), 7.71 (dd, J=8.4 Hz, $^4$J=2.4 Hz, 1H, 6'-H), 7.74 and 8.08 (each d, each 2H, each J=8.4 Hz, 2×2'"-H, 2×6'"-H); FAB-MS m/z MH$^+$ ion=1141; Anal. Calcd for C$_{71}$H$_{64}$O$_{14}$: C, 74.72; H, 5.65. Found: C, 74.72; H, 5.35.

c) 5,7-Dibenzyloxy-2-(2,2-diphenylbenzo[d][1,3]dioxol-5-yl)-3-β-D-[2",6"-di-O-(4-fluorobenzoyl)-3",4"-O-isopropylidene]galactosyl-4H-chromen-4-one (10c)

Yield 71%; IR (KBr) υ 1604 cm$^{-1}$ (C=C), 1633 and 1730 cm$^{-1}$ (C=O); $^1$H NMR (CDCl$_3$, 600 MHz) δ 1.35 and 1.57 (each s, each 3H, 2×CH$_3$), 4.17 (ddd, $J_{4'',5''}$=2.4 Hz, $J_{5'',6''Ha}$=5.4 Hz, $J_{5'',6''Hb}$=4.8 Hz, 1H, 5"-H), 4.25 (dd, $J_{3'',4''}$=5.4 Hz, $J_{4'',5''}$=2.4 Hz, 1H, 4"-H), 4.43 (dd, $J_{2'',3''}$=7.2 Hz, $J_{3'',4''}$=5.4 Hz, 3"-H), 4.45-4.47 (m, 2H, 6"-H), 5.06 and 5.21 (each s, each 2H, 2×CH$_2$Ph), 5.44 (dd, $J_{1'',2''}$=7.8 Hz, $J_{2'',3''}$=7.2 Hz, 1H, 2"-H), 5.91 (d, $J_{1'',2''}$=7.8 Hz, 1H, 1"-H), 6.42 (d, $^4$J=2.4 Hz, 1H, 8-H), 6.49 (d, $^4$J=2.4 Hz, 1H, 6-H), 6.83 and 7.04 (each t, each 2H, J=9.0 Hz, 2×3'"-H, 2×5'"-H), 6.94 (d, J=8.4 Hz, 1H, 5'-H), 7.35-7.43 (m, 14H, PhH), 7.58-7.62 (m, 8H, PhH), 7.67 (dd, J=8.4 Hz, $^4$J=2.4 Hz, 1H, 6'-H), 7.78 and 8.19 (each dd, each 2H, J=8.4 Hz, J=9.0 Hz, 2×2'"-H, 2×6'"-H); FAB-MS m/z MH$^+$ ion=1093; Anal. Calcd for C$_{65}$H$_{50}$O$_{14}$F$_2$: C, 71.42; H, 4.61. Found: C, 71.71; H, 4.56.

d) 5,7-Dibenzyloxy-2-(2,2-diphenylbenzo[d][1,3]dioxol-5-yl)3-β-D-[2",6"-di-O-(4-methylphenylacetyl)-3",4"-O-isopropylidene]galactosyl-4H-chromen-4-one (10d)

Yield 70%; IR (KBr) υ 1606 cm$^{-1}$ (C=C), 1627 and 1743 cm$^{-1}$ (C=O); $^1$H NMR (CDCl$_3$, 600 MHz) δ 1.25 and 1.48 (each s, each 3H, 2×CH$_3$), 2.23 and 2.26 (each s, each 3H, PhCH$_3$), 3.38/3.41 (AB system, each d, $J_{AB}$=15.6 Hz, 2H, PhCH$_2$CO), 3.72/3.79 (AB system, each d, $J_{AB}$=16.2 Hz, 2H, PhCH$_2$CO), 3.85 (ddd, $J_{4'',5''}$=2.4 Hz, $J_{5'',6''Ha}$=5.4 Hz, $J_{5'',6''Hb}$=4.8 Hz, 1H, 5"-H), 3.99 (dd, $J_{3'',4''}$=5.4 Hz, $J_{4'',5''}$=2.4 Hz, 1H, 4"-H), 4.09 (dd, $J_{5'',6''Hb}$=4.8 Hz, $J_{gem}$=11.4 Hz, 1H, 6"-Hb), 4.14 (dd, $J_{5'',6''Ha}$=5.4 Hz, $J_{gem}$=11.4 Hz, 1H, 6"-Ha), 4.23 (dd, $J_{2'',3''}$=7.2 Hz, $J_{3'',4''}$=5.4 Hz, 1H, 3"-H), 5.06 and 5.27 (each d, each 2H, 2×CH$_2$Ph), 5.20 (dd, $J_{1'',2''}$=7.8 Hz, $J_{2'',3''}$=6.6 Hz, 1H, 2"-H), 5.66 (d, $J_{1'',2''}$=7.8 Hz, 1H, 1"-H), 6.44 (d, $^4$J=2.4 Hz, 1H, 8-H), 6.57 (d, $^4$J=2.4 Hz, 1H, 6-H), 6.90 (d, J=8.4 Hz, 1H, 5'-H), 6.97-7.00 (m, 4H, PhH, 2×3'""-H, 2×5'""-H), 7.05 and 7.20 (each d, J=8.4, each 2H, 2×2'""-H, 2×6'""-H), 7.34-7.40 (m, 14H, PhH), 7.57-7.59 (m, 6H, PhH), 7.64 (d, $^4$J=2.4 Hz, 1H, 2'-H), 7.67 (dd, J=8.4 Hz, $^4$J=1.8 Hz, 1H, 6'-H); FAB-MS m/z MH$^+$ ion=1113; Anal. Calcd for C$_{69}$H$_{60}$O$_{14}$: C, 74.45; H, 5.43. Found: C, 74.61; H, 5.82.

e) 5,7-Dibenzyloxy-2-(2,2-diphenylbenzo[d][1,3]dioxol-5-yl)3-β-D-[2",6"-di-O-(4-fluorophenylacetyl)-3",4"-O-isopropylidene]glucosyl-4H-chromen-4-one (10e)

Yield 70%; IR (KBr) υ 1602 cm$^{-1}$ (C=C), 1626 and 1745 cm$^{-1}$ (C=O); $^1$H NMR (CDCl$_3$, 600 MHz) δ 1.27 and 1.51 (each s, each 3H, 2×CH$_3$), 3.37/3.40 (AB system, each d, $J_{AB}$=15.6 Hz, 2H, PhCH$_2$CO), 3.73/3.81 (AB system, each d, $J_{AB}$=16.2 Hz, 2H, PhCH$_2$CO), 3.88 (ddd, $J_{4'',5''}$=2.4 Hz, $J_{5'',6''Ha}$=5.4 Hz, $J_{5'',6''Hb}$=4.8 Hz, 1H, 5"-H), 4.03 (dd, $J_{3'',4''}$=5.4 Hz, $J_{4'',5''}$=2.4 Hz, 1H, 4"-H), 4.11 (dd, $J_{5'',6''Hb}$=4.8 Hz, $J_{gem}$=11.4 Hz, 1H, 6"-Hb), 4.17 (dd, $J_{5'',6''Ha}$=5.4 Hz, $J_{gem}$=11.4 Hz, 1H, 6"-Ha), 4.24 (dd, $J_{2'',3''}$=7.2 Hz, $J_{3'',4''}$=5.4 Hz, 1H, 3"-H), 5.08 and 5.26 (each d, each 2H, 2×CH$_2$Ph), 5.19 (dd, $J_{1'',2''}$=7.8 Hz, $J_{2'',3''}$=7.2 Hz, 1H, 3"-H), 5.64 (d, $J_{1'',2''}$=7.8 Hz, 1H, 1"-H), 6.46 (d, $^4J$=2.4 Hz, 1H, 8-H), 6.58 (d, $^4J$=2.4 Hz, 1H, 6-H), 6.83 and 6.91 (each t, each J=9.0 Hz, 4H, PhH, 2×3""-H, 2×5""-H), 6.90 (d, J=8.4 Hz, 1H, 5'-H), 7.03 and 7.27 (each dd, J=8.4, J=9.0 Hz, each 2H, 2×2""-H, 2×6""-H), 7.35-7.41 (m, 14H, PhH), 7.56-7.59 (m, 6H, PhH), 7.63 (d, $^4J$=2.4 Hz, 1H, 2'-H), 7.67 (dd, J=8.4 Hz, $^4J$=1.8 Hz, 1H, 6'-H); FAB-MS m/z MH$^+$ ion=1121; Anal. Calcd for $C_{67}H_{54}O_{14}F_2$: C, 71.78; H, 4.85. Found: C, 71.59; H, 4.96.

f) 5,7-Dibenzyloxy-2-(2,2-diphenylbenzo[d][1,3]dioxol-5-yl)-3-β-D-[2",6"-di-O-(4-benzyloxycinnamoyl)-3",4"-O-isopropylidene]galactosyl-4H-chromen-4-one (10f)

Yield 61%; IR (KBr) υ 1602 cm$^{-1}$ (C=C), 1633 and 1715 cm$^{-1}$ (C=O); $^1$H NMR (CDCl$_3$, 500 MHz) δ 1.33 and 1.55 (each s, each 3H, 2×CH$_3$), 4.09 (ddd, $J_{4'',5''}$=2.4 Hz, $J_{5'',6''Ha}$=5.4 Hz, $J_{5'',6''Hb}$=4.8 Hz, 5"-H), 4.21 (dd, $J_{3'',4''}$=5.4 Hz, $J_{4'',5''}$=2.4 Hz, 1H, 4"-H), 4.29-4.34 (m. 2H, 6"-H), 4.36 (dd, $J_{2'',3''}$=7.2 Hz, $J_{3'',4''}$=5.4 Hz, 1H, 3"-H), 4.94/4.97 (AB system, each d, $J_{AB}$=11.4 Hz, 2H, CH$_2$Ph), 5.00, 5.07 and 5.18 (each s, each 2H, 3×CH$_2$Ph), 5.34 (dd, $J_{1'',2''}$=7.8 Hz, $J_{2'',3''}$=7.2 Hz, 1H, 2"-H), 5.89 (d, $J_{1'',2''}$=7.8 Hz, 1H, 1"-H), 6.11 and 6.38 (each d, each 1H, each $J_{trans}$=16.2 Hz, 2×PhCH=CH—), 6.31 (d, $^4J$=1.8 Hz, 1H, 8-H), 6.46 (d, $^4J$=1.8 Hz, 1H, 6-H), 6.88 and 6.92 (each d, each 2H, each J=8.4 Hz, 2×3""-H, 2×5""-H), 6.98 (d, J=9.0 Hz, 1H, 5'-H), 7.31-7.46 (m, 28H, PhH), 7.60-7.63 (m, 6H, PhH), 7.65 and 7.71 (each d, each 1H, each $J_{trans}$=16.2 Hz, 2×PhCH=CH—), 7.67 (d, $^4J$=1.8 Hz, 1H, 2'-H), 7.74 (dd, J=8.4 Hz, $^4J$=1.8 Hz, 1H, 6'-H); FAB-MS m/z MH$^+$ ion=1321; Anal. Calcd for $C_{83}H_{68}O_{16}$: C, 75.44; H, 5.19. Found: C, 75.78; H, 5.12.

g) 5,7-Dibenzyloxy-2-(2,2-diphenylbenzo[d][1,3]dioxol-5-yl)-3-β-D-[2",6"-di-O-(4-ethoxycinnamoyl)-3",4"-O-isopropylidene]galactosyl-4H-chromen-4-one (10 g)

Yield 68%; IR (KBr) υ 1602 cm$^{-1}$ (C=C), 1633 and 1714 cm$^{-1}$ (C=O); $^1$H NMR (CDCl$_3$, 600 MHz) δ 1.32 and 1.55 (each s, each 3H, 2×CH$_3$), 1.36 and 1.41 (each t, each 3H, J=7.2 Hz, 2×CH$_3$CH$_2$), 3.95 and 4.04 (each q, each 2H, J=7.2 Hz, 2×CH$_3$CH$_2$), 4.08 (ddd, $J_{4'',5''}$=2.4 Hz, $J_{5'',6''Ha}$=5.4 Hz, $J_{5'',6''Hb}$=4.8 Hz, 1H, 5"-H), 4.22 (dd, $J_{3'',4''}$=5.4 Hz, $J_{4'',5''}$=2.4 Hz, 4"-H), 4.30-4.34 (m, 2H, 6"-H), 4.37 (dd, $J_{2'',3''}$=7.2 Hz, $J_{3'',4''}$=5.4 Hz, 1H, 3"-H), 4.92/5.00 (AB system, each d, $J_{AB}$=11.4 Hz, 2H, CH$_2$Ph), 5.20 (s, 2H, CH$_2$Ph), 5.35 (dd, $J_{1'',2''}$=7.8 Hz, $J_{2'',3''}$=7.2 Hz, 1H, 2"-H), 5.90 (d, $J_{1'',2''}$=7.8 Hz, 1H, 1"-H), 6.10 and 6.37 (each d, each 1H, each $J_{trans}$=16.2 Hz, 2×PhCH=CH—), 6.32 (d, $^4J$=2.4 Hz, 1H, 8-H), 6.44 (d, $^4J$=2.4 Hz, 1H, 6-H), 6.78 and 6.83 (each d, each 2H, each J=9.0 Hz, 2×3""-H, 2×5""-H), 6.96 (d, J=8.4 Hz, 1H, 5'-H), 7.32-7.43 (m, 18H, PhH), 7.60-7.63 (m, 6H, PhH, 2×2""-H, 2×6""-H), 7.64 and 7.71 (each d, each 1H, each $J_{trans}$=16.2 Hz, 2×PhCH=CH—), 7.67 (d, $^4J$=1.8 Hz, 1H, 2'H), 7.74 (dd, J=8.4 Hz, $^4J$=1.8 Hz, 1H, 6'-H); FAB-MS m/z MH$^+$ ion=1197; Anal. Calcd for $C_{73}H_{64}O_{16}$: C, 72.23; H, 5.39. Found: C, 72.19; H, 5.35.

h) 5,7-Dibenzyloxy-2-(2,2-diphenylbenzo[d][1,3]dioxol-5-yl)-3-β-D-[2",6"-di-O-(4-methylcinnamoyl)-3",4"-O-isopropylidene]galactosyl-4H-chromen-4-one (10h)

Yield 76%; IR (KBr) υ 1606 cm$^{-1}$ (C=C), 1626 and 1716 cm$^{-1}$ (C=O); $^1$H NMR (CDCl$_3$, 600 MHz) δ 1.34 and 1.56 (each s, each 3H, 2×CH$_3$), 2.31 and 2.35 (each s, each 3H, 2×CH$_3$Ph), 4.08 (ddd, $J_{4'',5''}$=2.4 Hz, $J_{5'',6''Ha}$=4.8 Hz, $J_{5'',6''Hb}$=5.4 Hz, 1H, 5"-H), 4.22 (dd, $J_{3'',4''}$=5.4 Hz, $J_{4'',5''}$=2.4 Hz, 1H, 4"-H), 4.29-4.36 (m, 2H, 6"-H), 4.37 (dd, $J_{2'',3''}$=7.2 Hz, $J_{3'',4''}$=5.4 Hz, 1H, 3"-H), 4.94/4.98 (AB system, each d, $J_{AB}$=11.4 Hz, 2H, CH$_2$Ph), 5.19/5.21 (AB system, each d, $J_{AB}$=11.4 Hz, 2H, CH$_2$Ph), 5.35 (dd, $J_{1'',2''}$=7.8 Hz, $J_{2'',3''}$=7.2 Hz, 1H, 2"-H), 5.89 (d, $J_{1'',2''}$=7.8 Hz, 1H, 1"-H), 6.21 and 6.46 (each d, each 1H, each $J_{trans}$=16.2 Hz, 2×PhCH=CH—), 6.33 (d, $^4J$=2.4 Hz, 1H, 8-H), 6.47 (d, $^4J$=2.4 Hz, 1H, 6-H), 6.96 (d, J=8.4 Hz, 1H, 5'-H), 7.11 and 7.14 (each d, each 2H, each J=7.8 Hz, 2×2""-H, 2×6""-H), 7.26-7.43 (m, 18H, PhH), 7.60-7.63 (m, 6H, PhH, 2×3""-H, 2×5""-H), 7.66 and 7.73 (each d, each 1H, each $J_{trans}$=16.2 Hz, 2×PhCH=CH—), 7.68 (d, $^4J$=1.8 Hz, 1H, 2'-H), 7.74 (dd, J=8.4 Hz, $^4J$=1.8 Hz, 1H, 6'-H); FAB-MS m/z MH$^+$ ion=1137 Anal. Calcd for $C_{71}H_{60}O_{14}$: C, 74.99; H, 5.32. Found: C, 74.77; H, 5.38.

i) 5,7-Dibenzyloxy-2-(2,2-diphenylbenzo[d][1,3]dioxol-5-yl-3-β-D-[2",6"-di-O-(4-fluorocinnamoyl)-3",4"-O-isopropylidene]galactosyl-4H-chromen-4-one (10i)

Yield 72%; IR (KBr) υ 1604 cm$^{-1}$ (C=C), 1630 and 1728 cm$^{-1}$ (C=O); $^1$H NMR (CDCl$_3$, 600 MHz) δ 1.35 and 1.58 (each s, each 3H, 2×CH$_3$), 4.09 (ddd, $J_{4'',5''}$=6.0 Hz, $J_{5'',6''Ha}$=2.4 Hz, $J_{5'',6''Hb}$=1.8 Hz, 1H, 5"-H), 3.58 (dd, $J_{3'',4''}$=5.4 Hz, $J_{4'',5''}$=2.4 Hz, 1H, 4"-H), 4.35 (br d, $J_{gem}$=11.4 Hz, 2H, 6"-H), 4.37 (dd, $J_{2'',3''}$=7.2 Hz, $J_{3'',4''}$=5.4 Hz, 1H, 3"-H), 4.95/4.98 (AB system, each d, $J_{AB}$=12.0 Hz, 2H, CH$_2$Ph), 5.20 (s, 2H, CH$_2$Ph), 5.35 (dd, 2H, $J_{1'',2''}$=7.8 Hz, $J_{2'',3''}$=7.2 Hz, 2"-H), 5.88 (d, $J_{1'',2''}$=7.2 Hz, 1H, 1"-H), 6.16 and 6.43 (each d, each 1H, each $J_{trans}$=16.2 Hz, 2×PhCH=CH—), 6.34 (d, $^4J$=2.4 Hz, 1H, 8-H), 6.45 (d, $^4J$=2.4 Hz, 1H, 6-H), 6.92 (d, J=8.4 Hz, 1H, 5'-H), 6.98 and 7.01 (each t, each 2H, J=8.4 Hz, 2×3""-H, 2×5""-H), 7.32-7.47 (m, 20H, PhH), 7.59-7.62 (m, 4H, 2×2""-H, 2×6""-H), 7.60-7.63 (m, 6H, PhH, 2×3""-H, 2×5""-H), 7.65 and 7.72 (each d, each 1H, each $J_{trans}$=16.2 Hz, 2×PhCH=CH—), 7.66 (d, $^4J$=1.8 Hz, 1H, 2'-H), 7.73 (dd, J=8.4 Hz, $^4J$=1.8 Hz, 1H, 6'-H); FAB-MS m/z MH$^+$ ion=1145; Anal. Calcd for $C_{69}H_{54}O_{14}F_2$: C, 72.37; H, 4.75. Found: C, 72.05; H, 4.59.

j) 5,7-Dibenzyloxy-2-(2,2-diphenylbenzo[d][1,3]dioxol-5-yl)-3-β-D-[2",6"-di-O-(4-fluorobutanoyl)-3",4"-O-isopropylidene]galactosyl-4H-chromen-4-one (10j)

Yield 74%; IR (KBr) υ 1604 cm$^{-1}$ (C=C), 1631 and 1731 cm$^{-1}$ (C=O); $^1$H NMR (CDCl$_3$, 600 MHz) δ 1.32 and 1.55 (each s, each 3H, 2×CH$_3$), 1.61 and 2.10 (each quintet, 4H, 2×PhCH$_2$CH$_2$CH$_2$), 2.38 and 2.40 (each t, each 2H, J=7.2 Hz, 2×CH$_2$CH$_2$CO), 2.48 and 2.51 (each t, each 2H, J=7.2 Hz, 2×PhCH$_2$CH$_2$), 3.95 (ddd, $J_{4'',5''}$=2.4 Hz, $J_{5'',6''Ha}$=5.4 Hz, $J_{5'',6''Hb}$=4.8 Hz, 1H, 5"-H), 4.13 (dd, $J_{3'',4''}$=5.4 Hz, $J_{4'',5''}$=2.4 Hz, 1H, 4"-H), 4.15-4.18 (m, 2H, 6"-H), 4.26 (dd, $J_{2'',3''}$=7.2 Hz, $J_{3'',4''}$=5.4 Hz, 1H, 3"-H), 5.01/5.10 (AB system, each d, $J_{AB}$=11.4 Hz, 2H, PhCH$_2$), 5.21-5.25 (m, 3H, 2"-H, PhCH$_2$), 5.75 (d, $J_{1'',2''}$=7.8 Hz, 1H, 1"-H), 6.41 (d, $^4J$=2.4 Hz, 1H, 8-H), 6.49 (d, $^4J$=2.4 Hz, 1H, 6-H), 6.85 and 6.94 (each t, each 2H, J=9.0 Hz, 2×3""-H, 2×5""-H), 6.95 (d, J=8.4 Hz, 1H, 5'-H), 7.06 and 7.08 (each d, J=8.4, each 2H, 2×2""-H, 2×6""-H), 7.28-7.41 (m, 14H, PhH), 7.59-7.62 (m, 6H, PhH), 7.65 (d, $^4J$=2.4 Hz, 1H, 2'-H), 7.71 (dd, J=8.4 Hz, $^4J$=1.8 Hz, 1H, 6'-H); FAB-MS m/z MH⁺ ion=1177; Anal. Calcd for $C_{71}H_{62}O_{14}F_2$: C, 72.44; H, 5.31. Found: C, 72.19; H, 5.35.

k) 5,7-Dibenzyloxy-2-(2,2-diphenylbenzo[d][1,3]
dioxol-5-yl)-3-β-D-[2",6"-di-O-(4-fluoropentanoyl)-
3",4"-O-isopropylidene]galactosyl-4H-chromen-4-
one (10k)

Yield 70%; IR (KBr) υ 1604 cm⁻¹ (C=C), 1631 and 1735 cm⁻¹ (C=O); ¹H NMR (CDCl₃, 600 MHz) δ 1.31 and 1.55 (each s, each 3H, 2×CH₃), 1.55-1.63 (m, 4H, 2×PhCH₂CH₂CH₂), 1.70 and 2.14 (each quintet, each 2H, J=7.2 Hz, 2×CH₂CH₂CH₂CH₂), 2.41 and 2.45 (each t, each 2H, J=7.2 Hz, 2×CH₂CH₂CO), 2.49 and 2.52 (each t, each 2H, J=7.2 Hz, 2×PHCH₂CH₂), 3.92 (ddd, $J_{4",5"}$=2.4 Hz, $J_{5",6"Ha}$=5.4 Hz, $J_{5",6"Hb}$=4.8 Hz, 1H, 5"-H), 4.11 (dd, $J_{3",4"}$=5.4 Hz, $J_{4",5"}$=2.4 Hz, 1H, 4"-H), 4.13-4.19 (m, 2H, 6"-H), 4.26 (dd, $J_{2",3"}$=7.2 Hz, $J_{3",4"}$=5.4 Hz, 1H, 3"-H), 4.99/5.04 (AB system, each d, $J_{AB}$=11.4 Hz, 2H, PhCH₂), 5.22 (dd, $J_{1",2"}$=7.8 Hz, $J_{2",3"}$=7.2 Hz, 1H, 2"-H), 5.69 (d, $J_{1",2"}$=7.8 Hz, 1H, 1"-H), 6.41 (d, ⁴J=2.4 Hz, 1H, 8-H), 6.52 (d, ⁴J=2.4 Hz, 1H, 6-H), 6.79 and 6.89 (each t, each 2H, J=9.0 Hz, 2×3""-H, 2×5""-H), 6.95 (d, J=8.4 Hz, 1H, 5'-H), 6.98 and 7.00 (each d, J=8.4, each 2H, 2×2""-H, 2×6""-H), 7.35-7.41 (m, 14H, PhH), 7.59-7.61 (m, 6H, PhH), 7.65 (d, ⁴J=2.4 Hz, 1H, 2'-H), 7.71 (dd, J=8.4 Hz, ⁴J=1.8 Hz, 1H, 6'-H); FAB-MS m/z MH⁺ ion=1206; Anal. Calcd for $C_{73}H_{66}O_{14}F_2$: C, 72.74; H, 5.52. Found: C, 72.58; H, 5.28.

l) 5,7-Dibenzyloxy-2-(2,2-diphenylbenzo[d][1,3]
dioxol-5-yl)-3-β-D-[6"-O-(4-methylcinnamoyl)-3",
4"-O-isopropylidene]galactosyl-4H-chromen-4-one
(10l)

Yield 69%; IR (KBr) υ 1614 cm⁻¹ (C=C), 1633 and 1720 cm⁻¹ (C=O); ¹H NMR (CDCl₃, 600 MHz) δ 1.37 and 1.60 (each s, each 3H, 2×CH₃), 2.35 (s, 3H, CH₃Ph), 3.87 (dd, $J_{2",3"}$=7.2 Hz, $J_{3",4"}$=5.4 Hz, 1H, 3"-H), 3.93 (ddd, $J_{4",5"}$=4.8 Hz, $J_{5",6"a}$=2.4 Hz, $J_{5",6"Hb}$=4.2 Hz, 1H, 5"-H), 4.13 (dd, $J_{3",4"}$=5.4 Hz, $J_{4",5"}$=4.8 Hz, 1H, 4"-H), 4.22 (dd, $J_{1",2"}$=7.8 Hz, $J_{2",3"}$=7.2 Hz, 1H, 2"-H), 4.23 (dd, $J_{5",6"Hb}$=3.6 Hz, $J_{gem}$=11.4 Hz, 1H, 6"-Hb), 4.42 (dd, $J_{5",6"Ha}$=4.2 Hz, $J_{gem}$=11.4 Hz, 1H, 6"-Ha), 4.85 (d, $J_{1",2"}$=7.8 Hz, 1H, 1"-H), 5.07 and 5.24 (each s, each 2H, 2×CH₂Ph), 6.17 (d, 1H, $J_{trans}$=15.6 Hz, PhCH=CH—), 6.47 (d, ⁴J=2.4 Hz, 1H, 8-H), 6.57 (d, ⁴J=2.4 Hz, 1H, 6-H), 6.96 (d, J=8.4 Hz, 1H, 5'-H), 7.12 and 7.25 (each d, each 2H, each J=8.4 Hz, 2""-H & 6""-H, 3""-H & 5""-H), 7.33-7.42 (m, 18H, PhH), 7.47 (d, 1H, $J_{trans}$=16.2 Hz, PhCH=CH—), 7.56-7.58 (m, 4H, PhH), 7.80 (dd, J=8.4 Hz, ⁴J=1.8 Hz, 1H, 6'-H), 7.81 (d, ⁴J=1.8 Hz, 1H, 2'-H); FAB-MS m/z MH⁺ ion=993 Anal. Calcd for $C_{61}H_{52}O_{13}$: C, 73.78; H, 5.28. Found: C, 73.77; H, 5.26.

m) 5,7-Dibenzyloxy-2-(2,2-diphenylbenzo[d][1,3]
dioxol-5-yl)-3-β-D-[6"-O-(4-fluorocinnamoyl)-3",
4"-O-isopropylidene]galactosyl-4H-chromen-4-one
(10m)

Yield 69%; IR (KBr) υ 1614 cm⁻¹ (C=C), 1634 and 1719 cm⁻¹ (C=O); ¹H NMR (CDCl₃, 600 MHz) δ 1.37 and 1.60 (each s, each 3H, 2×CH₃), 3.87 (dd, $J_{2",3"}$=7.2 Hz, $J_{3",4"}$=5.4 Hz, 1H, 3"-H), 3.93-3.95 (m, 1H, 5"-H), 4.13 (dd, $J_{3",4"}$=5.4 Hz, $J_{4",5"}$=2.4 Hz, 1H, 4"-H), 4.24 (dd, $J_{1",2"}$=8.4 Hz, $J_{2",3"}$=7.2 Hz, 1H, 2"-H), 4.28 (dd, $J_{5",6"Hb}$=4.8 Hz, $J_{gem}$=11.4 Hz, 1H, 6"-Hb), 4.45 (dd, $J_{5",6"Ha}$=3.6 Hz, $J_{gem}$=11.4 Hz, 1H, 6"-Ha), 4.86 (d, $J_{1",2"}$=8.4 Hz, 1H, 1"-H), 5.06/5.09 (AB system, $J_{AB}$=15.4 Hz, 2H, CH₂Ph), 5.24 (s, 2H, CH₂Ph), 6.10 (d, 1H, $J_{trans}$=16.2 Hz, PhCH=CH—), 6.47 (d, ⁴J=2.4 Hz, 1H, 8-H), 6.54 (d, ⁴J=2.4 Hz, 1H, 6-H), 6.94 (d, J=8.4 Hz, 1H, 5'-H), 6.95 and 6.97 (each t, each 2H, each J=8.4 Hz, 2""-H & 6""-H, 3""-H & 5""-H), 7.34-7.41 (m, 18H, PhH), 7.42 (d, 1H, $J_{trans}$=16.2 Hz, PhCH=CH—), 7.56-7.57 (m, 4H, PhH), 7.81 (d, ⁴J=1.8 Hz, 1H, 2'-H), 7.82 (br s, 1H, 6'-H); FAB-MS m/z MH⁺ ion=997 Anal. Calcd for $C_{60}H_{49}O_{13}F$: C, 72.28; H, 4.95. Found: C, 72.63; H, 5.13.

Example 2-6

Synthesis and Identification of Intermediates 11a-m for Galactose Derivative (FIG. 3)
General Procedure and Characterizations for Compounds 11a-m:

Each of mixed solutions of 10a-m (1.0 mmol) and MeOH (25 mL) was stirred with heating at 50 to 60° C. for 5 to 7 hours under hydrochloric acid gas atmosphere. After completion of the reaction, the reaction mixture was allowed to stand to cool, neutralized with triethylamine, and evaporated under reduced pressure. Ethanol was added to the residue, and insoluble substances were removed by filtration. The filtrate was evaporated under reduced pressure, and the residue was then purified by flash column chromatography using a mixed solvent of EtOAc-n-hexane (1:1), to thereby obtain colorless powders 11a-m.

a) 5,7-Dibenzyloxy-2-(2,2-diphenylbenzo[d][1,3]
dioxol-5-yl)-3-β-D-[2",6"-di-O-(4-ethoxybenzoyl)]
glucosyl-4H-chromen-4-one (11a)

Yield 73%; IR (KBr) υ 1608 cm⁻¹ (C=C), 1635 and 1718 cm⁻¹ (C=O), 3470 cm⁻¹ (OH); ¹H NMR (CDCl₃, 600 MHz): δ 1.38 and 1.40 (each t, each 3H, each J=7.2 Hz, 2×CH₃CH₂), 3.86-3.88 (m, 1H, 5"-H), 3.95-3.99 (m, 3H, 4"-H, CH₃CH₂), 3.98-4.01 (q, 2H, J=7.2 Hz, CH₃CH₂), 4.02 (dd, $J_{2",3"}$=7.2 Hz, $J_{3",4"}$=5.4 Hz, 1H, 3"-H), 4.34 (dd, $J_{5",6"Hb}$=6.6 Hz, $J_{gem}$=11.4 Hz, 1H, 6"-Hb), 4.48 (dd, $J_{5",6"Ha}$=6.0 Hz, $J_{gem}$=11.4 Hz, 1H, 6"-Ha), 5.07 (s, 2H, CH₂Ph), 5.24 (dd, $J_{1",2"}$=7.8 Hz, $J_{2",3"}$=7.2 Hz, 1H, 2"-H), 5.26/5.29 (AB system, each d, $J_{AB}$=13.2 Hz, 2H, PhCH₂), 5.87 (d, $J_{1",2"}$=7.8 Hz, 1H, 2"-H), 6.44 (d, ⁴J=2.4 Hz, 8-H), 6.53 (d, ⁴J=2.4 Hz, 6-H), 6.74 and 6.83 (each d, each 2H, each J=9.0 Hz, 2×3'''-H, 2×5'''-H), 6.92 (d, J=8.9 Hz, 1H, 5'-H), 7.35-7.42 (m, 14H, PhH), 7.59-7.61 (m, 7H, PhH), 7.69 (dd, J=8.4 Hz, ⁴J=1.8 Hz, 1H, 6'-H), 7.84 and 8.11 (each d, each 2H, each J=9.0 Hz, 2×2'''-H, 2×6'''-H); FAB-MS m/z MH⁺ ion=1105; Anal. Calcd for $C_{66}H_{56}O_{16}$: C, 71.73; H, 5.11. Found: C, 71.76; H, 4.97.

b) 5,7-Dibenzyloxy-2-(2,2-diphenylbenzo[d][1,3]
dioxol-5-yl)-3-β-D-[2",3"-di-O-(4-propylbenzoyl)]
galactoosyl-4H-chromen-4-one (11b)

Yield 78%; IR (KBr) υ 1604 cm⁻¹ (C=C), 1634 and 1712 cm⁻¹ (C=O), 3464 cm⁻¹ (OH); ¹H NMR (CDCl₃, 600 MHz) δ 0.90 and 0.92 (each t, each 3H, J=7.2 Hz, 2×CH₃CH₂), 1.58-1.65 (m, 4H, 2×CH₃CH₂CH₂), 2.57-2.59 (each t, each 2H, J=7.2 Hz, 2×CH₃CH₂CH₂), 3.87-3.89 (m, 2H, 4"-H, 5"-H,), 3.99 (dd, $J_{2",3"}$=7.2 Hz, $J_{3",4"}$=5.4 Hz, 1H, 3"-H), 4.34 (dd, $J_{5",6"Hb}$=6.6 Hz, $J_{gem}$=11.4 Hz, 1H, 6"-Hb), 4.51 (dd, $J_{5",6"Ha}$=6.0 Hz, $J_{gem}$=11.4 Hz, 1H, 6"-Ha), 5.07 (s, 2H, CH₂Ph), 5.27 (s, 2H, CH₂Ph), 5.30 (dd, $J_{1",2"}$=7.8 Hz, $J_{2",3"}$=7.2 Hz, 1H, 2"-H), 5.87 (d, $J_{1",2"}$=7.8 Hz, 1H, 1"-H), 6.45 (d, ⁴J=2.4 Hz, 1H, 8-H), 6.54 (d, ⁴J=2.4 Hz, 1H, 6-H), 6.91 (d, J=8.4 Hz, 1H, 5'-H), 7.11 and 7.17 (each d, each 2H, each J=9.0 Hz, 2×3'''-H, 2×5'''-H), 7.35-7.42 (m, 14H, PhH), 7.59-

7.62 (m, 8H, PhH), 7.69 (dd, J=8.4 Hz, $^4$J=1.8 Hz, 1H, 6'-H), 7.83 and 8.09 (each d, each 2H, each J=9.0 Hz, 2×2'''-H, 2×6'''-H); FAB-MS m/z MH$^+$ ion=MH$^+$ 1101; Anal. Calcd for $C_{68}H_{60}O_{14}$: C, 74.17; H, 5.49. Found: C, 73.78; H, 5.30.

c) 5,7-Dibenzyloxy-2-(2,2-diphenylbenzo[d][1,3]dioxol-5-yl)-3-β-D-[2'',6''-di-O-(4-fluorobenzoyl)]galactosyl-4H-chromen-4-one (11c)

Yield 0.83 79%; IR (KBr) υ 1606 cm$^{-1}$ (C=C); 1633 and 1716 cm$^{-1}$ (C=O); 3427 cm$^{-1}$ (OH); $^1$H NMR (CDCl$_3$, 600 MHz) δ 3.45 (br s, 1H, 4''-OH, D$_2$O), 3.85-3.90 (m, 2H, 4''-H, 5''-H), 3.98 (d, $J_{3'',4''}$=4.2 Hz, 1H, 3''-H), 4.40 (dd, $J_{5'',6''Hb}$=7.2 Hz, $J_{gem}$=11.4 Hz, 1H, 6''-Hb), 4.46 (dd, $J_{5'',6''Ha}$=6.0 Hz, $J_{gem}$=11.4 Hz, 1H, 6''-Ha), 5.08 and 5.25 (each s, each 2H, 2×CH$_2$Ph), 5.34 (dd, $J_{1'',2''}$=7.8 Hz, $J_{2'',3''}$=7.2 Hz, 1H, 2''-H), 5.79 (d, $J_{1'',2''}$=7.8 Hz, 1H, 1''-H), 6.47 (d, $^4$J=2.4 Hz, 8-H), 6.52 (d, $^4$J=2.4 Hz, 6-H), 6.91 (d, J=8.4 Hz, 1H, 5'-H), 6.93 and 7.01 (each t, each 2H, J=9.0 Hz, 2×3''''-H, 2×5''''-H), 7.35-7.93 (m, 14H, PhH), 7.59-7.60 (m, 7H, PhH), 7.67 (dd, J=8.4 Hz, $^4$J=1.8 Hz, 1H, 6'-H), 7.87 and 8.20 (each dd, each 2H, J=9.0 Hz, J=8.4 Hz, 2×2''''-H, 2×6''''-H); FAB-MS m/z MH$^+$ ion=1053; Anal. Calcd for $C_{62}H_{46}O_{14}F_2$: C, 70.72; H, 4.90. Found: C, 70.39; H, 4.22.

d) 5,7-Dibenzyloxy-2-(2,2-diphenylbenzo[d][1,3]dioxol-5-yl)-3-β-D-[2'',6''-di-O-(4-methylphenylacetyl)]galactosyl-4H-chromen-4-one (11d)

Yield 76%; IR (KBr) υ 1604 cm$^{-1}$ (C=C), 1633 and 1743 cm$^{-1}$ (C=O), 3443 cm$^{-1}$ (OH); $^1$H NMR (CDCl$_3$, 600 MHz) δ 2.25 and 2.26 (each s, each 3H, 2×CH$_3$Ph), 3.43/3.45 (AB system, each d, $J_{AB}$=15.0 Hz, 2H, PhCH$_2$CO), 3.59-3.61 (m, 1H, 5''-H), 3.66 (dd, $J_{3'',4''}$=3.6 Hz, $J_{4'',5''}$=2.4 Hz, 1H, 4''-H), 3.72 (s, 2H, PhCH$_2$CO), 3.52 (d, $J_{3'',4''}$=3.6 Hz, 1H, 3''-H), 4.01 (dd, $J_{5'',6''Hb}$=6.6 Hz, $J_{gem}$=11.4 Hz, 1H, 6''-Hb), 4.20 (dd, $J_{5'',6''Ha}$=6.0 Hz, $J_{gem}$=11.4 Hz, 1H, 6''-Ha), 5.08 (s, 2H, CH$_2$Ph), 5.13 (dd, $J_{1'',2''}$=7.8 Hz, $J_{2'',3''}$=7.2 Hz, 1H, 2''-H), 5.26 (s, 2H, CH$_2$Ph), 5.57 (d, $J_{1'',2''}$=7.8 Hz, 1H, 1''-H), 6.45 (d, $^4$J=2.4 Hz, 1H, 8-H), 6.57 (d, $^4$J=2.4 Hz, 1H, 6-H), 6.94 (d, J=8.4 Hz, 1H, 5'-H), 7.01-7.03 (m, 4H, 2×3''''-H, 2×5''''-H), 7.05 and 7.18 (each d, each 2H, J=9.0 Hz, 2×2''''-H, 2×6''''-H), 7.39-7.41 (m, 14H, PhH), 7.56-7.59 (m, 7H, PhH), 7.66 (dd, J=8.4 Hz, $^4$J=1.8 Hz, 1H, 6'-H); FAB-MS m/z MH$^+$ ion=1073; Anal. Calcd for $C_{66}H_{56}O_{14}$: C, 73.46; H, 5.29. Found: C, 73.79; H, 5.13.

e) 5,7-Dibenzyloxy-2-(2,2-diphenylbenzo[d][1,3]dioxol-5-yl)-3-β-D-[2'',6''-di-O-(4-fluorophenylacetyl)]galactosyl-4H-chromen-9-one (11e)

Yield 75%); IR (KBr) υ 1604 cm$^{-1}$ (C=C), 1633 and 1741 cm$^{-1}$ (C=O), 3466 cm$^{-1}$ (OH); $^1$H NMR (CDCl$_3$, 600 MHz) δ 3.41/3.44 (AB system, each d, $J_{AB}$=16.2 Hz, 2H, PhCH$_2$CO), 3.59-3.62 (m, 1H, 5''-H), 3.68 (dd, $J_{3'',4''}$=5.4 Hz, $J_{4'',5''}$=2.4 Hz, 1H, 4''-H), 3.71/3.76 (AB system, each d, $J_{AB}$=16.2 Hz, 2H, PhCH$_2$CO), 3.77 (br d, $J_{3'',4''}$=5.4 Hz, 1H, 4''-H), 4.04 (dd, $J_{5'',6''Hb}$=6.6 Hz, $J_{gem}$=11.4 Hz, 1H, 6''-Hb), 4.19 (dd, $J_{5'',6''Ha}$=6.0 Hz, $J_{gem}$=11.4 Hz, 1H, 6''-Ha), 5.08 (s, 2H, CH$_2$Ph), 5.17 (dd, $J_{1'',2''}$=7.8 Hz, $J_{2'',3''}$=7.2 Hz, 1H, 2''-H), 5.25 (s, 2H, CH$_2$Ph), 5.54 (d, $J_{1'',2''}$=7.8 Hz, 1H, 1''-H), 6.46 (d, $^4$J=2.4 Hz, 1H, 8-H), 6.58 (d, $^4$J=2.4 Hz, 1H, 6-H), 6.90 (d, J=8.4 Hz, 1H, 5'-H), 6.92 and 7.05 (each t, each 2H, J=9.0 Hz, 2×3''''-H, 2×5''''-H), 7.25 and 7.27 (each dd, each 2H, J=8.4 Hz, J=9.0 Hz, 2×2''''-H, 2×6''''-H), 7.33-7.92 (m, 14H, PhH), 7.55-7.58 (m, 7H, PhH), 7.65 (dd, J=8.4 Hz, $^4$J=1.8 Hz, 1H, 6'-H); FAB-MS m/z MH$^+$ ion=1081; Anal. Calcd for $C_{64}H_{50}O_{14}F_2$: C, 71.10; H, 4.66. Found: C, 70.89; H, 4.67.

f) 5,7-Dibenzyloxy-2-(2,2-diphenylbenzo[d][1,3]dioxol-5-yl)-3-β-D-[2'',6''-di-O-(4-benzyloxycinnamoyl)]galactosyl-4H-chromen-4-one (11f)

Yield 69%; IR (KBr) υ 1605 cm$^{-1}$ (C=C), 1635 and 1790 cm$^{-1}$ (C=O), 3467 cm$^{-1}$ (OH); $^1$H NMR (CDCl$_3$, 600 MHz) δ 3.80-3.89 (m, 2H, 4''-H, 5''-H), 3.95 (d, $J_{3'',4''}$=3.6 Hz, 3''-H), 4.26 (dd, $J_{5'',6''Hb}$=6.6 Hz, $J_{gem}$=11.4 Hz, 1H, 6''-Hb), 4.39 (dd, $J_{5'',6''Ha}$=6.0 Hz, $J_{gem}$=11.4 Hz, 1H, 6''-Ha), 4.99, 5.03, 5.04, 5.24 (each s, each 2H, 4×CH$_2$Ph), 5.21 (dd, $J_{1'',2''}$=7.8 Hz, $J_{2'',3''}$=7.2 Hz, 1H, 2''-H), 5.76 (d, $J_{1'',2''}$=7.8 Hz, 1H, 1''-H), 6.19 and 6.34 (each d, each 1H, each $J_{trans}$=16.2 Hz, 2×PhCH=CH—), 6.37 (d, $^4$J=2.4 Hz, 8-H), 6.48 (d, $^4$J=2.4 Hz, 6-H), 6.88 and 6.90 (each d, each 2H, each J=9.0 Hz, 2×3''''-H, 2×5''''-H), 6.95 (d, J=8.0 Hz, 1H, 5'-H), 7.33-7.41 (m, 28H, PhH), 7.52-7.55 and 7.58-7.62 (each m, 8H, PhH), 7.60 and 7.76 (each d, each 1H, each $J_{trans}$=16.2 Hz, 2×PhCH=CH—), 7.72 (dd, J=8.4 Hz, $^4$J=1.8 Hz, 1H, 6'-H); FAB-MS m/z MH$^+$ ion=1281; Anal. Calcd for $C_{80}H_{64}O_{16}$: C, 74.99; H, 5.03. Found: C, 74.74; H, 4.93.

g) 5,7-Dibenzyloxy-2-(2,2-diphenylbenzo[d][1,3]dioxol-5-yl)-3-β-D-[2'',6''-di-O-(4-ethoxycinnamoyl)]galactosyl-4H-chromen-4-one (11g)

Yield 74%; IR (KBr) υ 1606 cm$^{-1}$ (C=C), 1634 and 1742 cm$^{-1}$ (C=O), 3464 cm$^{-1}$ (OH); $^1$H NMR (CDCl$_3$, 600 MHz) δ 1.38 and 1.40 (each t, each 3H, J=7.2 Hz, 2×CH$_3$CH$_2$), 3.78-3.81 (m, 2H, 4''-H, 5''-H), 3.93 (d, $J_{3'',4''}$=3.6 Hz, 1H, 3''-Ha), 3.98 and 4.01 (each q, each 2H, J=7.8 Hz, 2×CH$_3$CH$_2$), 4.29 (dd, $J_{5'',6''Hb}$=6.0 Hz, $J_{gem}$=11.4 Hz, 1H, 6''-Hb), 4.37 (dd, $J_{5'',6''Ha}$=6.6 Hz, $J_{gem}$=11.4 Hz, 1H, 6''-Ha), 5.98 and 5.25 (each s, each 2H, 2×CH$_2$Ph), 5.23 (dd, $J_{1'',2''}$=7.8 Hz, $J_{2'',3''}$=7.2 Hz, 1H, 2''-H), 5.67 (d, $J_{1'',2''}$=7.8 Hz, 1H, 1''-H), 6.17 and 6.36 (each d, each 1H, each $J_{trans}$=16.2 Hz, 2×PhCH=CH—), 6.38 (d, $^4$J=2.4 Hz, 8-H), 6.46 (d, $^4$J=2.4 Hz, 6-H), 6.79 and 6.82 (each d, each 2H, each J=8.4 Hz, 2×3''''-H, 2×5''''-H), 6.96 (d, J=8.4 Hz, 1H, 5'-H), 7.32-7.42 (m, 20H, PhH), 7.53 and 7.76 (each d, each 1H, each $J_{trans}$=16.2 Hz, 2×PhCH=CH—), 7.56-7.61 (m, 5H, PhH, 2×2''''-H, 2×6''''-H, 2'-H), 7.72 (dd, J=8.4 Hz, $^4$J=1.8 Hz, 1H, 6'-H); FAB-MS m/z MH$^+$ ion=1157; Anal. Calcd for $C_{70}H_{60}O_{16}$: C, 72.65; H, 5.23. Found: C, 72.66; H, 5.22.

h) 5,7-Dibenzyloxy-2-(2,2-diphenylbenzo[d][1,3]dioxol-5-yl)-3-β-D-[2'',6''-di-O-(4-methylcinnamoyl)]galactosyl-4H-chromen-4-one (11h)

Yield 78%; IR (KBr) υ 1604 cm$^{-1}$ (C=C), 1633 and 1739 cm$^{-1}$ (C=O), 3460 cm$^{-1}$ (OH); $^1$H NMR (CDCl$_3$, 600 MHz) δ 2.34 and 2.38 (each s, 6H, 2×PhCH$_3$), 3.80-3.82 (m, 2H, 4''-H, 5''-H), 3.95 (d, $J_{3'',4''}$=3.6 Hz, 1H, 3''-H), 4.28 (dd, $J_{5'',6''Hb}$=6.0 Hz, $J_{gem}$=11.4 Hz, 1H, 6''-Hb), 4.34 (dd, $J_{5'',6''Ha}$=6.6 Hz, $J_{gem}$=11.4 Hz, 1H, 6''-Ha), 5.00 and 5.25 (each s, each 2H, 2×CH$_2$Ph), 5.20 (dd, $J_{1'',2''}$=7.2 Hz, $J_{2'',3''}$=7.2 Hz, 1H, 2''-H), 5.72 (d, $J_{1'',2''}$=7.8 Hz, 1H, 1''-H), 6.26 and 6.44 (each d, each 1H, each $J_{trans}$=16.2 Hz, 2×PhCH=CH—), 6.41 (d, $^4$J=2.4 Hz, 8-H), 6.49 (d, $^4$J=2.4 Hz, 6-H), 7.14 (d, J=8.4 Hz, 1H, 5'-H), 7.09 and 7.12 (each d, each 2H, each J=8.4 Hz, 2×2''''-H, 2×6''''-H), 7.35-7.40 (m, 20H, Ar—), 7.54-7.62 (m, 6H, PhH, 2×3''''-H, 2×5''''-H), 7.70 and 7.77 (each d, each 1H, each $J_{trans}$=16.2 Hz, 2×PhCH=CH—); FAB-MS m/z MH⁺ ion=1097; Anal. Calcd for $C_{68}H_{56}O_{14}$: C, 74.44; H, 5.14. Found: C, 74.30; H, 5.27.

i) 5,7-Dibenzyloxy-2-(2,2-diphenylbenzo[d][1,3]dioxol-5-yl)-3-β-D-[2",6"-di-O-(4-fluorocinnamoyl)]galactosyl-4H-chromen-4-one (11i)

Yield 76%; IR (KBr) υ 1604 cm⁻¹ (C=C), 1630 and 1762 cm⁻¹ (C=O), 335.8 cm⁻¹ (OH); ¹H NMR (CDCl₃, 600 MHz) δ 3.81 (dd, $J_{5'',6Hb''}$=6.0 Hz, $J5''_{,6Ha''}$=5.4 Hz, 1H, 5"-H), 3.84 (dd, $J_{3'',4''}$=4.2 Hz, $J_{4'',5''}$=2.4 Hz, 1H, 4"-H), 3.96 (d, $J_{3'',4''}$=4.2 Hz, 3"-H), 4.28 (dd, $J_{5'',6''Hb}$=6.0 Hz, $J_{gem}$=11.4 Hz, 1H, 6"-Hb), 4.39 (dd, $J_{5'',6''Ha}$=6.6 Hz, $J_{gem}$=11.4 Hz, 1H, 6"-Ha), 5.00 and 5.26 (each s, each 2H, 2×CH₂Ph), 5.25 (dd, $J_{1'',2''}$=7.8 Hz, $J_{2'',3''}$=7.2 Hz, 1H, 2"-H), 5.74 (d, $J_{1'',2''}$=7.2 Hz, 1H, 1"-H), 6.25 and 6.40 (each d, each 1H, each $J_{trans}$=16.2 Hz, 2×PhCH=CH—), 6.39 (d, ⁴J=2.4 Hz, 8-H), 6.48 (d, ⁴J=2.4 Hz, 6-H), 6.95 (d, J=8.4 Hz, 1H, 5'-H), 6.96 and 7.01 (each t, each 2H, J=9.0 Hz, 2×3""-H, 2×5""-H), 7.35-7.45 (m, 20H, PhH), 7.55 and 7.79 (each d, each 1H, each $J_{trans}$=16.2 Hz, 2×PhCH=CH—), 7.58-7.62 (m, 5H, PhH, 2×2""-H, 2×6""-H), 7.72 (dd, J=8.4 Hz, ⁴J=1.8 Hz, 1H, 6'-H); FAB-MS m/z MH⁺ ion=1105; Anal. Calcd for $C_{66}H_{50}O_{14}F_2$: C, 71.73; H, 4.56. Found: C, 71.55; H, 4.46.

j) 5,7-Dibenzyloxy-2-(2,2-diphenylbenzo[d][1,3]dioxol-5-yl)-3-β-D-[2",6"-di-O-(4-fluorobutanoyl)]galactosyl-4H-chromen-4-one (11j)

Yield 69%; IR (KBr) υ 1607 cm⁻¹ (C=C), 1642 and 1750 cm⁻¹ (C=O); ¹H NMR (CDCl₃, 600 MHz) δ 1.76 and 1.93 (each quintet, 4H, 2×PhCH₂CH₂CH₂), 2.15 and 2.17 (each t, each 2H, J=7.2 Hz, 2×CH₂CH₂CO), 2.44 and 2.58 (each t, each 2H, J=7.2 Hz, 2×PhCH₂CH₂), 3.95 (dd, $J_{4'',5''}$=5.4 Hz, $J_{5'',6''Ha/5'',6''Hb}$=6.0 Hz, 1H, 5"-H), 3.72 (dd, $J_{3'',4''}$=5.4 Hz, $J_{4'',5''}$=3.6 Hz, 1H, 4"-H), 3.86 (d, 1H, $J_{3'',4''}$=5.4 Hz, 3"-H), 4.12 (dd, $J_{5'',6''Hb}$=6.0 Hz, $J_{gem}$=11.4 Hz, 1H, 6"-Hb), 4.20 (dd, $J_{5'',6''Ha}$=6.6 Hz, $J_{gem}$=11.4 Hz, 1H, 6"-Ha), 5.03/5.06 (AB system, each d, $J_{AB}$=11.4 Hz, 2H, PhCH₂), 5.20-5.24 (m, 3H, 2"-H, PhCH₂), 5.62 (d, $J_{1'',2''}$=7.8 Hz, 1H, 1"-H), 6.43 (d, ⁴J=2.4 Hz, 1H, 8-H), 6.51 (d, ⁴J=2.4 Hz, 1H, 6-H), 6.87 and 6.89 (each t, each 2H, J=8.4 Hz, 2×3""-H, 2×5""-H), 6.95 (d, J=8.4 Hz, 1H, 5'-H), 6.99 and 7.06 (each dd, J=8.4 Hz, J=9.0 Hz, each 2H, 2×2""-H, 2×6""-H), 7.35-7.41 (m, 14H, PhH), 7.56-7.62 (m, 7H, PhH), 7.69 (dd, J=8.4 Hz, ⁴J=1.8 Hz, 1H, 6'-H); FAB-MS m/z MH⁺ ion=1137; Anal. Calcd for $C_{68}H_{58}O_{14}F_2$: C, 71.82; H, 5.14. Found: C, 71.63; H, 4.19.

k) 5,7-Dibenzyloxy-2-(2,2-diphenylbenzo[d][1,3]dioxol-5-yl)-3-β-D-[2",6"-di-O-(4-fluoropentanoyl)]galactosyl-4H-chromen-4-one (11k)

Yield 72%; IR (KBr) υ 1608 cm⁻¹ (C=C), 1640 and 1752 cm⁻¹ (C=O); ¹H NMR (CDCl₃, 600 MHz) δ 1.48-1.52 (m, 4H, 2×PhCH₂CH₂CH₂), 1.59 and 1.67 (each quintet, each 2H, J=7.2 Hz, 2×CH₂CH₂CH₂CO), 2.19 and 2.44 (each t, each 2H, J=7.2 Hz, 2×CH₂CH₂CO), 2.47 and 2.51 (each t, each 2H, J=7.2 Hz, 2×PHCH₂CH₂), 3.64 (ddd, $J_{4'',5''}$=5.4 Hz, $J_{5'',6''Ha/5'',6''Hb}$=6.0 Hz, 5"-H), 3.71 (dd, $J_{3'',4''}$=5.4 Hz, $J_{4'',5''}$=3.6 Hz, 1H, 4"-H), 3.83 (d, 1H, $J_{3'',4''}$=5.4 Hz, 3"-H), 4.05 (dd, $J_{5'',6''Hb}$=6.0 Hz, $J_{gem}$=11.4 Hz, 1H, 6"-Hb), 4.20 (dd, $J_{5'',6''Ha}$=6.6 Hz, $J_{gem}$=11.4 Hz, 1H, 6"-Ha), 4.03/5.06 (AB system, each d, $J_{AB}$=11.4 Hz, 2H, PhCH₂), 5.22 (dd, $J_{1'',2''}$=7.8 Hz, $J_{2'',3''}$=7.2 Hz, 1H, 2"-H), 5.25 (s, 2H, PhCH₂), 5.63 (d, $J_{1'',2''}$=7.8 Hz, 1H, 1"-H), 6.42 (d, ⁴J=2.4 Hz, 1H, 8-H), 6.53 (d, ⁴J=2.4 Hz, 1H, 6-H), 6.82 and 6.91 (each t, each 2H, J=9.0 Hz, 2×3""-H, 2×5""-H), 6.95 (d, J=8.4 Hz, 1H, 5'-H), 7.00 and 7.03 (each dd, J=8.4 Hz, J=9.0 Hz, each 2H, 2×2""-H, 2×6""-H), 7.35-7.42 (m, 14H, PhH), 7.54-7.61 (m, 7H, PhH), 7.69 (dd, J=8.4 Hz, ⁴J=1.8 Hz, 1H, 6'-H); FAB-MS m/z MH⁺ ion=1165; Anal. Calcd for $C_{70}H_{62}O_{14}F_2$: C, 72.15; H, 5.36. Found: C, 72.24; H, 5.31.

l) 5,7-Dibenzyloxy-2-(2,2-diphenylbenzo[d][1,3]dioxol-5-yl)-3-β-D-[6"-O-(4-methylcinnamoyl)]galactosyl-4H-chromen-4-one (11l)

Yield 68%; IR (KBr) υ 1604 cm⁻¹ (C=C), 1631 and 1741 cm⁻¹ (C=O); 3461 cm⁻¹ (OH); ¹H NMR (CDCl₃, 600 MHz) δ 2.38 (s, 3H, CH₃Ph), 3.62 (dd, $J_{2'',3''}$=7.2 Hz, $J_{3'',4''}$=6.6 Hz, 1H, 3"-H), 3.67 (dd, $J_{4'',5''}$=4.8 Hz, $J_{5'',6''Ha/5'',6''Hb}$=3.6 Hz, 1H, 5"-H), 3.89 (d, $J_{4'',5''}$=3.0 Hz, 4"-H), 3.94 (dd, $J_{1'',2''}$=7.8 Hz, $J_{2'',3''}$=7.2 Hz, 1H, 2"-H), 4.02 (dd, $J_{5'',6''Hb}$=4.8 Hz, $J_{gem}$=11.4 Hz, 1H, 6"-Hb), 4.34 (dd, $J_{5'',6''Ha}$=5.4 Hz, $J_{gem}$=11.4 Hz, 1H, 6"-Ha), 4.80 (d, $J_{1'',2''}$=7.8 Hz, 1H, 1"-H), 5.09 and 5.24 (each s, each 2H, 2×CH₂Ph), 6.21 (d, 1H, $J_{trans}$=15.6 Hz, PhCH=CH—), 6.48 (d, ⁴J=1.8 Hz, 1H, 8-H), 6.59 (d, ⁴J=1.8 Hz, 1H, 6-H), 6.97 (d, J=7.8 Hz, 1H, 5'-H), 7.15 and 7.31 (each d, each 2H, each J=8.4 Hz, 2""-H & 6""-H, 3""-H & 5""-H), 7.33-7.42 (m, 18H, PhH), 7.53 (d, 1H, $J_{trans}$=16.2 Hz, PhCH=CH—), 7.55-7.59 (m, 4H, PhH), 7.78 (br s, 1H, 6'-H), 7.80 (d, ⁴J=1.8 Hz, 1H, 2'-H); FAB-MS m/z MH⁺ ion=1137 Anal. Calcd for $C_{58}H_{48}O_{13} \cdot \frac{1}{3}H_2O$: C, 72.46; H, 5.12. Found: C, 72.40; H, 5.06.

m) 5,7-Dibenzyloxy-2-(2,2-diphenylbenzo[d][1,3]dioxol-5-yl)-3-β-D-[6"-O-(4-fluorocinnamoyl)]galactosyl-4H-chromen-4-one (11m)

Yield 69%; IR (KBr) υ 1604 cm⁻¹ (C=C), 1634 and 1733 cm⁻¹ (C=O); 3462 cm⁻¹ (OH); ¹H NMR (CDCl₃, 600 MHz) δ 3.64 (dd, $J_{2'',3''}$=7.8 Hz, $J_{3'',4''}$=6.6 Hz, 1H, 3"-H), 3.69 (dd, $J_{4'',5''}$=4.8 Hz, $J_{5'',6''Ha/5'',6''Hb}$=3.6 Hz, 1H, 5"-H), 3.91 (d, $J_{4'',5''}$=3.0 Hz, 4"-H), 3.94 (dd, $J_{1'',2''}$=8.4 Hz, $J_{2'',3''}$=7.8 Hz, 1H, 2"-H), 4.09 (dd, $J_{5'',6''Hb}$=4.8 Hz, $J_{gem}$=11.4 Hz, 1H, 6"-Hb), 4.36 (dd, $J_{5'',6''Ha}$=5.4 Hz, $J_{gem}$=11.4 Hz, 1H, 6"-Ha), 4.82 (d, $J_{1'',2''}$=8.4 Hz, 1H, 1"-H), 5.09 and 5.24 (each s, each 2H, 2×CH₂Ph), 6.16 (d, 1H, $J_{trans}$=15.6 Hz, PhCH=CH—), 6.48 (d, ⁴J=1.8 Hz, 1H, 8-H), 6.58 (d, ⁴J=1.8 Hz, 1H, 6-H), 6.96 (d, J=7.8 Hz, 1H, 5'-H), 7.01 (t, 2H, J=9.0 Hz, 3""-H & 5""-H), 7.31 (d, 2H, J=8.4 Hz, 2""-H & 6""-H,), 7.33-7.39 (m, 18H, PhH), 7.47 (d, 1H, $J_{trans}$=16.2 Hz, PhCH=CH—), 7.55-7.59 (m, 4H, PhH), 7.79 (d, ⁴J=1.8 Hz, 1H, 2'-H), 7.81 (dd, J=8.4 Hz, ⁴J=1.8 Hz, 1H, 6'-H); FAB-MS m/z MH⁺ ion=1137 Anal. Calcd for $C_{57}H_{45}O_{13} \cdot \frac{1}{2}H_2O$: C, 70.87; H, 4.80. Found: C, 71.08; H, 5.13.

Example 2-7

Synthesis and Identification of Final Compounds 2a-b, 12, and 14a-m for Galactose Derivative (FIG. 3)

1, 3, or 11a-m (1.00 mmol) and 10% Pd—C (1 equivalent) were added to a mixed solution of EtOAc-EtOH (1:1, 30 mL), and the mixture was stirred vigorously under a hydrogen atmosphere at 0° C. to room temperature for 8 to 10 hours. Pd—C was removed by filtration, and the filtrate was then evaporated at 30° C. under reduced pressure. The residue was purified by flash column chromatography using a mixed solvent of EtOAc-n-hexane (4:1 or 2:1), to thereby obtain the corresponding compounds 2a-b, 12, or 14a-m.

2a) 2-(3',4'-Dihydroxyphenyl)-5-hydroxy-3,7-di-(4-methylphenylpropanoyl)-4H-chromen-4-one (2a)

Yield 69%; Melting point (m.p.) 105-107° C.; IR (KBr) υ 1605 cm$^{-1}$ (C=C), 1632 cm$^{-1}$ (C=O); $^1$H NMR (CDCl$_3$, 300 MHz) δ 3.37 and 3.39 (each s, each 3H, 2×CH$_3$Ph), 2.61 and 2.66 (each t, each 2H, J=7.2 Hz, 2×PhCH$_2$CH$_2$CO), 3.08 and 3.13 (each t, each 2H, J=7.8 Hz, 2×PhCH$_2$CH$_2$CO), 6.45 (d, $^4$J=1.8 Hz, 1H, 8-H), 6.61 (d, $^4$J=2.4 Hz, 1H, 6-H), 6.73 (d, J=8.4 Hz, 1H, 5'-H), 7.01-7.22 (m, 8H, PhH), 7.93 (dd, J=8.4 Hz, $^4$J=2.4 Hz, 1H, 6'-H), 7.98 (d, $^4$J=2.4 Hz, 1H, 2'-H), 9.59 (s, 1H, 3'-OH, D$_2$O exch.), 10.99 (s, 1H, 4'-OH, D$_2$O exch.), 12.34 (s, 1H, 5-OH, D$_2$O exch.); FAB-MS m/z MH$^+$ ion=595; Anal. Calcd for C$_{35}$H$_{30}$O$_9$: C, 70.70; H, 5.09. Found: C, 70.66; H, 4.98.

2b) 2-(3',4'-Dihydroxyphenyl)-5-hydroxy-3,7-di-(4-fluorophenylpropanoyl)-4H-chromen-4-one (2b)

Yield 66%; Melting point (m.p.) 119-121° C.; IR (KBr) υ 1606 cm$^{-1}$ (C=C), 1636; $^1$H NMR (CDCl$_3$, 300 MHz) δ 2.60 and 2.66 (each t, each 2H, J=7.2 Hz, 2×PhCH$_2$CH$_2$CO), 3.09 and 3.12 (each t, each 2H, J=7.8 Hz, 2×PhCH$_2$CH$_2$CO), 6.46 (d, $^4$J=1.8 Hz, 1H, 8-H), 6.61 (d, $^4$J=2.4 Hz, 1H, 6-H), 6.72 (d, J=8.4 Hz, 1H, 5'-H), 7.00-7.22 (m, 8H, PhH), 7.92 (dd, J=8.4 Hz, $^4$J=2.4 Hz, 1H, 6'-H), 7.99 (d, $^4$J=2.4 Hz, 1H, 2'-H), 9.57 (s, 1H, 3'-OH, D$_2$O exch.), 10.99 (s, 1H, 4'-OH, D$_2$O exch.), 12.33 (s, 1H, 5-OH, D$_2$O exch.); FAB-MS m/z MEI$^+$ ion=603; Anal. Calcd for C$_{33}$H$_{24}$F$_2$O$_9$: C, 65.78; H, 4.01. Found: C, 68.90; H, 4.38.

12) 2-(3',4'-Dihydroxyphenyl)-5,7-dihydroxy-3-β-D-tetraacetylgalactosyl-4H-chromen-4-one (12)

Yield 69%; Melting point (m.p.) 131-133° C.; IR (KBr) υ 1608 cm$^{-1}$ (C=C), 1656 cm$^{-1}$ and 1751 (C=O), 3425 cm$^{-1}$ (OH); $^1$H NMR (CDCl$_3$, 600 MHz) δ 1.77, 1.91, 2.02 and 2.11 (each s, each 3H, 4×CH$_3$CO), 3.81-3.86 (m, 2H, 4"-H, 5"-H), 4.16 (dd, J$_{2",3"}$=7.2 Hz, J$_{3",4"}$=6.6 Hz, 1H, 4"-H), 5.16 (dd, J$_{1",2"}$=7.8 Hz, J$_{2",3"}$=7.2 Hz, 1H, 2"-H), 5.19-5.25 (m, 2H, 6"-H), 5.61 (d, J$_{1",2"}$=7.8 Hz, 1H, 1"-H), 6.18 (d, $^4$J=1.8 Hz, 1H, 8-H), 6.38 (d, $^4$J=2.4 Hz, 1H, 6-H), 6.83 (d, J=8.1 Hz, 1H, 5'-H), 7.44 (d, $^4$J=2.4 Hz, 1H, 2'-H), 7.50 (dd, J=8.4 Hz, $^4$J=2.4 Hz, 1H, 6'-H), 9.15 (s, 1H, 3'-OH, D$_2$O exch.), 9.80 (s, 1H, 4'-OH, D$_2$O exch.), 10.87 (s, 1H, 7-OH, D$_2$O exch.), 12.56 (s, 1H, 5-OH, D$_2$O exch.); FAB-MS m/z MH$^+$ ion=633.

14a) 2-(3",4"-Dihydroxyphenyl)-5,7-dihydroxy-3-β-D-[2",6"-di-O-(4-ethoxybenzoyl)]galactosyl-4H-chromen-4-one (14a)

Yield 81%; Melting point (m.p.) 108-110° C.; IR (KBr) υ 1606 cm$^{-1}$ (C=C), 1651 and 1712 cm$^{-1}$ (C=O), 3416 cm$^{-1}$ (OH); $^1$H NMR (DMSO, 600 MHz) δ 1.32-1.34 (each t, each 3H, J=7.8 Hz, 2×CH$_3$CH$_2$), 3.81 (dd, J$_{3",4"}$=5.4 Hz, J$_{4",5"}$=3.6 Hz, 1H, 4"-H), 3.84-3.87 (m, 1H, 5"-H), 3.91 (dd, J$_{2",3"}$=8.4 Hz, J$_{3",4"}$=4.8 Hz, 1H, 3"-H), 4.02 and 4.09 (each q, each H, J=7.2 Hz, 2×CH$_3$CH$_2$), 4.21 (dd, J$_{5",6"Hb}$=3.0 Hz, J$_{gem}$=11.4 Hz, 1H, 6"-Hb), 4.26 (dd, J$_{5",6"Ha}$=4.2 Hz, J$_{gem}$=11.4 Hz, 1H, 6"-Ha), 5.13 (d, J=4.8 Hz, 3"-OH, D$_2$O exch.), 5.24 (d, J=6.6 Hz, 4"-OH, D$_2$O exch.), 5.34 (dd, J$_{2",3"}$=8.4 Hz, J$_{1",2"}$=7.8 Hz, 1H, 2"-H), 5.82 (d, J$_{1",2"}$=7.8 Hz, 1H, 1"-H), 6.16 (d, $^4$J=2.4 Hz, 1H, 8-H), 6.32 (d, $^4$J=2.4 Hz, 1H, 6-H), 6.73 and 7.02 (each d, each 2H, each J=8.4 Hz, 2×3'''-H, 2×5'''-H), 6.80 (d, J=8.4 Hz, 1H, 5'-H), 7.38 (d, $^4$J=2.4 Hz, 1H, 2'-H), 7.58 and 7.94 (each d, each 2H, each J=9.0 Hz, 2×2'''-H, 2×6'''-H), 7.63 (dd, J=8.4 Hz, $^4$J=1.8 Hz, 1H, 6'-H), 9.14 (s, 1H, 3'-OH, D$_2$O exch.), 9.80 (s, 1H, 4'-OH, D$_2$O exch.), 10.84 (s, 1H, 7-OH, D$_2$O exch.), 12.60 (s, 1H, 5-OH, D$_2$O exch.); $^{13}$C NMR (DMSO, 150 MHz) δ 14.68 and 14.71 (2×CH$_3$), 63.55 (5"-C), 63.67 and 63.71 (2×OCH$_2$Ph), 68.70 (6"-C), 71.08 (4"-C), 73.01 (2"-C), 73.41 (3"-C), 93.63 (1"-C), 98.65 (8-C), 98.81 (6-C), 103.92 (4a-C), 114.16 (2×3'''-C, 2×5'''-C), 114.40 (2'-C), 115.34 (5'-C), 115.73 (6'-C), 121.02 (3-C), 121.68 and 122.28 (2×2'''-C, 2×6'''-C), 122.40 131.01 (2×1'''-C), 132.80 (2-C), 145.17 (1'-C), 148.77 (3'-C), 156.37 (4'-C), 156.50 (1a-C), 161.41 (5-C), 162.47 and 162.57 (2×4'''-C), 164.26 (7-C), 165.03 and 165.17 (2×C=O), 177.27 (4-C); FAB-MS m/z MH$^+$ ion=761; Anal. Calcd for C$_{39}$H$_{36}$O$_{16}$·¼H$_2$O: C, 61.22; H, 4.81 C. Found: C, 61.11; H, 4.68.

14b) 2-(3',4'-Dihydroxyphenyl)-5,7-dihydroxy-3-β-D-[2",6"-di-O-(4-propylbenzoyl)]galactosyl-4H-chromen-4-one (14b)

Yield 78%; Melting point (m.p.) 150-151° C.; IR (KBr) υ 1604 cm$^{-1}$ (C=C), 1654 and 1712 cm$^{-1}$ (C=O), 3419 cm$^{-1}$ (OH); $^1$H NMR (DMSO, 600 MHz) δ 0.86 and 0.88 (each t, each 3H, J=7.2 Hz, 2×CH$_3$CH$_2$), 1.53-1.63 (m, 4H, 2×CH$_3$CH$_2$CH$_2$), 2.55 and 2.62 (each t, each 2H, J=7.2 Hz, 2×CH$_3$CH$_2$CH$_2$), 3.81 (br s, 1H, 4"-H), 3.86-3.89 (m, 1H, 5"-H), 3.93 (dd, J$_{2",3"}$=8.4 Hz, J$_{3",4"}$=4.8 Hz, 1H, 3"-H), 4.23 (dd, J$_{5",6"Hb}$=3.0 Hz, J$_{gem}$=11.4 Hz, 1H, 6"-Hb), 4.29 (dd, J$_{5",6"Ha}$=4.2 Hz, J$_{gem}$=11.4 Hz, 1H, 6"-Ha), 5.15 (d, J=4.2 Hz, 3"-OH, D$_2$O exch.), 5.27 (d, J=6.6 Hz, 4"-OH, D$_2$O exch.), 5.36 (dd, J$_{1",2"}$=7.8 Hz, J$_{2",3"}$=8.4 Hz, 1H, 2"-H), 5.84 (d, J$_{1",2"}$=7.8 Hz, 1H, 1"-H), 6.16 (d, $^4$J=2.4 Hz, 1H, 8-H), 6.30 (d, $^4$J=2.4 Hz, 1H, 6-H), 6.80 (d, J=8.4 Hz, 1H, 5'-H), 7.05 and 7.34 (each d, each 2H, each J=8.4 Hz, 2×3'''-H, 2×5'''-H), 7.39 (d, $^4$J=2.4 Hz, 1H, 2'-H), 7.56 and 7.94 (each d, each 2H, each J=9.0 Hz, 2×2'''-H, 2×6'''-H), 7.62 (dd, J=8.4 Hz, $^4$J=2.4 Hz, 1H, 6'-H), 9.14 (s, 1H, 3'-OH, D$_2$O exch.), 9.80 (s, 1H, 4'-OH, D$_2$O exch.), 10.85 (s, 1H, 7-OH, D$_2$O exch.), 12.59 (s, 1H, 5-OH, D$_2$O exch.); $^{13}$C NMR (DMSO, 150 MHz) δ 13.74 and 13.78 (2×CH$_3$), 23.79 and 24.01 (2×CH$_2$), 37.33 (2×CH$_2$Ph), 63.75 (5"-C), 68.69 (6"-C), 71.04 (4"-C), 73.23 (2"-C), 73.34 (3"-C), 93.65 (1"-C), 98.62 (8-C), 98.86 (6-C), 103.94 (4a-C), 115.36 (2'-C), 115.75 (5'-C), 121.02 (6'-C), 122.36 (3-C), 127.24 and 127.82 (2×1'''-C), 128.58 and 128.76 (2×3'''-C, 2×5'''-C), 128.98 and 129.01 (2×2'''-C, 2×6'''-C), 129.70 (2-C), 132.79 (1'-C), 145.18 (3'-C), 148.08 and 148.18 (2×4'''-C), 148.79 (4'-C), 156.34 (5-C), 161.41 (1a-C), 164.34 (7-C), 165.37 and 165.51 (2×C=O), 177.26 (4-C); FAB-MS m/z MH$^+$ ion=757; Anal. Calcd for C$_{41}$H$_{40}$O$_{14}$: C, 65.07; H, 5.33. Found: C, 65.01; H, 5.48.

14c) 2-(3',4'-Dihydroxyphenyl)-5,7-dihydroxy-3-β-D-[2",6"-di-O-(4-fluorobenzoyl)]galactosyl-4H-chromen-4-one (14c)

Yield 75%; Melting point (m.p.) 163-164° C.; IR (KBr) υ 1608 cm$^{-1}$ (C=C), 1654 and 1705 cm$^{-1}$ (C=O), 3406 cm$^{-1}$ (OH); $^1$H NMR (DMSO, 600 MHz) δ 3.82 (br s, 1H, 4"-H), 3.86-3.89 (m, 1H, 5"-H), 3.93 (dd, J$_{2",3"}$=8.4 Hz, J$_{3",4"}$=4.2 Hz, 1H, 3"-H), 4.26 (dd, J$_{5",6"Hb}$=4.2 Hz, J$_{gem}$=11.4 Hz, 1H, 6"-Hb), 4.34 (dd, J$_{5",6"Ha}$=3.0 Hz, J$_{gem}$=11.4 Hz, 1H, 6"-Ha), 5.17 (d, J=4.2 Hz, 4"-OH, D$_2$O exch.), 5.31 (d, J=6.6 Hz, 1H, 4"-OH, D$_2$O exch.), 5.34 (dd, J$_{1",2"}$=7.8 Hz, J$_{2",3"}$=8.4 Hz, 1H, 2"-H), 5.74 (d, J$_{1",2"}$=7.8 Hz, 1H, 1"-H), 6.13 (d, $^4$J=2.4 Hz, 1H, 8-H), 6.28 (d, $^4$J=2.4 Hz, 1H, 6-H), 6.78 (d, J=8.4 Hz, 1H, 5'-H), 7.09 and 7.36 (each t, each 2H, each J=9.0 Hz, 2×3'''-H, 2×5'''-H), 7.37 (d, $^4$J=2.4 Hz, 1H, 2'-H), 7.58 (dd, J=8.4 Hz, $^4$J=2.4 Hz, 1H, 6'-H), 7.73 and 8.07 (each dd, each 2H, J=8.4

Hz, J=9.0 Hz, J=5.4 Hz, 2×2'''-H, 2×6'''-H), 9.14 (s, 1H, 3'-OH, D₂O), 9.79 (s, 1H, 4'-OH, D₂O exch.), 10.84 (s, 1H, 7-OH, D₂O exch.), 12.54 (s, 1H, 5-OH, D₂O exch.); ¹³C NMR (DMSO, 150 MHz) δ 63.85 (5"-C), 68.59 (6"-C), 70.96 (4"-C), 73.29 (2"-C), 73.56 (3"-C), 93.61 (1"-C), 98.84 (8-C), 99.47 (6-C), 103.87 (4a-C), 115.33 (2'-C), 115.64-115.84 (2×3'''-C, 2×5'''-C), 115.98 (5'-C), 120.94 (6'-C), 122.29 (3-C), 126.20 and 126.80 (2×1'''-C), 131.73-131.80 (2×2'''-C, 2×6'''-C), 132.43 (2-C), 132.88 (1'-C), 145.13 (3'-C), 148.77 (4'-C), 156.31 (5-C), 164.52 and 164.95 (2×4'''-C), 161.32 (1a-C), 164.28 (7-C), 164.44 and 164.49 (2×C=O), 177.17 (4-C); FAB-MS m/z MH⁺ ion=709; Anal. Calcd for $C_{35}H_{26}O_{14}F_2$: C, 59.33; H, 3.70. Found: C, 58.12; H, 4.01.

14d) 2-(3',4'-Dihydroxyphenyl)-5,7-dihydroxy-3-β-D-[2",6"-di-O-(4-methylphenylacetyl)]galactosyl-4H-chromen-4-one (14d)

Yield 79%; Melting point (m.p.) 125-127° C.; IR (KBr) υ 1606 cm⁻¹ (C=C), 1651 and 1728 cm⁻¹ (C=O), 3410 cm⁻¹ (OH); ¹H NMR (CDCl₃, 600 MHz) δ 2.20 and 2.21 (each s, each 3H, 2×CH₃Ph), 3.30/3.37 (each AB system, each d, each $J_{AB}$=15.6 Hz, 2H, PhCH₂CO), 3.66 (br s, 2H, PhCH₂CO), 3.69-3.72 (m, 2H, 4"-H, 5"-H), 3.97-4.04 (m, 3H, 3"-H, 6"-H), 5.00 (d, J=4.8 Hz, 1H, 3"-OH), 5.105 (dd, $J_{1",2"}$=7.8 Hz, $J_{2",3"}$=6.6 Hz, 1H, 2"-H), 5.18 (d, J=6.0 Hz, 1H, 4"-OH), 5.54 (d, $J_{1",2"}$=7.8 Hz, 1H, 1"-H), 6.20 (d, ⁴J=2.4 Hz, 1H, 8-H), 6.40 (d, ⁴J=1.8 Hz, 1H, 6-H), 6.78 (d, J=8.4 Hz, 1H, 5'-H), 6.90 and 6.96 (each d, each 2H, J=8.4 Hz, 2×3''''-H, 2×5''''-H), 7.04 and 7.14 (each d, each 2H, J=8.4 Hz, 2×2''''-H, 2×6''''-H), 7.45 (d, ⁴J=2.4 Hz, 1H, 2'-H), 7.61 (dd, J=8.4 Hz, ⁴J=2.4 Hz, 1H, 6'-H), 9.13 (s, 1H, 3'-OH, D₂O exch.), 9.78 (s, 1H, 4'-OH, D₂O exch.), 10.87 (s, 1H, 7-OH, D₂O exch.), 12.70 (s, 1H, 5-OH, D₂O exch.); ¹³C NMR (DMSO, 150 MHz) δ 20.80 and 20.82 (2×PhCH₃), 38.77 and 38.28 (2×2'''-C), 63.80 (5"-C), 68.60 (6"-C), 70.64 (4"-C), 72.90 (2"-C), 72.97 (3"-C), 93.73 (1"-C), 98.88 (8-C), 99.25 (6-C), 104.06 (4a-C), 115.30 (2'-C), 115.80 (5'-C), 120.96 (6'-C), 122.41 (3-C), 128.92 and 128.95 (2×2''''-C, 2×6''''-C), 129.16 and 129.98 (2×3''''-C, 2×5''''-C), 131.15 (2-C), 131.53 (1'-C), 133.24 and 133.79 (2×1''''-C), 135.82 and 135.94 (2×4''''-C), 145.13 (3'-C), 150.66 (4'-C), 156.56 (5-C), 161.51 (1a-C), 164.40 (7-C), 170.88 and 171.01 (2×C=O), 177.24 (4-C); FAB-MS m/z MH⁺ ion=729; Anal. Calcd for $C_{39}H_{36}O_{14}$: C, 64.28; H, 4.98. Found: C, 64.46; H, 4.71.

14e) 2-(3',4'-Dihydroxyphenyl)-5,7-dihydroxy-3-β-D-[2",6"-di-O-(4-fluorophenylacetyl)]galactosyl-4H-chromen-4-one (14e)

Yield 77%; Melting point (m.p.) 139-141° C.; IR (KBr) υ 1602 cm⁻¹ (C=C), 1651 and 1728 cm⁻¹ (C=O), 3435 cm⁻¹ (OH); ¹H NMR (CDCl₃, 600 MHz) δ 3.37/3.45 (each AB system, each d, $J_{AB}$=15.6 Hz, 2H, PhCH₂CO), 3.67 (br s, 1H, 4"-H), 3.70-3.74 (m, 4H, PhCH₂CO, 3"-H, 5"-H), 3.99 (dd, $J_{5",6"Hb}$=4.2 Hz, $J_{gem}$=11.4 Hz, 1H, 6"-Hb), 4.04 (dd, $J_{5",6"Ha}$=3.0 Hz, $J_{gem}$=11.4 Hz, 1H, 6"-Ha), 5.01 (br s, 3"-OH, D₂O exch.), 5.11 (dd, $J_{1",2"}$=7.8 Hz, $J_{2",3"}$=7.2 Hz, 1H, 2"-H), 5.20 (br s, 3"-OH, D₂O exch.), 5.50 (d, $J_{1",2"}$=7.8 Hz, 1H, 1"-H), 6.19 (d, ⁴J=2.4 Hz, 1H, 8-H), 6.40 (d, ⁴J=2.4 Hz, 1H, 6-H), 6.76 (d, J=8.4 Hz, 1H, 5'-H), 6.99 and 7.04 (each t, each 2H, J=9.0 Hz, 2×3''''-H, 2×5''''-H), 7.07 and 7.30 (each dd, each 2H, J=8.4 Hz, J=9.0 Hz, 2×2''''-H, 2×6''''-H), 7.45 (d, ⁴J=2.4 Hz, 1H, 2'-H), 7.60 (dd, J=8.4 Hz, ⁴J=2.4 Hz, 1H, 6'-H), 9.14 (s, 1H, 3'-OH, D₂O exch.), 9.79 (s, 1H, 4'-OH, D₂O exch.), 10.88 (s, 1H, 7-OH, D₂O exch.), 12.68 (s, 1H, 5-OH, D₂O exch.); ¹³C NMR (DMSO, 150 MHz) δ 31.36 and 31.72 (2×2'''-C), 63.97 (5"-C), 68.70 (6"-C), 70.84 (4"-C), 73.10 (2"-C), 73.22 (3"-C), 93.95 (1"-C), 99.10 (8-C), 99.54 (6-C), 104.22 (4a-C), 115.21-115.35 (2×3''''-C, 2×5''''-C), 115.49 (2'-C), 116.01 (5'-C), 121.14 (6'-C), 122.58 (3-C), 130.64 and 131.04 (2×1''''-C), 131.48-131.77 (2×2''''-C, 2×6''''-C), 133.48 (2-C), 134.23 (1'-C), 145.33 (3'-C), 149.02 (4'-C), 156.63 (5-C), 160.69 (1a-C), 161.66 and 162.30 (2×4''''-C), 164.63 (7-C), 170.90 and 171.04 (2×C=O), 177.45 (4-C); FAB-MS m/z MH⁺ ion=737; Anal. Calcd for $C_{37}H_{30}O_{14}F_2$: C, 60.33; H, 4.10. Found: C, 60.05; H, 4.15.

14f) 2-(3',4'-Dihydroxyphenyl)-5,7-dihydroxy-3-β-D-{2",6"-di-O-[3'''-(4-hydroxyphenylpropanoyl)]}galactosyl-4H-chromen-4-one (14f)

Yield 0.60 g (79%); Melting point (m.p.) 149-150° C.; Melting point (m.p.) 173-174° C.; IR (KBr) υ 1608 cm⁻¹ (C=C), 1651 and 1728 cm⁻¹ (C=O), 3383 cm⁻¹ (OH); ¹H NMR (DMSO, 600 MHz) δ 2.29 and 2.46 (each t, each 2H, J=7.8 Hz, 2×PhCH₂CH₂CO), 2.55 and 2.73 (each t, each 2H, J=7.8 Hz, 2×PhCH₂CH₂CO), 3.66-3.70 (m, 3H, 3"-H, 4"-H, 5"-H), 3.95 (dd, $J_{5",6"Hb}$=4.2 Hz, $J_{gem}$=11.4 Hz, 1H, 6"-Hb), 4.01 (dd, $J_{5",6"Ha}$=4.8 Hz, $J_{gem}$=11.4 Hz, 1H, 6"-Ha), 4.99 (d, J=4.2 Hz, 3"-OH, D₂O exch.), 5.11 (dd, $J_{1",2"}$=7.8 Hz, $J_{2",3"}$=7.2 Hz, 1H, 2"-H), 5.14 (d, J=4.2 Hz, 2"-OH, D₂O exch.), 5.52 (d, $J_{1",2"}$=7.8 Hz, 1H, 1"-H), 6.14 (d, ⁴J=1.8 Hz, 1H, 8-H), 6.34 (d, ⁴J=1.8 Hz, 1H, 6-H), 6.57 and 6.60 (each d, each 2H, each J=8.4 Hz, 2×3''''-H, 2×5''''-H), 6.79 (d, J=8.4 Hz, 1H, 5'-H), 6.81 and 6.99 (each d, each 2H, each J=8.4 Hz, 2×2''''-H, 2×6''''-H), 7.44 (d, ⁴J=2.4 Hz, 1H, 2'-H), 7.61 (dd, J=8.4 Hz, ⁴J=2.4 Hz, 1H, 6'-H), 9.10 (s, 1H, PhOH, D₂O exch.), 9.13 (s, 1H, PhOH, D₂O exch.), 9.28 (s, 1H, 3'-OH, D₂O exch.), 9.79 (s, 1H, 4'-OH, D₂O exch.), 10.83 (s, 1H, 7-OH, D₂O exch.), 12.65 (s, 1H, 5-OH, D₂O exch.); ¹³C NMR (DMSO, 150 MHz) δ 29.57 and 29.61 (2×2'''-C), 35.65 and 36.02 (2×3'''-C), 63.21 (5"-C), 68.54 (6"-C), 70.61 (4"-C), 72.54 (2"-C), 73.02 (3"-C), 93.68 (1"-C), 95.77 (8-C), 99.12 (6-C), 104.01 (4a-C), 115.20 and 115.22 (2×3''''-C, 2×5''''-C), 115.33 (2'-C), 115.81 (5'-C), 121.02 (6'-C), 122.41 (3-C), 129.12 and 129.28 (2×2''''-C, 2×6''''-C), 130.52 (1'-C), 130.87 (2×1''''-C), 133.22 (2-C), 145.15 (3'-C), 148.79 (4'-C), 155.70 and 155.89 (2×4''''-C), 156.52 (5-C), 161.42 (1a-C), 164.36 (7-C), 171.85 and 171.96 (2×C=O), 177.30 (4-C); FAB-MS m/z MH⁺ ion=761; Anal. Calcd for $C_{39}H_{36}O_{16}$: C, 61.58; H, 4.77. Found: C, 61.52; H, 4.97.

14g) 2-(3',4'-Dihydroxyphenyl)-5,7-dihydroxy-3-β-D-{2",6"-di-O-[3'''-(4-ethoxyphenylpropanoyl)]}galactosyl-4H-chromen-4-one (14g)

Yield 83%; Melting point (m.p.) 108-110° C.; IR (KBr) υ 1608 cm⁻¹ (C=C), 1654 and 1728 cm⁻¹ (C=O), 3414 cm⁻¹ (OH); ¹H NMR (DMSO, 600 MHz) δ 1.21 and 1.29 (each t, each 3H, J=7.8 Hz, 2×CH₃CH₂), 2.30 and 2.52 (each t, each 2H, J=7.8 Hz, 2×PhCH₂CH₂CO), 2.59 and 2.78 (each t, each 2H, J=7.8 Hz, 2×PhCH₂CH₂CO), 3.65-3.70 (m, 3H, 3"-H, 4"-H, 5"-H), 3.82 and 3.92 (each q, each 2H, J=7.2 Hz, 2×CH₃CH₂), 3.95 (dd, $J_{5",6"Hb}$=4.2 Hz, $J_{gem}$=11.4 Hz, 1H, 6"-Hb), 4.01 (dd, $J_{5",6"Ha}$=4.8 Hz, $J_{gem}$=11.4 Hz, 1H, 6"-Ha), 5.00 (d, J=4.2 Hz, 1H, 3"-OH, D₂O exch.), 5.11 (dd, $J_{1",2"}$=8.4 Hz, $J_{2",3"}$=7.8 Hz, 1H, 2"-H), 5.16 (d, J=5.4 Hz, 1H, 4"-OH, D₂O exch.), 5.55 (d, $J_{1",2"}$=8.4 Hz, 1H, 1"-H), 6.14 (d, ⁴J=1.8 Hz, 1H, 8-H), 6.31 (d, ⁴J=1.8 Hz, 1H, 6-H), 6.66 and 6.70 (each d, each 2H, each J=9.0 Hz, 2×3''''-H, 2×5''''-H), 6.80 (d, J=8.4 Hz, 1H, 5'-H), 6.89 and 7.08 (each d, each 2H, each J=9.0 Hz, 2×2''''-H, 2×6''''-H), 7.43 (d, ⁴J=2.4 Hz, 1H, 2'-H), 7.62 (dd, J=8.4 Hz, ⁴J=2.4 Hz, 1H, 6'-H), 9.14 (s, 1H, 3'-OH, D₂O exch.), 9.81 (s, 1H, 4'-OH, D₂O exch.), 10.82 (s, 1H, 7-OH, D₂O), 12.65 (s, 1H, 5-OH, D₂O); $^{13}$C NMR (DMSO, 150 MHz) δ 14.83 and 14.92 (2×CH₃), 29.53 and 29.79 (2×2'''-C), 35.61 and 35.81 (2×3'''-C), 62.88 and 62.98 (2×CH₂), 63.34 (5"-C), 68.57 (6"-C), 70.71 (4"-C), 72.54 (2"-C), 73.05 (3"-C), 93.63 (1"-C), 98.85 (8-C), 98.98 (6-C), 103.98 (4a-C), 114.18 and 114.26 (2×3''''-C, 2×5''''-C), 115.32 (2'-C), 115.75 (5'-C), 121.01 (6'-C), 122.46 (3-C), 129.16 and 129.37 (2×2''''-C, 2×6''''-C), 132.13 and 132.46 (2×1''''-C), 133.16 (2-C), 134.99 (1'-C), 145.15 (3'-C), 148.79 (4'-C), 156.35 (5-C), 156.92 and 156.98 (2×4''''-C), 161.40 (1a-C), 164.33 (7-C), 171.83 and 171.90 (2×C=O), 177.25 (4-C); FAB-MS m/z MH⁺ ion=817; Anal. Calcd for C₄₃H₄₄O₁₆: C, 63.23; H, 5.43. Found: C, 63.34; H, 5.50.

14h) 2-(3',4'-Dihydroxyphenyl)-5,7-dihydroxy-3-β-D-{2",6"-di-O-[3'''-(4-methylphenylpropanoyl)]}galactosyl-4H-chromen-4-one (14h)

Yield 78%; Melting point (m.p.) 123-124° C.; IR (KBr) υ 1606 cm⁻¹ (C=C), 1653 and 1728 cm⁻¹ (C=O); 3408 cm⁻¹ (OH); $^1$H NMR (DMSO, 600 MHz) δ 2.15 and 2.22 (each s, each 3H, 2×CH₃Ph), 2.35 and 2.55 (each t, each 2H, J=7.8 Hz, 2×PhCH₂CH₂CO), 2.61 and 2.81 (each t, each 2H, J=7.8 Hz, 2×PhCH₂CH₂CO), 3.66-3.70 (m, 3H, 3"-H, 4"-H, 5"-H), 3.97 (dd, 1H, $J_{5'',6''Hb}$=4.2 Hz, $J_{gem}$=11.4 Hz, 1H, 6"-Hb), 4.02 (dd, $J_{5'',6''Ha}$=4.2 Hz, $J_{gem}$=11.4 Hz, 1H, 6"-Ha), 5.00 (d, J=3.6 Hz, 1H, 3"-OH, D₂O exch.), 5.11 (dd, $J_{1'',2''}$=8.4 Hz, $J_{2'',3''}$=7.8 Hz, 1H, 2"-H), 5.15 (d, J=5.4 Hz, 1H, 4"-OH, D₂O exch.), 5.52 (d, $J_{1'',2''}$=8.4 Hz, 1H, 1"-H), 6.15 (d, $^4$J=1.8 Hz, 1H, 8-H), 6.32 (d, $^4$J=1.8 Hz, 1H, 6-H), 6.90 and 6.96 (each d, each 2H, each J=8.4 Hz, 2×2''''-H, 2×6''''-H), 6.95 (d, J=8.4 Hz, 1H, 5'-H), 6.99 and 7.08 (each d, each 2H, each J=8.4 Hz, 2×3''''-H, 2×5''''-H), 7.44 (d, $^4$J=2.4 Hz, 1H, 2'-H), 7.61 (dd, J=8.4 Hz, $^4$J=2.4 Hz, 1H, 6'-H), 9.14 (s, 1H, 3'-OH, D₂O exch.), 9.80 (s, 1H, 4'-OH, D₂O exch.), 10.82 (s, 1H, 7-OH, D₂O exch.), 12.65 (s, 1H, 5-OH, D₂O exch.); $^{13}$C NMR (DMSO, 150 MHz) δ 21.27 and 21.37 (2×PhCH₃), 30.50 and 30.53 (2×2'''-C), 35.92 and 36.21 (2×3'''-C), 63.86 (5"-C), 69.08 (6"-C), 71.26 (4"-C), 73.11 (2"-C), 73.56 (3"-C), 94.18 (1"-C), 96.15 (8-C), 99.69 (6-C), 104.57 (4a-C), 115.86 (2'-C), 116.34 (5'-C), 121.56 (6'-C), 122.96 (3-C), 128.62 and 128.83 (2×2''''-C, 2×6''''-C), 129.50 and 129.54 (2×3''''-C, 2×5''''-C), 133.77 (2-C), 134.98 (1'-C), 135.50 and 135.60 (2×4''''-C), 137.86 and 138.21 (2×1''''-C), 145.68 (3'-C), 149.32 (4'-C), 156.97 (5-C), 161.96 (1a-C), 164.86 (7-C), 172.33 and 172.43 (2×C=O), 177.80 (4-C); FAB-MS m/z MH⁺ ion=757; Anal. Calcd for C₄₁H₄₀O₁₄: C, 65.07; H, 5.33. Found: C, 64.87; H, 5.08.

14i) 2-(3',4'-Dihydroxyphenyl)-5,7-dihydroxy-3-β-D-{2",6"-di-O-[3'''-(4-fluorophenylpropanoyl)]}galactosyl-4H-chromen-4-one (14i)

Yield 77%; Melting point (m.p.) 116-118° C.; IR (KBr) υ 1606 cm⁻¹ (C=C), 1653 and 1732 cm⁻¹ (C=O), 3390 cm⁻¹ (OH); $^1$H NMR (DMSO, 600 MHz) δ 2.36 and 2.57 (each t, each 2H, J=7.8 Hz, 2×PhCH₂CH₂CO), 2.64 and 2.86 (each t, each 2H, J=7.8 Hz, 2×PhCH₂CH₂CO), 3.67-3.72 (m, 3H, 3"-H, 4"-H, 5"-H), 3.97 (dd, 1H, $J_{5'',6''Hb}$=4.2 Hz, $J_{gem}$=11.4 Hz, 1H, 6"-Hb), 4.03 (dd, 1H, $J_{5'',6''Ha}$=3.6 Hz, $J_{gem}$=11.4 Hz, 1H, 6"-Ha), 5.01 (d, J=4.8 Hz, 1H, 3"-OH, D₂O exch.), 5.12 (dd, $J_{1'',2''}$=7.8 Hz, $J_{2'',3''}$=7.2 Hz, 1H, 2"-H), 5.16 (d, J=6.0 Hz, 1H, 4"-OH, D₂O exch.), 5.54 (d, $J_{1'',2''}$=7.8 Hz, 1H, 1"-H), 6.13 (d, $^4$J=2.4 Hz, 1H, 8-H), 6.31 (d, $^4$J=2.4 Hz, 1H, 6-H), 6.81 (d, J=8.4 Hz, 1H, 5'-H), 6.96 and 6.98 (each t, each 2H, J=9.0 Hz, 2×3''''-H, 2×5''''-H), 7.05 and 7.24 (each dd, each 2H, J=9.0 Hz, J=8.4 Hz, 2×2''''-H, 2×6''''-H), 7.44 (d, $^4$J=2.4 Hz, 1H, 2'-H), 7.61 (dd, J=8.4 Hz, $^4$J=2.4 Hz, 1H, 6'-H), 9.14 (s, 1H, 3'-OH, D₂O exch.), 9.80 (s, 1H, 4'-OH, D₂O exch.), 10.81 (s, 1H, 7-OH, D₂O exch.), 12.64 (s, 1H, 5-OH, D₂O exch.); $^{13}$C NMR (DMSO, 150 MHz) δ 30.06 and 30.09 (2×2'''-C), 35.87 and 36.11 (2×3'''-C), 63.92 (5"-C), 69.10 (6"-C), 71.28 (4"-C), 73.15 (2"-C), 73.57 (3"-C), 94.18 (1"-C), 99.38 (8-C), 99.61 (6-C), 104.53 (4a-C), 115.46-115.66 (2×3''''-C, 2×5''''-C), 115.87 (2'-C), 116.32 (5'-C), 121.54 (6'-C), 122.93 (3-C), 130.52-130.81 (2×2''''-C, 2×6''''-C), 133.71 (2-C), 134.99 (1'-C), 137.40 and 137.42 (2×1''''-C), 145.69 (3'-C), 149.33 (4'-C), 156.87 (5-C), 160.62 (1a-C), 161.93 and 162.20 (2×4''''-C), 164.86 (7-C), 172.28 and 172.34 (2×C=O), 177.82 (4-C); FAB-MS m/z MH⁺ ion=765; Anal. Calcd for C₃₉H₃₄O₁₄F₂: C, 61.26; H, 4.48. Found: C, 60.84; H, 4.6.

14j) 2-(3',4'-Dihydroxyphenyl)-5,7-dihydroxy-3-β-D-{2",6"-di-O-[3'''-(4-fluorophenylbutanoyl)]}galactosyl-4H-chromen-4-one (14j)

Yield 79%; Melting point (m.p.) 108-109° C.; IR (KBr) υ 1604 cm⁻¹ (C=C), 1654 and 1724 cm⁻¹ (C=O), 3421 cm⁻¹ (OH); $^1$H NMR (DMSO, 600 MHz) δ 1.54 and 1.80 (each quintet, 9H, 2×PhCH₂CH₂CH₂), 1.98 and 2.02 (each t, each 2H, J=7.2 Hz, 2×CH₂CH₂CO), 2.33 and 2.55 (each t, each 2H, J=7.2 Hz, 2×PhCH₂CH₂), 3.67-3.74 (m, 3H, 3"-H, 4"-H, 5"-H), 3.93 (dd, 1H, $J_{5'',6''Hb}$=3.6 Hz, $J_{gem}$=11.4 Hz, 1H, 6"-Hb), 4.09 (dd, 1H, $J_{5'',6''Ha}$=3.0 Hz, $J_{gem}$=11.4 Hz, 1H, 6"-Ha), 5.00 (br s, 1H, 3"-OH, D₂O exch.), 5.11 (dd, $J_{1'',2''}$=7.8 Hz, $J_{2'',3''}$=8.4 Hz, 1H, 2"-H), 5.14 (br s, 1H, 4"-OH, D₂O exch.), 5.55 (d, $J_{1'',2''}$=7.8 Hz, 1H, 1"-H), 6.17 (d, $^4$J=2.4 Hz, 1H, 8-H), 6.33 (d, $^4$J=2.4 Hz, 1H, 6-H), 6.79 (d, J=8.4 Hz, 1H, 5'-H), 6.99 and 7.01 (each t, each 2H, J=9.0 Hz, 2×3''''-H, 2×5''''-H), 7.05 and 7.16 (each dd, each 2H, J=9.0 Hz, J=8.4 Hz, 2×2''''-H, 2×6''''-H), 7.42 (d, $^4$J=2.4 Hz, 1H, 2'-H), 7.63 (dd, J=8.4 Hz, $^4$J=2.4 Hz, 1H, 6'-H), 9.14 (s, 1H, 3'-OH, D₂O exch.), 9.80 (s, 1H, 4'-OH, D₂O exch.), 10.85 (s, 1H, 7-OH, D₂O), 12.59 (s, 1H, 5-OH, D₂O exch.); $^{13}$C NMR (DMSO, 150 MHz) δ 26.17 and 26.43 (2×3'''-C), 31.03 and 31.15 (2×2'''-C), 36.79 and 36.87 (2×4'''-C), 63.07 (5"-C), 68.38 (6"-C), 70.51 (4"-C), 72.21 (2"-C), 72.84 (3"-C), 93.41 (1"-C), 98.61 (8-C), 98.81 (6-C), 103.76 (4a-C), 113.99-114.89 (2×3''''-C, 2×5''''-C), 115.10 (2'-C), 115.56 (5'-C), 120.75 (6'-C), 122.18 (3-C), 129.91-130.04 (2×2''''-C, 2×6''''-C), 132.90 (2-C), 134.99 (1'-C), 137.23 and 137.61 (2×1''''-C), 144.94 (3'-C), 148.60 (4'-C), 156.16 (5-C), 159.76 (1a-C), 161.21 and 161.36 (2×4''''-C), 164.20 (7-C), 171.95 and 172.10 (2×C=O), 177.01 (4-C); FAB-MS m/z MH⁺ ion=793; Anal. Calcd for C₄₁H₃₈O₁₄F₂·⅕H₂O: C, 61.84.12; H, 4.86. Found: C, 61.84; H, 4.97.

14k) 2-(3',4'-Dihydroxyphenyl)-5,7-dihydroxy-3-β-D-{2",6"-di-O-[3'''-(4-fluorophenylpentanoyl)]}galactosyl-4H-chromen-4-one (14k)

Yield 81%; Melting point (m.p.) 91-93° C.; IR (KBr) υ 1606 cm⁻¹ (C=C), 1651 and 1728 cm⁻¹ (C=O), 3404 cm⁻¹ (OH); $^1$H NMR (DMSO, 600 MHz) δ 1.22-1.30 (m, 4H, 2×PhCH₂CH₂CH₂), 1.33 and 1.52 (each quintet, each 2H, J=7.2 Hz, 2×CH₂CH₂CH₂CH₂), 1.58 and 2.02 (each t, each 2H, J=7.2 Hz, 2×CH₂CH₂CO), 2.35 and 2.52 (each t, each 2H, J=7.2 Hz, 2×PHCH₂CH₂), 3.65-3.71 (m, 3H, 3"-H, 4"-H, 5"-H), 3.92 (dd, 1H, $J_{5'',6''Hb}$=4.2 Hz, $J_{gem}$=11.4 Hz, 1H, 6"-Hb), 4.09 (dd, 1H, $J_{5'',6''Ha}$=3.6 Hz, $J_{gem}$=11.4 Hz, 1H, 6"-Ha), 5.00 (d, J=4.2 Hz, 1H, 3"-OH, D₂O exch.), 5.09 (dd, $J_{1'',2''}$=7.8 Hz, $J_{2'',3''}$=8.4 Hz, 1H, 2"-H), 5.13 (d, J=6.0 Hz, 1H, 4"-OH, D₂O exch.), 5.54 (d, $J_{1'',2''}$=7.8 Hz, 1H, 1"-H), 6.17 (d, $^4$J=2.4 Hz, 1H, 8-H), 6.36 (d, $^4$J=2.4 Hz, 1H, 6-H), 6.79 (d, J=8.4 Hz, 1H, 5'-H), 6.92 and 7.04 (each t, each 2H, J=9.0 Hz, 2×3''''-H, 2×5''''-H), 7.07 and 7.11 (each dd, each 2H, J=9.0 Hz, J=8.4 Hz, 2×2''''-H, 2×6''''-H), 7.42 (d, $^4$J=2.4 Hz, 1H, 2'-H), 7.62 (dd, J=8.4 Hz, $^4$J=2.4 Hz, 1H, 6'-H), 9.14 (s, 1H, 3'-OH, D$_2$O exch.), 9.81 (s, 1H, 4'-OH, D$_2$O exch.), 10.85 (s, 1H, 7-OH, D$_2$O), 12.63 (s, 1H, 5-OH, D$_2$O exch.); $^{13}$C NMR (DMSO, 150 MHz) δ 23.88 and 24.38 (2×4'''-C), 30.30 and 30.39 (2×3'''-C), 31.18 and 33.18 (2×5'''-C), 33.80 and 34.11 (2×3'''-C), 63.16 (5''-C), 68.57 (6''-C), 70.73 (4''-C), 72.36 (2''-C), 73.10 (3''-C), 93.60 (1''-C), 98.82 (8-C), 98.88 (6-C), 103.97 (4a-C), 114.21-115.10 (2×3''''-C, 2×5''''-C), 115.33 (2'-C), 115.72 (5'-C), 120.96 (6'-C), 122.41 (3-C), 129.86-130.11 (2×2''''-C, 2×6''''-C), 133.04 (2-C), 134.99 (1'-C), 138.10 and 138.24 (2×1''''-C), 145.17 (3'-C), 148.79 (4'-C), 156.37 (5-C), 159.91 (1a-C), 161.39 and 161.51 (2×4''''-C), 164.37 (7-C), 172.37 and 172.49 (2×C=O), 177.21 (4-C); FAB-MS m/z MH$^+$ ion=765; Anal. Calcd for C$_{43}$H$_{42}$O$_{14}$F$_2$·⅓H$_2$O: C, 62.58; H, 5.19. Found: C, 62.29; H, 5.00.

14l) 2-(3',4'-Dihydroxyphenyl)-5,7-dihydroxy-3-β-D-{2'',6''-di-O-[3'''-(4-methylphenylpropanoyl)]}galactosyl-4H-chromen-4-one (14l)

Yield 80%; Melting point (m.p.) 138-139° C.; IR (KBr) υ 1604 cm$^{-1}$ (C=C), 1653 and 1718 cm$^{-1}$ (C=O); 3377 cm$^{-1}$ (OH); $^1$H NMR (DMSO, 600 MHz) δ 2.21 (s, 3H, CH$_3$Ph), 2.30 and 2.52 (each t, each 2H, J=7.8 Hz, PhCH$_2$CH$_2$CO and PhCH$_2$CH$_2$CO), 3.35-3.40 (m, 1H, 5''-H), 3.54-3.58 (m, 3H, 2''-H, 3''-H, 4''-H), 3.93 (dd, 1H, J$_{5'',6''Hb}$=4.2 Hz, J$_{gem}$=11.4 Hz, 1H, 6''-Hb), 4.03 (dd, 1H, J$_{5'',6''Ha}$=4.2 Hz, J$_{gem}$=11.4 Hz, 1H, 6''-Hb), 4.71 (d, J=4.2 Hz, 1H, 2''-OH, D$_2$O exch.), 4.96 (d, J=5.4 Hz, 1H, 3''-OH, D$_2$O exch.), 5.23 (d, J=4.2 Hz, 1H, 4''-OH, D$_2$O exch.), 5.39 (dd, J$_{1'',2''}$=7.8 Hz, 1H, 1''-H), 6.14 (d, $^4$J=2.4 Hz, 1H, 8-H), 6.32 (d, $^4$J=1.8 Hz, 1H, 6-H), 6.81 (d, J=8.4 Hz, 1H, 5'-H), 6.88 and 6.97 (each d, each 2H, each J=8.4 Hz, 2''''-H, 2×6''''-H, 3''''-H, 2×5''''-H), 7.49 (d, $^4$J=2.4 Hz, 1H, 2'-H), 7.65 (dd, J=8.4 Hz, $^4$J=2.4 Hz, 1H, 6'-H), 9.15 (s, 1H, 3'-OH, D$_2$O exch.), 9.75 (s, 1H, 4'-OH, D$_2$O exch.), 10.81 (s, 1H, 7-OH, D$_2$O exch.), 12.62 (s, 1H, 5-OH, D$_2$O exch.); $^{13}$C NMR (DMSO, 150 MHz) δ 20.82 (2×PhCH$_3$), 29.91 (2'''-C), 35.33 (3'''-C), 63.57 (5''-C), 68.48 (6''-C), 71.14 (4''-C), 73.04 (2''-C), 73.09 (3''-C), 93.63 (1''-C), 98.86 (8-C), 101.66 (6-C), 103.98 (4a-C), 115.96 (2'-C), 116.11 (5'-C), 121.23 (6'-C), 122.12 (3-C), 128.10, 128.29, 128.71 and 128.91 (2''''-C, 6''''-C & 3''''-C, 5''''-C,), 129.96 and 130.02 (1''''-C, 4''''-C), 133.53 (2-C), 135.03 (1'-C), 136.99 and 137.32 (1''''-C, 4''''-C), 145.07 (3'-C), 148.69 (4'-C), 156.43 (5-C), 161.36 (1a-C), 164.29 (7-C), 171.90 (C=O), 177.63 (4-C); FAB-MS m/z MH$^+$ ion=611; Anal. Calcd for C$_{31}$H$_{30}$O$_{13}$·⅓H$_2$O: C, 60.39; H, 5.01. Found: C, 60.10; H, 5.00.

14m) 2-(3',4'-Dihydroxyphenyl)-5,7-dihydroxy-3-β-D-{2'',6''-di-O-[3'''-(4-fluorophenylpropanoyl)]}galactosyl-4H-chromen-4-one (14m)

Yield 81%; Melting point (m.p.) 125-127° C.; IR (KBr) υ 1606 cm$^{-1}$ (C=C), 1656 and 1726 cm$^{-1}$ (C=O); 3427 cm$^{-1}$ (OH); $^1$H NMR (DMSO, 600 MHz) δ 2.31 and 2.53 (each t, each 2H, J=7.8 Hz, PhCH$_2$CH$_2$CO and PhCH$_2$CH$_2$CO), 3.38-3.40 (m, 1H, 5''-H), 3.55-3.61 (m, 3H, 2''-H, 3''-H, 4''-H), 3.93 (dd, 1H, J$_{5'',6''Ha}$=4.2 Hz, J$_{gem}$=11.4 Hz, 1H, 6''-Ha), 4.03 (dd, 1H, J$_{5'',6''Hb}$=3.6 Hz, J$_{gem}$=11.4 Hz, 1H, 6''-Hb), 4.71 (br s, 1H, 2''-OH, D$_2$O exch.), 4.97 (br s, 1H, 3''-OH, D$_2$O exch.), 5.22 (d, J=4.2 Hz, 1H, 4''-OH, D$_2$O exch.), 5.40 (d, J$_{1'',2''}$=7.8 Hz, 1H, 1''-H), 6.11 (d, $^4$J=2.4 Hz, 1H, 8-H), 6.30 (d, $^4$J=1.8 Hz, 1H, 6-H), 6.81 (d, J=8.4 Hz, 1H, 5'-H), 6.97 (t, J=9.0 Hz, 2H, 3''''-H & 5''''-H), 7.02 (dd, J=8.4 Hz, J=9.0 Hz, 2H, 2''''-H, 6''''-H), 7.49 (d, $^4$J=2.4 Hz, 1H, 2'-H), 7.64 (dd, J=8.4 Hz, $^4$J=2.4 Hz, 1H, 6'-H), 9.15 (s, 1H, 3'-OH, D$_2$O exch.), 9.75 (s, 1H, 4'-OH, D$_2$O exch.), 10.80 (s, 1H, 7-OH, D$_2$O exch.), 12.62 (s, 1H, 5-OH, D$_2$O exch.); $^{13}$C NMR (DMSO, 150 MHz) δ 29.47 (2'''-C), 35.30 (3'''-C), 63.67 (5''-C), 68.48 (6''-C), 71.12 (4''-C), 73.03 (2''-C), 73.08 (3''-C), 93.60 (1''-C), 98.84 (8-C), 101.56 (6-C), 103.94 (4a-C), 114.95 and 115.00 (2''''-C, 6''''-C & 3''''-C, 5''''-C,), 115.36 (2'-C), 116.01 (5'-C), 121.22 (6'-C), 122.15 (3-C), 129.96 and 130.02 (1''''-C, 4''''-C), 133.48 (2-C), 136.54 (1'-C), 145.07 (3'-C), 148.69 (4'-C), 156.41 (5-C), 161.64 (1a-C), 164.31 (7-C), 171.75 (C=O), 177.63 (4-C); FAB-MS m/z MH$^+$ ion=615; Anal. Calcd for C$_{30}$H$_{27}$O$_{13}$F: C, 58.63; H, 4.43. Found: C, 58.59; H, 56.10.

Example 2-8

Synthesis and Identification of Final Compound 13 for Galactose Derivative (FIG. 3)

13) 2-(3',4'-Dihydroxyphenyl)-5,7-dihydroxy-3-β-D-galactosyl-4H-chromen-4-one (13)

MeONa (0.10 g, 1.80 mmol) was added to a solution obtained by dissolving 12 (758 mg, 1.20 mmol) in a mixed solvent of EtOAc-MeOH (1:1, 20 mL), and the solution was stirred at room temperature for 30 minutes. After completion of the reaction, the solution was neutralized using an ion-exchange resin Dowex 50 (H$^+$), to thereby obtain a colorless powder 13 (75%): Melting point (m.p.) 234-235° C.; IR (KBr) υ 1606 cm$^{-1}$ (C=C), 1658 cm$^{-1}$ (C=O), 3323 cm$^{-1}$ (OH); $^1$H NMR (DMSO, 400 MHz) δ 3.44 (br s, 2H, 5''-H, 4''-H), 3.53-3.58 (m, 2H, 3''-H, 6''-Hb), 3.64 (br s, 2H, 2''-H, 6''-Ha), 4.20, 4.23, 4.85 and 5.13 (each br s, each 1H, 2''-OH, 3''-OH, 4''-OH, 6''-OH, each D$_2$O exch.), 5.38 (d, J$_{1'',2''}$=7.5 Hz, 1H, 1''-H), 6.18 (d, 4J=1.8 Hz, 1H, 8-H), 6.39 (d, 4J=1.8 Hz, 1H, 6-H), 6.81 (d, J=9.0 Hz, 1H, 5'-H), 7.51 (d, 4J=2.4 Hz, 1H, 2'-H), 7.67 (dd, J=8.4 Hz, 4J=2.4 Hz, 1H, 6'-H), 9.15 (s, 1H, 3'-OH, D$_2$O exch.), 9.72 (s, 1H, 4'-OH, D$_2$O exch.), 10.86 (s, 1H, 7-OH, D$_2$O exch.), 12.63 (s, 1H, 5-OH, D$_2$O exch.); FAB-MS m/z MH+ion=465; Anal. Calcd for C$_{21}$H$_{20}$O$_{12}$: C, 54.31; H, 4.34. Found: C, 54.09; H, 4.16.

Experimental Example 2-1

In Vitro Infectivity Assay (MIC)

The antibacterial activities of the final compounds shown in Examples 2-7 and 2-8 were examined. Conventional antibacterial drugs, quercetin, vancomycin, norfloxacin, novobiocin, and penicillin were used as controls.

The antibacterial activities were measured based on broth dilution techniques of international standards (Clinical Laboratory Standards Institute: CLSI). The activities were shown by minimum inhibitory concentrations (MICs) determined by inoculating the above-mentioned strains at a concentration of about 10$^5$ CUF/100 mL into Mueller-Hinton broth (manufactured by Difco) containing 0.85% NaCl in 96-well microplates and incubating the plates at 35° C. for 24 hours. Measurement was carried out three times.

The antibacterial activities of the compounds of the present invention against various strains such as vancomycin-resistant enterococci (VRE), vancomycin intermediate-resistant *Staphylococcus aureus* (VISA), methicillin-resistant *Staphy-* lococcus aureus (MRSA), and methicillin-sensitive *Staphylococcus aureus* (MSSA) were examined. Of the bacteria used in MIC measurement in this test example, clinical bacteria of MRSA (OM481 strain and OM584 strain) were supplied from Okayama University Hospital (Japan). An MRSA strain N315, a vancomycin intermediate-resistant *Staphylococcus aureus* (VISA) strain Mu50, and a methicillin-sensitive *Staphylococcus aureus* (MSSA) strain FDA 209P were used as controls. Vancomycin-resistant *enterococcus* (VRE) strains NCTC 12201 and FN-1 were supplied from the National Institute of Infectious Disease (Japan).

Table 3 below shows the results.

purchased from John Innes Enterprises (Gyrase Supercoiling assay kit #K0001) was used. Relaxed DNA was modified with gyrase into supercoiled DNA, and reaction products were separated by electrophoresis depending on the sizes of the molecular weights to examine anti-gyrase effects ($IC_{50}$). 1 unit (1 U) of DNA gyrase and 0.5 mg of relaxed pBR322 DNA were added to 30 mL of the reaction solution, and the mixture was allowed to react at 37° C. for 30 minutes in the presence of 35 mM Tris-HCl (pH 7.5), 24 mM KCl, 4 mM $MgCl_2$, 2 mM DTT, 1.8 mM spermidine, 1 mM ATP, 6.5%

TABLE 3

Antibacterial activity (MICs) against Gram-positive bacterial strains.

| Compound number (FIG. 3) | $MIC^a$ (μg/mL, Gram-positive) | | | | | | | | |
|---|---|---|---|---|---|---|---|---|---|
| | VRE | | VISA | MRSA | | | | MSSA | *S. Pneumoniae* |
| | $FN-1^b$ | $12201^c$ | $Mu50^d$ | $OM481^e$ | $OM584^f$ | $N315^g$ | $COL^h$ | $209P^i$ | $R6^j$ |
| 2a | 64 | 64 | 16 | 32 | 32 | 32 | 32 | 64 | 32 |
| 2b | 64 | 32 | 32 | 16 | 16 | 16 | 32 | 64 | 32 |
| 5 | 32 | 32 | 64 | 32 | 32 | 64 | 128 | 64 | 64 |
| 6 | >128 | >128 | >128 | >128 | >128 | >128 | >128 | >128 | >128 |
| 12 | 64 | 64 | 128 | 128 | 128 | 128 | >128 | 128 | 128 |
| 13 | >128 | >128 | >128 | >128 | >128 | >128 | >128 | >128 | >128 |
| 14a | 8 | 8 | 4 | 4 | 4 | 8 | 16 | 4 | 4 |
| 14b | 8 | 4 | 4 | 4 | 4 | 2 | 16 | 2 | 2 |
| 14c | 4 | 4 | 2 | 2 | 2 | 8 | 8 | 4 | 4 |
| 14d | 8 | 4 | 4 | 2 | 2 | 8 | 16 | 4 | 2 |
| 14e | 0.5 | 0.5 | 1 | 1 | 1 | 1 | 8 | 1 | 0.5 |
| 14f | 4 | 4 | 2 | 1 | 1 | 2 | 4 | 2 | 4 |
| 14g | 2 | 2 | 1 | 1 | 1 | 2 | 4 | 2 | 8 |
| 14h | 0.5 | 0.5 | 0.5 | 0.25 | 0.25 | 0.25 | 1 | 0.25 | 0.25 |
| 14i | 0.25 | 0.25 | 0.5 | 0.13 | 0.13 | 0.13 | 0.5 | 0.13 | 0.13 |
| 14j | 8 | 8 | 4 | 2 | 2 | 4 | 16 | 4 | 2 |
| 14k | 16 | 16 | 16 | 4 | 4 | 2 | 16 | 4 | 8 |
| 14l | 32 | 32 | 16 | 16 | 16 | 16 | 32 | 16 | 32 |
| 14m | 16 | 16 | 32 | 16 | 16 | 16 | 32 | 16 | 32 |
| Quercetin | >128 | >128 | >128 | >128 | >128 | >128 | >128 | >128 | >128 |
| Vancomycin | >128 | >128 | 8 | 0.25 | 0.25 | 0.25 | 0.25 | 0.25 | 0.25 |
| Norfloxacin | nt | nt | nt | 64 | 128 | 2 | 1 | 0.5 | 0.25 |
| Novobiocin | nt | nt | 8 | 0.25 | 0.25 | 0.125 | 0.25 | 0.125 | nt |
| Penicillin | nt | nt | nt | nt | nt | nt | nt | nt | 0.5 | nt, not tested;
$^a$Microdilution method, MIC determined after 24 h.
$^b$Vancomycin-resistant enterococci FN-1.
$^c$Vancomycin-resistant enterococci NCTC 12201.
$^d$Vancomycin intermediate-resistant *Staphylococcus aureus* Mu50.
$^e$Methicillin-resistant *S. aureus* OM481.
$^f$Methicillin-resistant *S. aureus* OM584.
$^g$Methicillin-resistant *S. aureus* N315.
$^h$Methicillin-resistant *S. aureus* COL.
$^i$Methicillin sensitive *S. aureus* 209P.
$^j$*Streptococcus pneumoniae* R6.

Experimental Example 2-2

Determination of DNA Gyrase Inhibition ($IC_{50}$)

DNA gyrase inhibition ($IC_{50}$) of the final compounds shown in Examples 2-7 and 2-8 was examined. As a kit for measurement of DNA gyrase of *Escherichia coli*, a product (w/v) glycerol, and 0.1 mg/ml BSA. The reactions were stopped using 8 mL of a reaction stop solution (40% sucrose, 100 mM Tris-HCl (pH 7.5), 1 mM EDTA, 0.5 mg/ml bromophenol blue). The $IC_{50}$ value means a concentration required for 50% inhibition of the supercoiling activity.

Table 4 below shows the results.

TABLE 4

Antibacterial activity (MICs) against Gram-negative bacterial strains
and DNA gyrase inhibition (IC50) against DNA gyrase supercoiling kit from *E. coli*, and
topoisomerase IV inhibition against topoisomerase IV decatenation kit from *E. coli* and *S. aureus*.

| Compound number (FIG. 3) | MIC$^a$ (μg/mL, Gram-nagative) | | IC$_{50}$$^d$ (μM, E. coli DNA gyrase inhibitions) | IC$_{50}$$^d$ (μM, E. coli topoisomerase IV inhibitions) | IC$_{50}$$^d$ (μM, S. aureus topoisomerase IV inhibitions) |
|---|---|---|---|---|---|
| | PAO1$^b$ | K-12$^c$ | | | |
| 2a | 64 | 64 | 1.66 | 4.59 | 0.44 |
| 2b | 64 | 64 | 0.72 | 2.76 | 0.29 |
| 5 | >128 | >128 | nt | nt | nt |
| 6 | 32 | 16 | 0.14 | 1.07 | 0.07 |
| 12 | >128 | >128 | nt | nt | nt |
| 13 | 32 | 32 | 026 | 3.34 | 0.20 |
| 14a | >128 | >128 | 0.43 | 7.33 | 1.78 |
| 14b | >128 | >128 | 0.77 | 8.89 | 1.93 |
| 14c | >128 | >128 | 0.38 | 7.02 | 0.52 |
| 14d | >128 | >128 | 2.21 | 8.52 | 2.69 |
| 14e | >128 | >128 | 1.05 | 7.21 | 0.46 |
| 14f | >128 | >128 | 2.39 | 8.86 | 1.59 |
| 14g | >128 | >128 | 5.39 | >12 | 2.99 |
| 14h | >128 | >128 | 2.09 | 7.46 | 1.49 |
| 14i | >128 | >128 | 0.78 | 7.16 | 0.22 |
| 14j | >128 | >128 | 2.98 | 8.96 | 2.94 |
| 14k | >128 | >128 | 5.02 | >12 | 4.05 |
| 14l | >128 | >128 | 1.79 | 7.99 | 2.57 |
| 14m | >128 | >128 | 1.40 | 7.52 | 2.99 |
| Quercetin | >128 | 64 | 0.14 | 4.42 | nt |
| Vancomycin | nt | nt | nt | nt | nt |
| Norfloxacin | 0.25 | 0.25 | 0.09 | nt | nt |
| Novobincin | 8 | 8 | 0.05 | nt | nt | nt, not tested;
$^a$Microdilution method, MIC determined after 24 h.
$^b$*Pseodomonas aeruginosa* PAOI.
$^c$*Escherichia coli* K-12.
$^d$IC50 the concentration of the drugs that inhibits 50% of supercoiling activity.

Experimental Example 2-3

Quantification of Topoisomerase IV Inhibition (IC$_{50}$)

Topoisomerase IV inhibition (IC$_{50}$) of the final compounds shown in Examples 2-7 and 2-8 was examined. *Staphylococcus aureus* Topoisomerase IV and *Escherichia coli* Topoisomerase IV were purchased from John Innes Enterprises. 1 unit of topoisomerase IV was cultured with 200 ng of kinetoplast DNA (kDNA) in 30 L of a reaction solution at 37° C. for 30 minutes under the conditions of 50 mM Tris-HCl (pH 7.5) (*S. aureus*)/50 mM HEPES-KOH (pH 7.6) (*E. coli*), 5 mM MgCl$_2$ (*S. aureus*)/5 mM magnesium acetate (*E. coli*), 350 mM potassium glutamate (*S. aureus*)/100 mM potassium glutamate (*E. coli*), 5 mM dithiotheri (*S. aureus*)/10 mM dithiotheri (*E. coli*), 1.5 mM ATP (*S. aureus*)/1 mM ATP (*E. coli*), and 40% (w/v) glycerol. The reactions were stopped by adding 8 L of a reaction stop solution (40% sucrose, 100 mM Tris.HCl (pH 7.5), 1 mM EDTA, 0.5 mg/ml bromophenol blue). Agarose gel (1.0%) was poured into TAE (40 mM Tris acetate, 2 mM EDTA). The concentration of a drug required for 50% inhibition of the decatenating activity was determined by substituting values obtained using densitometry and NIH images into the following equation.

$$IC_{50}=10^{\wedge}(LOG(A/B)*(50-C)/(D-C)+LOG(B))$$

A: Higher concentration near 50%
B: Lower concentration near 50%
C: Inhibition rate at B
D: Inhibition rate at A Table 4 above shows the results.

Experimental Example 3

Acute Toxicity Evaluation Experiment

An acute toxicity test of the compound of the present invention was carried out using ICR mice as experimental animals.
1) Experimental Method
A solution obtained by dissolving the compound represented by the formula (III) (15d (FIG. 2)) in a solvent (PEG:physiological saline=50:50) was administered to ICR mice at a concentration of 20 mL/kg (10 mg/kg or 100 mg/kg) for 4 consecutive days, and changes in the body weights were measured over 7 days.
2) Experimental Results
In the case of the group in which the compound was administered at 100 mg/kg (four mice), the body weights of all the four mice were reduced from the day after administration, and all the mice in the group were dead on days 5 to 7 after administration (one mouse was dead on day 5, two mice were dead on day 6, and one mouse was dead on day 7). On the other hand, in the case of the group in which the compound was administered at 10 mg/kg (four mice), the body weights were slightly reduced from the day after administration, but the body weights of all the four mice were recovered from about day 5 after administration. All the mice were not dead until day 7.

Experimental Example 4

Gastrointestinal Absorption Evaluation Experiment

A gastrointestinal absorption evaluation test of the compound of the present invention was carried out using Wistar male rats (four rats) as experimental animals.

1) Experimental Method

This experiment was carried out according to an in situ small-intestinal absorption experimental method.

The abdomen of a rat under pentobarbital anesthesia was opened to prepare a loop of the small intestine (full length), and a known amount of the compound represented by the formula (III) (15d (FIG. 2)) (dissolved in a solvent (PEG: physiological saline=50:50)) was administered to the loop at 1 mg/1 mL (sample solution). One hour later, the small intestine loop was washed, and the total of the washing solution was collected to 10 mL with physiological saline. The amount of the compound in the washing solution collected was quantified, and a difference between the resultant value and the amount of the compound administered was calculated as an absorption amount. The sample solution was administered at 1 mg/1 mL to the gastrointestinal tract, and one hour later, the residual solution was collected with 10 mL of physiological saline. That is, the concentration of the solution collected was 0.1 mg/mL. The solution was centrifuged at 1,500 rpm for 10 minutes because impurities were mixed in the solution collected. Then, the supernatant was subjected to extraction with chloroform, and the solvent was evaporated under reduced pressure. The residue was dissolved in 10 mL of methanol. Quantification of the solution was carried out using a spectrophotometer (measurement wavelength: 340 nm).

2) Experimental Results

The gastrointestinal absorption ratio was found to be 76.6%±1.2 (average±S.D, n=4).

INDUSTRIAL APPLICABILITY

As mentioned in detail above, the novel flavanone derivative of the present invention was found to have a strong antibacterial activity against not only MRSA but also VRSA. Therefore, the novel flavanone derivative of the present invention has an excellent function as a novel synthetic antimicrobial agent, and hence can be used for a medicine or disinfectant containing the flavanone derivative as an active ingredient.

The invention claimed is:

1. A flavanone derivative of the formula:

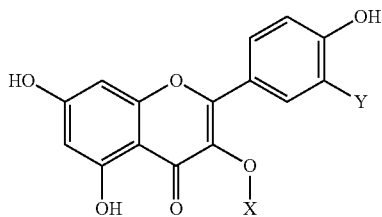

I or a pharmaceutically acceptable salt thereof,
wherein
X is
a glucose derivative having unsubstituted hydroxyl groups at positions 1, 4 and 6, and hydroxyl groups at positions 2 and 3 are substituted with a moiety of the formula —$R_5$—Z; or
a galactose derivative having unsubstituted hydroxyl groups at positions 1, 3 and 5, and hydroxyl groups at position 2 or 6 or both are substituted with a moiety of the formula —$R_5$—Z; and Y is a hydroxyl group,
wherein
$R_5$ is —C(=O)— or an acyl group, and
Z is an optionally substituted phenyl, wherein when said phenyl is substituted, the substituent is selected from the group consisting of an acyl group, an alkyl group, an alkenyl group, an alkynyl group, an alkyloxy group, a benzyloxy group, an amino group, a cyano group, a halogen, and a carboxyl group.

2. The flavanone derivative according to claim 1, wherein Z is phenyl group that is optionally substituted at the para-position.

3. The flavanone derivative according to claim 2 of the formula:

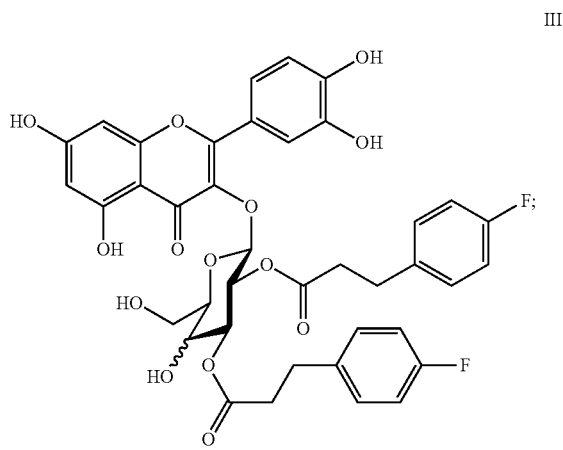

III

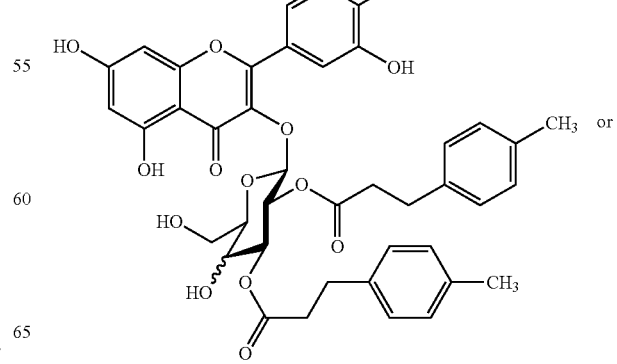

IV or

-continued

V

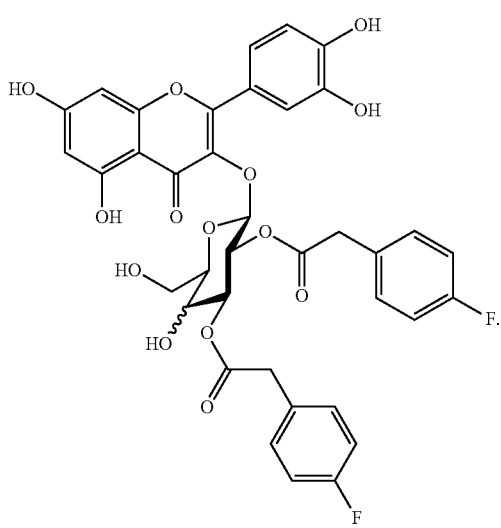

4. An antimicrobial agent comprising a flavanone derivative of claim 1.

5. The antimicrobial agent according to claim 4, wherein said antimicrobial agent has an antibacterial effect on *Staphylococcus aureus*.

6. The antimicrobial agent according to claim 5, wherein said antimicrobial agent has an antibacterial effect on methicillin-resistant *Staphylococcus aureus*, vancomycin-resistant *Staphylococcus aureus*, or a combination thereof.

7. An antimicrobial composition comprising an antimicrobial agent of claim 4 as an active ingredient and a pharmaceutically acceptable carrier.

\* \* \* \* \*